United States Patent [19]

Suzuki

[11] Patent Number: 5,798,224

[45] Date of Patent: Aug. 25, 1998

[54] NUCLEIC ACIDS ENCODING PROTOCADHERIN

[75] Inventor: Shintaro Suzuki, Torrance, Calif.

[73] Assignee: Doheny Eye Institute, Los Angeles, Calif.

[21] Appl. No.: 268,161

[22] Filed: Jun. 27, 1994

Related U.S. Application Data

[63] Continuation-in-part of Ser. No. 998,003, filed as PCT/US93/12588, Dec. 23, 1993, Pat. No. 5,643,781.

[51] Int. Cl.$^6$ .................................................... C12N 15/09
[52] U.S. Cl. ................... 435/69.1; 536/23.5; 435/252.3; 435/254.11; 435/320.1; 435/325
[58] Field of Search ........................... 435/69.1, 240.1, 435/252.3, 254.11, 320.1, 240.2, 325; 536/23.1, 23.5

[56] References Cited

FOREIGN PATENT DOCUMENTS

WO91/04745  4/1991  WIPO .
WO92/08731  5/1992  WIPO .

OTHER PUBLICATIONS

Sago et al., Genomics, 29, 631–640 (1995).
Pytela et al., Methods in Enzymology, vol. 245, pp. 420–451, 1995, Academic Press.
Sano et al., Embo J., vol. 12, pp. 2249–2256, 1993.
Amagai et al., "Autoantibodies against a Novel Epithelial Cadherin in Pemphigus Vulgaris, a Disease of Cell Adhesion", Cell, 67: 869–877 (Nov. 29, 1991).
Angerer et al., "Demonstration of Tissue–Specific Gene Expression by in Situ Hybridization", *Methods in Enzymology*, 152: 649–660, (1987).
Ausubel et al., Eds., *Current Protocols in Molecular Biology*, Sections 6.1.1 to 6.1.4 and 6.2.1 to 6.2.3, John Wiley & Sons, New York (1987).
Burt, "Morphologic Abnormalities in the Postnatal Differentiation of CA1 Pyramidal Cells and Granule Cells in the Hippocampal Formation of the Ataxic Mouse", *Anat. Rec.* 196: 61–69 (1980).
Chen et al., Cell–Cell Contacts Mediated by E–Cadherin (Uvomorulin) Restrict Invasive Behavior of L–Cells:, *J. Cell. Biol.*, 114(2):319–327 (Jul. 1991).
Civitelli et al., "Connexin43 Mediates Direct Intercellular Communication in Human Osteoblastic Cell Networks", *J. Clin. Invest.*, 91: 1888–1896 (1993).
Detrick et al., "The Effects of N–Cadherin Misexpression on Morphogenesis in Xenopus Embryos", *Neuron*, 4: 493–506 (Apr. 1990).
Donalies et al., "Expression of M–cadherin, a Member of the Cadherin Multigene Family, Correlates with Differentiation of Skeletal Muscle Cells", *Proc. Natl. Acad. Sci. USA*, 88: 8024–8028 (Sep. 1991).
Frixen et al., "E–Cadherin–Mediated Cell–Cell Adhesion Prevents Invasiveness of Human Carcinoma Cells" *J. Cell. Biol.*, 113(1): 173–185 (Apr. 1991).

Fujimori et al., "Ectopic Expression of N–cadherin Perturbs Histogenesis in *Xenopus* Embryos", *Development*, 110:97–104 (1990).
Gallin et al., "Sequence Analysis of a cDNA Clone Encoding the Liver Cell Adhesion Molecule, L–CAM", *Proc. Natl. Acad. Sci. USA*, 84: 2808–2812 (May 1987).
Goodwin et al., "Desmoglein Shows Extensive Homology to the Cadherin Family of Cell Adhesion Molecules", *Biochem. Biophsy. Res. Commun.*, 173(3): 1224–1230 (Dec. 31, 1990).
Hatta et al., "Cloning and Expression of cDNA Encoding a Neural Calcium–dependent Cell Adhesion Molecule: Its Identity in the Cadherin Gene Family", *J. Cell. Biol.*, 106: 873–881 (Mar. 1988).
Holton et al., "Desmosomal Glycoproteins 2 and 3 (desmocollins) Show N–terminal Similarity to Calcium–Dependent Cell–Cell Adhesion Molecules", *J. Cell. Science*, 97:239–246 (1990).
Hynes et al., "Contact and Adhesive Specification in the Associations, Migrations, and Targeting of Cells and Axons", Cell, 68: 303–322, (Jan. 24, 1992).
Inuzuka et al., "R–Cadherin: A Novel $Ca^{2+}$–Dependent Cell–Cell Adhesion Molecule Expressed in the Retina", *Neuron*, 7: 69–79 (1991).
Kenneth, "Cell Fusion", *Methods in Enzymol.*, 58: 345–359 (1979).
Kikuchi et al., "The Defective Organ of Corti in Shaker–1 Mice", *Acta Oto–Laryng.*, 60: 287–303 (1965).
Kintner, "Regulation of Embryonic Cell Adhesion by the Cadherin Cytoplasmic Domain", Cell, 69: 225–236 (Apr. 17, 1992).
Koch et al., "Identification of Desmoglein, a Constitutive Desmosomal Glycoprotein, as a Member of the Cadherin Family of Cell Adhesion Molecules", *Eur. J. Cell Biol.*, 53: 1–12 (1990).
Liaw et al., "Identification and Cloning of Two Species of Cadherins in Bovine Endothelial Cells", EMBO J., 9(9): 2701–2708 (1990).
Lord et al., Shaker, A New Mutation of the House Mouse (Mus Musculus) *Am Nat.*, 63: 453–442 (1929).
Lyon, M., "Twirler: A Mutant Affecting the Inner Ear of the House Mouse", *J. Embryol. Exp. Morphol.*, 6: 105–116 (1958).
Lyon, M., "Ataxia—A New Recessive Mutant of the House Mouse", J. Hered., 46: 77–80 (1955).

(List continued on next page.)

*Primary Examiner*—Sally P. Teng
*Attorney, Agent, or Firm*—Marshall, O'Toole, Gerstein, Murray & Borun

[57] ABSTRACT

Polynucleotide sequences encoding novel cadherin-like polypeptides, designated protocadherins, and variants thereof are provided by the invention as well as methods and materials for the recombinant production of the same. Antibody substances specific for protocadherins are also disclosed as useful for modulating the natural binding and/or regulatory activities of the protocadherins.

12 Claims, 3 Drawing Sheets

OTHER PUBLICATIONS

Mahoney et al., "The fat Tumor Suppressor Gene in Drosophila Encodes a Novel Member of the Cadherin Gene Superfamily", Cell, 67: 853–868 (Nov. 29, 1991).

Maniatis et al., pp. 196 in *Molecular Cloning: A Laboratory Manual*, Cold Spring Harbor, New York: Cold Spring Harbor Laboratory (1982).

Maruyama et al., "Detection of Calcium Binding Proteins by [45]Ca Autoradiography on Nitrocellulose Membrane after Sodium Dodecyl Sulfate Gel Electrophoresis[1]", *J. Biochem.*, 95: 511–519 (1984).

Matsunaga et al., "Guidance of Optic Nerve Fibers by N–cadherin Adhesion Molecules", *Nature*, 334: 62–64 (Jul. 1988).

Miyatani et al., "Neural Cadherin: Role in Selective Cell–Cell Adhesion", *Science*, 245: 631–635 (Aug. 1989).

Nagafuchi et al., "Transformation of Cell Adhesion Properties by Exogenously Introduced E–cadherin cDNA", *Nature*, 329: 341–343 (Sep. 1987).

Napolitano, et al., "Molecular Cloning and Characterization of B–Cadherin, a Novel Chick Cadherin", *Bell Biol.*, 113(4): 893–905 (May 1991).

Nose et al., "Isolation of Placental Cadherin cDNA: Identification of a Novel gene Family of Cell–Cell Adhesion Molecules", EMBO J., 6(12): 3655–3661 (1987).

Porter et al., "Dystrophin Colocalizes with β–Spectrin in Distinct Subsarcolemmal Domains in Mammalian Skeletal Muscle", *J. Cell Biol.*, 117(5): 997–1005 (Jun. 1992).

Pytela et al., "Polymerase Chain Reaction Cloning with Degenerate Primers: Homology–Based Identification of Adhesion Molecules", *Methods in Enzymology*, Erkki Ruoslahti and Eva Engvall, Eds., 245:420–451, Academic Press, (1994).

Ranscht et al., "T–Cadherin, a Novel Cadherin Cell Adhesion Mol. in the Nervous System Lacks the Conserved Cytoplasmic Region", *Neuron*, 7: 391–402 (Sep. 1991).

Ringwald et al., "The Structure of Cell Adhesion Molecule Uvomorulin. Insights into the Molecular Mechanism of $Ca^{2+}$–Dependent Cell Adhesion", EMBO J., 6(12): 3647–3653 (1987).

Sano et al. "Protocadherins: A Large Family of Cadherin–Related Molecules in Central Nervous System", *The EMBO Journal*, 12(6): 2249–2256 (1993).

Seldon et al., "Genetic Analysis of Autoimmune gld Mice", *J. Exp. Med.*, 167: 688–693 (1988).

Shimoyama et al., "Molecular Cloning of a Human $Ca^{2+}$–Dependent Cell–Cell Adhesion Molecule Homologous to Mouse Placental Cadherin: Its Low Expression in Human Placental Tissues", *J. Cell. Biol.*, 109: 1787–1794 (Oct. 1989).

Suzuki et al., "Diversity of the Cadherin Family: Evidence for Eight New Cadherins in Nervous Tissue", *Cell Regulation*, 2: 261–270 (Apr. 1991).

Suzuki et al., "Evidence for Cadherin Superfamily" *Cell Struc. Func.*, 16: 605 (Nov. 23, 1991).

Suzuki et al., "Evidence for Cadherin Superfamily" *J. Cell. Biol.*, 115: 72(a) (Abstract 416) (Dec. 9, 1991).

Takeichi, Cadherin Cell Adhesion Receptors as a Morphogenetic Regulator:, *Science*, 251: 1451–1455 (Mar. 1991).

Takeichi, Cadherins: A Molecular Family Important in Selective Cell–Cell Adhesion:, *Annu. Rev. Biochem.*, 59: 237–252 (1990).

Thomas, "Hybridization of Denatured RNA and Small DNA Fragments Transferred to Nitrocellulose", *Proc. Natl. Acad. Sci. USA*, 77(9): 5201–5205 (Sep. 1980).

Towbin et al., Electrophoretic Transfer of Proteins from Polyacrylamide Gels to Nitrocellulose Sheets: Procedure and Some Applications: PNAS 76: 4350–4354, (Sep. 1979).

Urushihara et al., "Immunological Detection of Cell Surface Components Related with Aggregation of Chinese Hamster and Chick Embryonic Cells", *Dev. Biol.*, 70: 206–216 (1979).

Vandenbark et al., "Experimental Allergic Encephalomyelitis and Cellular Immunity in the Lewis Rat", *Cell. Immunol.*, 12: 85–93 (1974).

Vleminckx et al., "Genetic Manipulation of E–Cadherin Expression by Epithelial Tumor Cells Reveals an Invasion Suppressor Role", Cell, 66: 107–119 (Jul. 12, 1991).

```
PC43   EC 1   (29)   ASTVIHYEIPEEREK------GFAVGNVVANL--GLDLGSLSA--   (63)
       EC 2   (136)  PTQEMKLEISEAVAP------GTRFPLESAH---DPDLGSNSL--   (169)
       EC 3   (245)  NQSLYRARVPGGCTS------GTRVVQVLAT---DLDEGPNGE--   (278)
       EC 4   (353)  TVTSVYSPVPEDAS-------GTVIALLSVT---DLDAGENGL--   (385)
       EC 5   (457)  SQSSYDVYIEENNLP------GAPILNLSVW---DPDAPQNAR--   (490)
       EC 6   (567)  LYPRPGGSSVEMLPRGTSA--GHLVSRVVGW---DADAGHNAW--   (604)

PC42   EC 1   (42)   VPEEQPPNTLI----------GSL----------AADYGFPDVG-   (65)
       EC 2   (147)  ASPVITLAIPENTNI------GSLFPIPLAS---DRDAGPNGV--   (180)
       EC 3   (247)  ERPSYEAELSENSPI------GHSVIQVKAN---DSDQGANAE--   (280)
       EC 4   (354)  EIRGIGLVTHQDGMANISEDVAEETAVALVQVSDRDEGENAA--   (395)
       EC 5   (473)  TQSVTEVAFPENNKP------GEVIAEITAS---DADSGSNAE--   (506)
       EC 6   (579)  MLSGYNFSVMENMPA------LSPVGMVTVI---DGDKGENAQ--   (612)
       EC 7   (682)  TAPSNTSHKLLTPQTRL----GETVSQVAAE---DFDSGVNAE--   (717)

FAT    EC18   (1)    EDTVYSFDIPENAQR------GYQVGQIVAR---DADLGQNAQ--   (34)

N-CAD  EC 1   (1)    DWVIPPINLPENSRG------PFPQELVRIRS--DRDKNLSLRYT   (37)
       EC 2   (109)  LHQVWNGSVPEGSKP------GTYVMTVTAI---DADDPNALNGM   (144)
       EC 3   (224)  TAMTFYGEVPENRVD------IIVANLTVT----DKDQPHTPAWN   (258)
       EC 4   (339)  APNPKIIRQEEGLHA------GTMLTTFTAG---DPDRYMQQN--   (372)
       EC 5   (447)  LPQEAETCETPDPNSINITTAL------------DYDIDPNAGP-   (478)

MOTIF         *****o****v*En****-------Gt*v***v*A*----D*D*G*N**---
```

FIGURE 1A

```
PC43  EC 1  (64)   RRFPVVSGASRR--------FFEVNRET----GEMFVNDR----  (91)
      EC 2  (170)  QTYELSRNEY----------FALRVQTREDSTKYAELVLERA-- (201)
      EC 3  (279)  IIYSFGSHNRAGVRQL----FALDLVT----GMLTIKGR----  (309)
      EC 4  (386)  VTCEVPPGLP----------FSLTSSLKNYFTLKTSAD----  (413)
      EC 5  (491)  LSFFLLEQGAETGLVGRYFTINRDN-----GIVSSLVP----  (523)
      EC 6  (605)  LSYSLFGSPNQSL-------FAIGLHT----GQISTARPV--- (633)

PC42  EC 1  (66)   HLYKLEVGAP----------YLRVDGKT----GDIFTTETS--- (92)
      EC 2  (181)  ASYELQVAED----------QEEKQPQLIVMGN-------    (203)
      EC 3  (281)  IEYTFHQAPEVVRRL-----LRLDRNT----GLITVQGP---  (310)
      EC 4  (396)  VTCVVAGDVP----------FQLRQASETGSDSKKKYFLQTTTP (429)
      EC 5  (507)  LVYSLEPEPAAKGL------FTISPET----GEIQVKTS---  (535)
      EC 6  (613)  VQLSVEQDNGD---------FVIQNGT----GTILSSLS---  (638)
      EC 7  (718)  LIYSIAGGNPYGL-------FQIGSHS----GAITLEKE---  (745)

FAT   EC18 (35)    LSYGVVSDWANDV-------FSLNPQT----GMLTLTAR---  (62)

N-CAD EC 1  (38)   VTGPGADQPPTGI-------FIINPIS----GQLSVTKP---  (65)
      EC 2  (145)  LRYRILSQAPSTPSPNM-FTINNET----GDIITVAAG---  (177)
      EC 3  (259)  AVTRISGGDPTGR-------FAIQTDPNSND-GLVTVVKP--- (290)
      EC 4  (373)  IRYTKLSDPAN---------WLKIDPVN---GQITTIAV---  (399)
      EC 5  (479)  FAYDLPLSPVTIKRN-----WTITRLN----GDFAQLNLK--- (509)

Motif              I*o*I***********o*I***T------G*I*T***----
```

FIGURE 1B

```
PC43  EC 1  (92)   LDREELCGTLPSCTVTLELVVENP------------------LELFSVEVVIQDINDNNPAF  (135)
      EC 2  (202)  LDREREPSLQLVLTALDGGTPAL-------------------SASLPIHIKVLDANDNAPVF  (244)
      EC 3  (310)  LDFEDTKLHEIYIQAKDKGANPE-------------------GAHCKVLVEVDVNDNAPEI  (352)
      EC 4  (414)  LDRETVPEYNLSITARDAGTPSL-------------------SALTIVRVQVSDINDNPPQS  (456)
      EC 5  (524)  LDYEDRREFELTAHISDGGTPVL-------------------ATNISVNIFVTDRNDNAPQV  (566)
      EC 6  (634)  QDTDSPRQTLTVL-IKDNGEPSLSTTATLTVSVTEDSPEARAEFPSGSAPREQKKN      (688)

PC42  EC 1  (93)   IDREGLRECQNQLPGDPCILEFEVSITDLVQNAS--PRLLEGQIEVQDINDNTPNF       (146)
      EC 2  (204)  LDRERWDSYDLTIKVQDGGSPPR-------------------ATSALLRVTVLDTNDNAPKF  (246)
      EC 3  (311)  VDREDLSTLRFSVLAKDRGTNPK-------------------SARAQVVVTVKDMNDNAPTI  (353)
      EC 4  (430)  LDYEKVKDYTIEIVAVDSGNPPL-------------------SSTNSLKVQVVDVNDNAPVF  (472)
      EC 5  (536)  LDREQRESYELKVVAADRGSPSL-------------------QGTATVLVNVLDCNDNDPKF  (578)
      EC 6  (639)  FDREQQSTYTFQLKAVDGGVPPR-------------------SAYVGVTINVLDENDNAPYI  (681)
      EC 7  (746)  IERRHHGLHRLVVKVSDRGKPPPRYGTALVHLYVNETLANRTLLETLLGHSLDTPLD      (801)
                                                   (802) IDIAGDPEYERSKQRGN              (818)

FAT   EC18 (63)    LDYEEVQHYILIVQAQDNGQPSL-------------------STTITVYCNVLDLNDNAPIF  (105)

N-CAD EC 1  (66)   LDREQIARFHLRAHAVDINGNQV-------------------ENPIDIVINVIDMNDNRPEF  (108)
      EC 2  (178)  LDREKVQQYTLIIQATDMEGNPTYGL----------------SNTATAVITVTDVNDNPPEF  (223)
      EC 3  (291)  IDFETNRMFVLTVAAENQVPLAKGIQHPP-------------QSTATVSVTVIDVNE-NPYF  (338)
      EC 4  (400)  LDRESPNVKNNIYNATFLASDNGIPPM---------------SGTGTLQIYLLDINDNAPQV  (446)
      EC 5  (510)  IKFLEAGIYEVPIIITDSGNPPKSNKS---------------ILRVRVCQCDFNGDCTDVDR  (557)

MOTIF              LDRE*****o*L*v*A*D*G*P**------------------**t*Tv*v*V*D*NDNAP*F
```

FIGURE 1C

NUCLEIC ACIDS ENCODING PROTOCADHERIN

This application is a continuation-in-part of International Patent Application No. PCT/US93/12588 filed Dec. 23, 1993 which is in turn a continuation-in-part of U.S. patent application Ser. No. 07/998,003 which was filed on Dec. 29, 1992, now U.S. Pat. No. 5,643,781.

FIELD OF THE INVENTION

The present invention relates, in general, to materials and methods relevant to cell-cell adhesion. More particularly, the invention relates to novel adhesion proteins, designated protocadherins, and to polynucleotide sequences encoding the protocadherins. The invention also relates to methods for inhibiting binding of the protocadherins to their natural ligands/antiligands.

BACKGROUND

In vivo, intercellular adhesion plays an important role in a wide range of events including morphogenesis and organ formation, leukocyte extravasion, tumor metastasis and invasion, and the formation of cell junctions. Additionally, cell-cell adhesion is crucial for the maintenance of tissue integrity.

Intercellular adhesion is mediated by specific cell surface adhesion molecules. Cell adhesion molecules have been classified into at least four families including the immunoglobulin superfamily, the integrin superfamily, the selectin family and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain (the N-terminal 113 amino acids of the domain appear to be directly involved in binding) consisting of five subdomains characterized by sequences unique to cadherins, a hydrophobic membrane-spanning domain and a C-terminal cytoplasmic domain that interacts with the cytoskeleton through catenins and other cytoskeleton-associated proteins. Some cadherins lack a cytoplasmic domain, however, and appear to function in cell-cell adhesion by a different mechanism than cadherins having a cytoplasmic domain. The cytoplasmic domain is required for the adhesive function of the extracellular domain in cadherins that do have an cytoplasmic domain. Binding between members of the cadherin family expressed on different cells is homophilic (i.e., a member of the cadherin family binds to cadherins of its own or a closely related subclass) and $Ca^{2+}$-dependent. For recent reviews on cadherins, see Takeichi, Annu. Rev. Biochem., 59: 237–252 (1990) and Takeichi, Science, 251: 1451–1455 (1991).

The first cadherins to be described (E-cadherin in mouse epithelial cells, L-CAM in avian liver, uvomorulin in the mouse blastocyst, and CAM 120/80 in human epithelial cells) were identified by their involvement in $Ca^{2+}$-dependent cell adhesion and their unique immunological characteristics and tissue localization. With the later immunological identification of N-cadherin, which was found to have a different tissue distribution than E-cadherin, it became apparent that a new family of $Ca^{2+}$-dependent cell-cell adhesion molecules had been discovered.

The molecular cloning of the genes encoding E-cadherin [see Nagafuchi et al., Nature, 329: 341–343 (1987)], N-cadherin [Hatta et al., J. Cell. Biol., 106: 873–881 (1988)], and P-cadherin [Nose et al., EMBO J., 6: 3655–3661 (1987)] provided structural evidence that the cadherins comprised a family of cell adhesion molecules. Cloning of L-CAM [Gallin et al., Proc. Natl. Acad. Sci. USA, 84: 2808–2812 (1987)] and uvomorulin [Ringwald et al., EMBO J., 6: 3647–3653 (1986)] revealed that they were identical to E-cadherin. Comparisons of the amino acid sequences of E-, N-, and P-cadherins showed a level of amino acid similarity of about 45%–58% among the three subclasses. Liaw et al., EMBO J., 9: 2701–2708 (1990) describes the use of PCR with degenerate oligonucleotides based on conserved regions of the E-, N- and P-cadherins to amplify N- and P-cadherin from a bovine microvascular endothelial cell cDNA.

The isolation by PCR of eight additional cadherins was reported in Suzuki et al., Cell Regulation, 2: 261–270 (1991). Subsequently, several other cadherins were described including R-cadherin [Inuzuka et al., Neuron, 7: 69–79 (1991)], M-cadherin [Donalies, Proc. Natl. Acad. Sci. USA, 88: 8024–8028 (1991)], B-cadherin [Napolitano, J. Cell. Biol., 113: 893–905 (1991)] and T-cadherin [Ranscht, Neuron, 7: 391–402 (1991)].

Additionally, proteins distantly related to cadherins such as desmoglein [Goodwin et al., Biochem. Biophys. Res. Commun., 173: 1224–1230 (1990) and Koch et al., Eur. J. Cell Biol., 53: 1–12 (1990)] and the desmocollins [Holton et al., J. Cell Science, 97: 239–246 (1990)] have been described. The extracellular domains of these molecules are structurally related to the extracellular domains of typical cadherins, but each has a unique cytoplasmic domain. Mahoney et al., Cell, 67: 853–868 (1991) describes a tumor suppressor gene of Drosophila, called fat, that also encodes a cadherin-related protein. The fat tumor suppressor comprises 34 cadherin-like subdomains followed by four EGF-like repeats, a transmembrane domain, and a novel cytoplasmic domain. The identification of these cadherin-related proteins is evidence that a large superfamily characterized by a cadherin extracellular domain motif exists.

Studies of the tissue expression of the various cadherin-related proteins reveal that each subclass of molecule has a unique tissue distribution pattern. For example, E-cadherin is found in epithelial cells while N-cadherin is found in neural and muscle cells. Expression of cadherin-related proteins also appears to be spatially and temporally regulated during development because individual proteins appear to be expressed by specific cells and tissues at specific developmental stages [for review see Takeichi (1991), supra]. Both the ectopic expression of cadherin-related proteins and the inhibition of native expression of cadherin-related proteins hinders the formation of normal tissue structure [Detrick et al., Neuron, 4: 493–506 (1990); Fujimori et al., Development, 110: 97–104 (1990); Kintner, Cell, 69: 225–236 (1992)].

The unique temporal and tissue expression pattern of the different cadherins and cadherin-related proteins is particularly significant when the role each subclass of proteins may play in vivo in normal events (e.g., the maintenance of the intestinal epithelial barrier) and in abnormal events (e.g., tumor metastasis or inflammation) is considered. Different subclasses or combinations of subclasses of cadherin-related proteins are likely to be responsible for different cell-cell adhesion events in which therapeutic detection and/or intervention may be desirable. For example, auto-antibodies from patients with pemphigus vulgaris, an autoimmune skin disease characterized by blister formation caused by loss of cell adhesion, react with a cadherin-related protein offering direct support for adhesion function of cadherins in vivo

[Amagai et al., *Cell*, 67: 869–877 (1991)]. Studies have also suggested that cadherins and cadherin-related proteins may have regulatory functions in addition to adhesive activity. Matsunaga et al., *Nature*, 334: 62–64 (1988) reports that N-cadherin has neurite outgrowth promoting activity. The Drosophila fat tumor suppressor gene appears to regulate cell growth and suppress tumor invasion as does mammalian E-cadherin [see Mahoney et al., supra; Frixen et al., *J. Cell. Biol.*, 113:173–185 (1991); Chen et al., *J. Cell, Biol.*, 114:319–327 (1991); and Vleminckx et al., *Cell*, 66:107–119 (1991)]. Thus, therapeutic intervention in the regulatory activities of cadherin-related proteins expressed in specific tissues may be desirable.

There thus continues to exist a need in the art for the identification and characterization of additional cadherin-related proteins which participate in cell-cell adhesion and/or regulatory events. Moreover, to the extent that cadherin-related proteins might form the basis for the development of therapeutic and diagnostic agents, it is essential that the genes encoding the proteins be cloned. Information about the DNA sequences and amino acid sequences encoding the cadherin-related proteins would provide for the large scale production of the proteins by recombinant techniques and for the identification of the tissues/cells naturally producing the proteins. Such sequence information would also permit the preparation of antibody substances or other novel binding molecules specifically reactive with the cadherin-related proteins that may be useful in modulating the natural ligand/antiligand binding reactions in which the proteins are involved.

SUMMARY OF THE INVENTION

The present invention provides cadherin-related materials and methods that are relevant to cell-cell adhesion. In one of its aspects, the present invention provides purified and isolated polynucleotides (e.g., DNA and RNA, both sense and antisense strands) encoding the novel cell adhesion molecules designated herein as protocadherins, including protocadherin-42, protocadherin-43, protocadherin pc3, protocadherin pc4 and protocadherin pc5. Preferred polynucleotide sequences of the invention include genomic and cDNA sequences as well as wholly or partially synthesized DNA sequences, and biological replicas thereof (i.e., copies of the sequences made in vitro). Biologically active vectors comprising the polynucleotide sequences are also contemplated.

Specifically illustrating protocadherin polynucleotide sequences of the present invention are the inserts in the plasmids pRC/RSV-pc42 and pRC/RSV-pc43 which were deposited with the American Type Culture Collection (ATCC), 12301 Parklawn Drive, Rockville, Md. 20852 on Dec. 16, 1992 and were assigned ATCC Accession Nos. 69162 and 69163, respectively.

The scientific value of the information contributed through the disclosures of the DNA and amino acid sequences of the present invention is manifest. For example, knowledge of the sequence of a partial or complete DNA encoding a protocadherin makes possible the isolation by standard DNA/DNA hybridization or PCR techniques of full length cDNA or genomic DNA sequences that encode the protein (or variants thereof) and, in the case of genomic DNA sequences, that specify protocadherin-specific regulatory sequences such as promoters, enhancers and the like. Alternatively, DNA sequences of the present invention may be chemically synthesized by conventional techniques. Hybridization and PCR techniques also allow the isolation of DNAs encoding heterologous species proteins homologous to the protocadherins specifically illustrated herein.

According to another aspect of the invention, host cells, especially eucaryotic and procaryotic cells, are stably transformed or transfected with the polynucleotide sequences of the invention in a manner allowing the expression of protocadherin polypeptides in the cells. Host cells expressing protocadherin polypeptide products, when grown in a suitable culture medium, are particularly useful for the large scale production of protocadherin polypeptides, fragments and variants thereby enabling the isolation of the desired polypeptide products from the cells or from the medium in which the cells are grown.

The novel protocadherin protein products of the invention may be obtained as isolates from natural tissue sources, but are preferably produced by recombinant procedures involving the host cells of the invention. The products may be obtained in fully or partially glycosylated, partially or wholly deglycosylated, or non-glycosylated forms depending on the host cell selected or recombinant production and/or post-isolation processing.

Protocadherin variants according to the invention may comprise polypeptide analogs wherein one or more of the specified amino acids is deleted or replaced or wherein one or more non-naturally encoded amino acids are added: (1) without loss, and preferably with enhancement, of one or more of the biological activities or immunological characteristics specific for a protocadherin; or (2) with specific disablement of a particular ligand/antiligand binding function. Also contemplated by the present invention are antibody substances (e.g., monoclonal and polyclonal antibodies, chimeric and humanized antibodies, antibody domains including Fab, Fab', F(ab')$_2$, Fv or single variable domains, and single chain antibodies) which are specific for the protocadherins of the invention. Antibody substances can be developed using isolated natural, recombinant or synthetic protocadherin polypeptide products or host cells expressing such products on their surfaces. The antibody substances may be utilized for purifying protocadherin polypeptides of the invention, for determining tissue expression of polypeptides and as antagonists of the ligand/antiligand binding activities of the protocadherins. Specifically illustrating monoclonal antibodies of the present invention are the protocadherin-43 specific monoclonal antibodies produced by the hybridoma cell line designated 3812C which was deposited with the ATCC on Dec. 2, 1992 and was assigned ATCC Accession No. HB 11207.

Numerous other aspects and advantages of the present invention will be apparent upon consideration of the following detailed description, reference being made to the drawing wherein FIG. 1A–C is an alignment of protocadherin amino acid sequences of the invention with the amino acid sequences of N-cadherin and of the Drosophila fat tumor suppressor.

BRIEF DESCRIPTION OF THE DRAWING

FIG. 1A–1C presents an alignment of the amino acid sequences of the deduced extracellular subdomains of PC42 (EC-1 through EC-7), PC43 (EC-1 through EC-6), mouse N-cadherin (EC-1 through EC-5) and drosophila fat EC-18. A sequence on a line in FIG. 1A continues on the same line in FIG. 1B and 1C.

DETAILED DESCRIPTION

The present invention is illustrated by the following examples wherein Examples 1, 2 and 3 describe the isolation by PCR of protocadherin polynucleotide sequences. Example 3 also describes the chromosome localization of several protocadherin genes of the invention. Example 4 describes the isolation by DNA/DNA hybridization of additional protocadherin polynucleotide sequences of the present invention. Example 5 presents the construction of expression plasmids including polynucleotides encoding protocadherin-42 or protocadherin-43 and the transfection of L cells with the plasmids. The generation of antibodies to protocadherin-42 and protocadherin-43 is described in Example 6. Example 7 presents the results of immunoassays of transfected L cells for the expression of protocadherin-42 or protocadherin-43. Example 8 describes the cell aggregation properties of L cells transfected with protocadherin-42, protocadherin-43 or a chimeric protocadherin-43/E-cadherin molecule. The calcium-binding properties of pc43 are described in Example 9. The results of assays of various tissues and cell lines for the expression of protocadherin-42 and protocadherin-43 by Northern blot, Western blot and in situ hybridization are respectively presented in Examples 10, 11 and 12. Example 13 describes immunoprecipitation experiments identifying a 120 kDa protein that coprecipitates with protocadherin-43.

EXAMPLE 1

The polymerase chain reaction (PCR) was used to isolate novel rat cDNA fragments encoding cadherin-related polypeptides.

Design of PCR Primers

Two regions of conserved amino acid sequence, one from the middle of the third cadherin extracellular subdomain (EC-3) and the other from the C-terminus of the fourth extracellular subdomain (EC-4), were identified by comparison of the published amino acid sequences for L-CAM (Gallin et al., supra), E-cadherin (Nagafuchi et al., supra), mouse P-cadherin (Nose et al., supra), uvomorulin (Ringwald et al., supra), chicken N-cadherin (Hatta et al., supra), mouse N-cadherin [Miyatani et al., *Science*, 245:631–635 (1989)] and human P-cadherin [Shimoyama et al., *J. Cell. Biol.*, 109:1787–1794 (1989)], and the corresponding degenerate oligonucleotides respectively set out below in IUPAC-IUB Biochemical nomenclature were designed for use as PCR primers.

Primer 1 (SEQ ID NO: 1)
5' AARSSNNTNGAYTRYGA 3'
Primer 2 (SEQ ID NO: 2)
3' TTRCTRTTRCGNGGNNN 5'

The degenerate oligonucleotides were synthesized using an Applied Biosystems model 380B DNA synthesizer (Foster City, Calif.).

Cloning of cDNA Sequences by PCR

PCR was carried out in a manner similar to that described in Suzuki et al., *Cell Regulation*, 2: 261–270 (1991) on a rat brain cDNA preparation. Total RNA was prepared from rat brain by the guanidium isothiocyanate/cesium chloride method described in Maniatis et al., pp. 196 in *Molecular Cloning: A Laboratory Manual*, Cold Spring Harbor, N.Y.: Cold Spring Harbor Laboratory (1982). Brain poly(A)$^+$ RNAs were then isolated using a FastTrack® kit (Invitrogen, San Diego, Calif.) and cDNA was prepared using a cDNA synthesis kit (Boehringer Mannheim Biochemicals, Indianapolis, Ind.). The PCR reaction was initiated by adding 2.5 units of Taq DNA polymerase (Boehringer Mannheim Biochemicals) to 100 ng template cDNA and 10 μg of each primer, after which 35 reaction cycles of denaturation at 94° C. for 1.5 minutes, annealing at 45° C. for 2 minutes, and polymerization at 72° C. for 3 minutes were carried out. Two major bands of about 450 base pairs (bp) and 130 bp in size were found when the products of the PCR reaction were subjected to agarose gel electrophoresis. The 450 bp band corresponded to the expected length between the two primer sites corresponding to the middle of the third cadherin extracellular subdomain (EC-3) and the carboxyl terminus of the fourth cadherin extracellular subdomain (EC-4), but the 130 bp band could not be predicted from any of the previously identified cadherin sequences. The 450 bp and 130 bp bands were extracted by a freezing and thawing method. The resulting fragments were phosphorylated at the 5' end with T4 polynucleotide kinase and subcloned by a blunt-end ligation into the Sma I site of M13 mp18 (Boehringer Mannheim Biochemicals) in a blunt end ligation for sequence analysis. Sequencing of the fragments was carried out by the dideoxynucleotide chain termination method using a Sequenase kit (United States Biochemicals, Cleveland, Ohio). DNA and amino acid sequence were analyzed using the Beckman Microgenie program (Fullerton, Calif.).

Analysis of cDNA Sequences

Nineteen novel partial cDNA clones were isolated. The DNA and deduced amino acid sequences of the clones (including sequences corresponding to the PCR primers) are set out as follows: RAT-123 (SEQ ID NOs: 3 and 4, respectively), RAT-212 (SEQ ID NOs: 5 and 6), RAT-214 (SEQ ID NOs: 7 and 8), RAT-216 (SEQ ID NOs: 9 and 10), RAT-218 (SEQ ID NOs: 11 and 12), RAT-224 (SEQ ID NOs: 13 and 14), RAT-312 (SEQ ID NOs: 15 and 16), RAT-313 (SEQ ID NOs: 17 and 18), RAT-314 (SEQ ID NOs: 19 and 20), RAT-315 (SEQ ID NOs: 21 and 22), RAT-316 (SEQ ID NOs: 23 and 24), RAT-317 (SEQ ID NOs: 25 and 26), RAT-321 (SEQ ID NOs: 27 and 28), RAT-323 (SEQ ID NOs: 29 and 30), RAT-336 (SEQ ID NOs: 31 and 32), RAT-352 (SEQ ID NOs: 33 and 34), RAT-411 (SEQ ID NOs: 35 and 36), RAT-413 (SEQ ID NOs: 37 and 38), and RAT-551 (SEQ ID NOs: 39 and 40).

The deduced amino acid sequences of the cDNA clones are homologous to, but distinct from the known cadherins. The cadherins described thus far have highly conserved, short amino acid sequences in the third extracellular subdomain (EC-3) including the consensus sequence D-Y-E or D-F-E located at the middle region of the subdomain and the consensus sequence D-X-N-E-X-P-X-F (SEQ ID NO: 41) or D-X-D-E-X-P-X-F (SEQ ID NO: 42) at its end (Hatta et al., supra), while the corresponding sequences of other subdomains, except for the fifth extracellular subdomain (EC-5), are D-R-E and D-X-N-D-N-X-P-X-F (SEQ ID NO: 43), respectively. In contrast, the deduced amino acid sequences of the new clones that correspond to cadherin extracellular subdomains include the sequence D-Y-E or D-F-E at one end, but have the sequence D-X-N-D-N-X-P-X-F instead of D-X-N-E-X-P-X-F or D-X-D-E-X-P-X-F, at the other end. The polypeptides encoded by the partial clones are homologous to previously identified cadherins but did not show significant homology to any other sequences in Genbank. Therefore, the partial cDNAs appear to comprise a new subclass of cadherin-related molecules.

EXAMPLE 2

Various cDNA fragments structurally similar to the rat cDNAs described in Example 1 were isolated from human, mouse, and Xenopus brain cDNA preparations and from Drosophila and *C. elegans* whole body cDNA preparations by PCR using Primers 1 and 2 as described in Example 1. The DNA and deduced amino acid sequences of the resulting PCR fragments (including sequences corresponding to the PCR primers) are set out as follows: MOUSE-321 (SEQ ID NOs: 44 and 45), MOUSE-322 (SEQ ID NOs: 46 and 47), MOUSE-324 (SEQ ID NOs: 48 and 49), MOUSE-326 (SEQ ID NOs: 50 and 51), HUMAN-11 (SEQ ID NOs: 52 and 53), HUMAN-13 (SEQ ID NOs: 54 and 55), HUMAN-21 (SEQ ID NOs: 56 and 57), HUMAN-24 (SEQ ID NOs: 58 and 59), HUMAN-32 (SEQ ID NOs: 60 and 61), HUMAN-42 (SEQ ID NOs: 62 and 63), HUMAN-43 (SEQ ID NOs: 64 and 65), HUMAN-212 (SEQ ID NOs: 66 and 67), HUMAN-213 (SEQ ID NOs: 68 and 69), HUMAN-215 (SEQ ID NOs: 70 and 71), HUMAN-223 (SEQ ID NOs: 72 and 73), HUMAN-410 (SEQ ID NOs: 74 and 75), HUMAN-443 (SEQ ID NOs: 76 and 77), XENOPUS-21 (SEQ ID NOs: 78 and 79), XENOPUS-23 (SEQ ID NOs: 80 and 81), XENOPUS-25 (SEQ ID NOs: 82 and 83), XENOPUS-31 (SEQ ID NOs: 84 and 85), DROSOPHILA-12 (SEQ ID NOs: 86 and 87), DROSOPHILA-13 (SEQ ID NOs: 88 and 89), DROSOPHILA-14 (SEQ ID NOs: 90 and 91) and C.ELEGANS-41 (SEQ ID NOs: 92 and 93). Comparison of the deduced amino acid sequences indicates significant similarity between sets of these clones. In particular, there are three sets of clones that appear to be cross-species homologues: RAT-218, MOUSE-322 and HUMAN-43; RAT-314, MOUSE-321 and HUMAN-11; and MOUSE-326 and HUMAN-42.

EXAMPLE 3

To ascertain the complete structure of the new proteins defined by the PCR products, two full length human cDNAs corresponding to the partial cDNAs HUMAN-42 and HUMAN-43 were isolated.

Isolation of Full-length Human cDNAs

A human fetal brain cDNA library (Stratagene, La Jolla, Calif.) in the λZapII vector was screened by the plaque hybridization method [described in Ausubel et al., Eds., *Current Protocols in Molecular Biology*, Sections 6.1.1 to 6.1.4 and 6.2.1 to 6.2.3, John Wiley & Sons, New York (1987)] with $^{32}$P-labelled HUMAN-42 and HUMAN-43 DNA fragments. The positive clones were plaque-purified and, using a helper virus, the inserts were cut out by an in vivo excision method in the form of a Bluescript SK(+) plasmid. The insert sequences were then subcloned into the M13 vector (Boehringer Mannheim, Biochemicals) for sequencing. Several overlapping cDNA clones were isolated with each probe including two cDNAs which contained the putative entire coding sequences of two novel proteins designated protocadherin-42 (pc42) and protocadherin-43 (pc43). The DNA and deduced amino acid sequences of pc42 are set out in SEQ ID NOs: 94 and 95, respectively, while the DNA and deduced amino acid sequences of pc43 are set out in SEQ ID NOs: 96 and 97, respectively.

A description of the cloning of protocadherin sequences of the invention was published in Sano et al., *The EMBO Journal*, 12(6): 2249–2256 (1993) after filing of the priority application hereto. The deduced amino acid sequence of pc43 was previously presented at the Dec. 9, 1991 meeting of the American Society for Cell Biology. An abstract of the presentation is published as Suzuki et al., *J. Cell. Biol.*, 115: 72a (Abstract 416) (Dec. 9, 1991).

Analysis of Full-length Human Clones

Comparison of the full length cDNA sequences of pc42 and pc43 to the sequences of the various DNA fragments originally obtained by PCR reveals that MOUSE-326 and HUMAN-42 correspond to a portion of the fourth extracellular subdomain (EC-4) of pc42, and RAT-314, MOUSE-321, and HUMAN-11 correspond to a portion of the third extracellular subdomain (EC-3) of pc43 and RAT-218, MOUSE-322 and HUMAN-43 correspond to a portion of the fifth extracellular domain (EC-5) of pc43.

The overall structures of pc42 and pc43 are similar to that of typical cadherins but the new molecules also have distinct features. Both protocadherin cDNA sequences contain putative translation initiation sites and translated amino acid sequences start with typical signal sequences, but the clones lack the prosequences that are present in all known cadherin precursors. The cDNAs encode proteins having a large N-terminal extracellular domain and a relatively short C-terminal cytoplasmic domain connected by a transmembrane sequence. The extracellular domains of pc42 and pc43 are different in length and pc42 contains seven subdomains that closely resemble the typical cadherin extracellular subdomain while pc43 has six such subdomains. The sizes of the protocadherin cytoplasmic domains are similar to those of typical cadherins, but the sequences do not show any significant homology with those of known cadherins or cadherin-related proteins.

Amino acid identity determinations between extracellular subdomains of human pc42 and pc43, and of mouse N-cadherin (SEQ ID NO: 98) (presented as an example of a "typical" cadherin) and the eighteenth extracellular subdomain of Drosophila fat tumor suppressor (EC-18, SEQ ID NO: 99) (the eighteenth extracellular subdomain of fat is a prototypical fat subdomain) are presented in Table 1 below, wherein, for example, "N-EC-1 x pc42" indicates that the first extracellular subdomain of N-cadherin was compared to the extracellular subdomain of pc42 indicated on the horizontal axis.

TABLE 1

|  | EC-1 | EC-2 | EC-3 | EC-4 | EC-5 | EC-6 | EC-7 |
|---|---|---|---|---|---|---|---|
| N-EC-1 × pc42 | 20 | 27 | 26 | 26 | 31 | 29 | 17 |
| N-EC-1 × pc43 | 31 | 23 | 23 | 26 | 31 | 24 |  |
| N-EC-2 × pc42 | 28 | 30 | 32 | 30 | 37 | 31 | 19 |
| N-EC-2 × pc43 | 30 | 28 | 30 | 36 | 29 | 30 |  |
| N-EC-3 × pc42 | 21 | 26 | 30 | 29 | 31 | 30 | 22 |
| N-EC-3 × pc43 | 25 | 18 | 26 | 28 | 28 | 25 |  |
| N-EC-4 × pc42 | 28 | 28 | 26 | 25 | 29 | 27 | 17 |
| N-EC-4 × pc43 | 21 | 25 | 28 | 28 | 29 | 24 |  |
| N-EC-5 × pc42 | 24 | 21 | 25 | 24 | 24 | 19 | 12 |
| N-EC-5 × pc43 | 15 | 21 | 20 | 20 | 25 | 16 |  |
| fat EC-18 × pc42 | 22 | 35 | 32 | 34 | 42 | 35 | 19 |
| fat EC-18 × pc43 | 32 | 30 | 36 | 36 | 33 | 29 |  |

The amino acid identity values between the extracellular subdomains of pc42 and pc43, and N-cadherin EC-1 through EC-5 and Drosophila fat EC-18 are mostly less than 40%. These identity values are comparable to the values between the subdomains of other cadherin subclasses. However, higher identity values indicate that pc42 and pc43 are more closely related to fat than to N-cadherin.

Amino acid identity determinations between extracellular subdomains of human pc42 and pc43 are presented in Table 2 below.

TABLE 2

| pc43 | pc42 | | | | | | |
|---|---|---|---|---|---|---|---|
|  | EC-1 | EC-2 | EC-3 | EC-4 | EC-5 | EC-6 | EC-7 |
| EC-1 | 33 | 27 | 29 | 26 | 25 | 26 | 25 |
| EC-2 | 26 | 38 | 29 | 33 | 34 | 28 | 21 |
| EC-3 | 26 | 32 | 41 | 30 | 32 | 31 | 22 |
| EC-4 | 25 | 34 | 30 | 41 | 39 | 31 | 18 |

TABLE 2-continued

| | pc42 | | | | | | |
|---|---|---|---|---|---|---|---|
| pc43 | EC-1 | EC-2 | EC-3 | EC-4 | EC-5 | EC-6 | EC-7 |
| EC-5 | 23 | 32 | 29 | 27 | 36 | 34 | 16 |
| EC-6 | 25 | 25 | 26 | 25 | 28 | 23 | 26 |

The identity values between respective EC-1, EC-2, EC-3, EC-4, EC-5 subdomains and the last subdomains of pc42 and pc43 are generally higher values than values obtained for comparisons of the protocadherins to N-cadherin. These results suggest that pc42 and pc43 are more closely related to one another than they are to classic cadherins.

FIG. 1A–C presents an alignment of the deduced amino acid sequences of the extracellular subdomains of pc42 (EC-1 through EC-7) (amino acids 42–818 of SEQ ID NO: 95), pc43 (EC-1 through EC-6) (amino acids 29–688 of SEQ ID NO: 97), mouse N-cadherin (EC-1 through EC-5) (amino acids 1–557 of SEQ ID NO: 98) and Drosophila fat EC-18 (SEQ ID NO: 99). A sequence on a line in FIG. 1A continues on the same line in FIGS. 1B and 1C. Gaps were introduced to maximize homology. In FIG. 1A–C, the position at which an amino acid appears in a SEQ ID NO is indicated in parenthesis. For example, in FIG. 1A the first amino acid of EC1 of protocadherin-43 is an alanine which appears at position 29 in SEQ ID NO: 97 and the last amino acid of the protocadherin-43 EC1 appearing in FIG. 1A is an alanine which appears at position 63 in SEQ ID NO: 97. The amino acid residues described by capital letters in the "motif" line are present in more than half of the subdomains of N-cadherin, pc42, pc43 and Drosophila fat. The amino acid residues described by small letters in the motif line are less well conserved in human pc42, pc43, and Drosophila fat. FIG. 1A–C shows that many amino acids characteristic of other cadherin extracellular domain repeats are conserved in the pc42 and pc43 sequences, including the cadherin sequence motifs DXD, DRE and DXNDNXPXF (SEQ ID NO: 43), two glycine residues, and one glutamic acid residue. Additionally, pc42 and pc43 share unique features in comparison to N-cadherin. More amino acids at specific sites are conserved between pc42 and pc43, such as the DXDXGXN (SEQ ID NO: 100) protocadherin sequence motif near the amino terminus of the pc42 and pc43 subdomains and the AXDXGXP (SEQ ID NO: 101) sequence motif near the carboxyl terminus of the subdomains. Additionally, both protocadherins share regions that do not show significant homology with the typical cadherin motif (of N-cadherin) near the carboxyl terminus of EC-1, in the middle of EC-2 and EC-4, and at the carboxyl terminus of the last repeat. A cysteine residue is located at a similar position in the middle of EC-4 of pc42 and pc43. In general, the extracellular subdomains of pc42 and pc43 are more similar to EC-18 of fat than the extracellular subdomains of N-cadherin.

Possible Alternative Splicing

Sequence analysis of various overlapping protocadherin cDNA clones revealed that some clones contained unique sequences at the 3' end, although the 5' end sequences were identical to other clones. The sequences forming the boundaries of the 3' end regions are consistent with the consensus sequence of mRNA splicing, suggesting that these clones may correspond to alternatively spliced mRNAs. The DNA and deduced amino acid sequences of one possible product of alternative splicing of pc42 mRNA are set out in SEQ ID NOs: 102 and 103. The DNA and deduced amino acid sequences of two possible products of alternative splicing of pc43 mRNA are respectively presented in SEQ ID NO: 104 and 105, and SEQ ID NOs: 106 and 107.

Chromosome Localization

The chromosomal location of the protocadherin 413 gene (SEQ ID NO: 37) and of the pc42 and pc43 genes was determined by conventional methods.

Briefly, C3H/HeJ-gld and *Mus spretus* (Spain) mice and [(C3H/HeJ-gld x *Mus spretus*) $F_1$ x C3H/HeJ-gld] interspecies backcross mice were bred and maintained as previously described in Seldin, et al., *J. Exp. Med.*, 167: 688–693 (1988). *Mus spretus* was chosen as the second parent in the cross because of the relative ease of detection of informative restriction fragment length variants (RFLVs) in comparison with crosses using conventional inbred laboratory strains. Gene linkage was determined by segregation analysis.

Genomic DNA isolated from mouse organs by standard techniques was digested with restriction endonucleases and 10 μg samples were electrophoresed in 0.9% agarose gels. DNA was transferred to Nytran membranes (Schleicher & Schull, Inc., Keene, N.H.), hybridized with the appropriate probe at 65° C. and washed under stringent conditions, all as previously described in Maniatis et al., supra). To localize the pc42 gene, a mouse sequence probe corresponding to nucleotides 1419 to 1906 of SEQ ID NO: 94 was used and for pc43 a rat sequence probe corresponding to nucleotides 1060 to 1811 of SEQ ID NO: 96 was used. To localize the procadherin 413 gene, a probe including the sequence set out in SEQ ID NO: 37 was used. Other clones used as probes in the current study and RFLVs used to detect anonymous DNA loci were all previously described [Chromosome 7, DNA segment, Washington 12 (D7Was12); the parathyroid hormone (Pth); calcitonin (Calc); hemoglobin, β chain (Hbb); metallothionein-I (Mt–1); adenine phosphoribosyltransferase (Aprt); growth hormone receptor (Ghr); prostaglandin E receptor EP2 subtype (Ptgerep2); dihydrofolate reductase-2 (Dhfr2); fibroblast growth factor a (Fgfa); and glucocorticoid receptor-1 (Grl–1)].

Comparison of the haplotype distribution of protocadherin genes with those determined for loci throughout the mouse genome allowed each to be mapped to specific regions of mouse chromosomes. The probability for linkage was>99% and indicated assignment of both the pc42 gene and the pc43 gene was chromosome 18. The assignment of the protocadherin 413 gene was chromosome 7. The region of chromosome 18 to which the pc42 and pc43 genes were mapped corresponds to the ataxia (ax) loci [Burt, Anat. Rec., 196: 61–69 (1980) and Lyon, *J. Hered.*, 46: 77–80 (1955)] and twirler (7w) loci [Lyon, *J. Embryol. Exp. Morphol.*, 6: 105–116 (1958)], while the region of chromosome 7 to which the protocadherin 413 gene was mapped corresponds to the shaker (sh-1) locus [Kikuchi et al., *Acta Oto-Laryngol.*, 60: 287–303 (1965) and Lord et al., *Am. Nat.*, 63: 453–442 (1929)]. These loci have been implicated as involved in hereditary neural disease in the mouse. This result is consistent with in situ hybridization results (see Example 12) showing that pc42 and pc43 are strongly expressed in the brain and particularly in the cerebellum.

EXAMPLE 4

Two additional novel human protocadherin cDNAs and one additional novel rat protocadherin cDNA were isolated using rat protocadherin fragments described in Example 1 as probes.

Initially, the rat clone RAT-214 (SEQ ID NO: 7) was used as a probe to screen a rat brain cDNA library (Stratagene, La Jolla, Calif.). The final washing step was performed twice at 50° C. in 0.1×SSC with 0.1% SDS for 15 minutes. Various clones were identified which contained partial cDNA inserts encoding related protocadherin amino acid sequences. The nucleotide sequence of one novel rat clone designated #6-2 is set out in SEQ ID NO: 108. The first fifteen nucleotides of SEQ ID NO: 108 are the sequence of a linker and are not part of the rat #6-2 clone.

A human fetal brain cDNA library obtained from Stratagene was screened with the 0.7 kbp PstI fragment of clone #6-2. The fragment appears to encode the EC-2 and EC-3 of the rat protocadherin. After screening about $2\times10^6$ phages, eleven positive clones were isolated. Sequencing of the clones identified a novel full length human protocadherin cDNA designated human pc3. The nucleotide and deduced amino acid sequence of human pc3 are set out in SEQ ID NOs: 109 and 110.

The 0.7 kbp PstI fragment of rat clone #6-2 was also used to rescreen the Stratagene rat brain cDNA library for full length rat cDNA clones. A clone containing an insert encoding a full length novel protocadherin cDNA was isolated. The DNA and deduced amino acid sequence of the insert are set out in SEQ ID NO: 111 and 112. The full length rat cDNA was named pc5 because it does not appear to be the homolog of the human pc3 clone based upon a comparison of the sequences.

Concurrently, the 0.8 kbp Eco RI-Pst I fragment of partial rat cDNA designated #43 (SEQ ID NO: 113), which was obtained by screening the Stratagene rat brain cDNA library with a probe corresponding to the human pc43 cytoplasmic domain, was used to probe the Stratagene human cDNA library for full length human protocadherin cDNAs. The fragment appears to encode EC-3 through the beginning of EC-6 of clone #43. One partial clone identified encodes a novel human protocadherin named human pc4. The nucleotide sequence and deduced amino acid sequences of the human pc4 clone are set out in SEQ ID NOs: 114 and 115. The amino acid sequence encoded by the pc4 clone appears to begin in the middle of EC-2 of pc4 and continues through the cytoplasmic tail of the protocadherin.

EXAMPLE 5

The full length human cDNAs encoding pc42 and pc43 were expressed in L cells (ATCC CCL 1) using the pRC/RSV expression vector (Invitrogen, San Diego, Calif.). The cDNAs were isolated from the Bluescript SK(+) clones described in Example 2 by digestion with SspI followed by blunt-ending with DNA polymerase and digestion with XbaI (for pc42), or by double digestion with SpeI and EcoRV (for pc43). The pRC/RSV expression vector was digested with HindIII, followed by blunt-ending and re-digestion with XbaI for insertion of pc42 sequences, or by digested with XbaI followed by blunt-ending and re-digestion with SpeI for insertion of pc43 sequences. The isolated protocadherin DNAs were ligated into the linearized pRC/RSV vector. The resulting pc42 expression plasmid designated pRC/RSV-pc42 (ATCC 69162) and pc43 expression plasmid designated pRC/RSV-pc43 (ATCC 69163) were purified by CsCl gradient centrifugation and transfected into L cells by a Ca-phosphate method.

The pc42 and pc43 transfectants were morphologically similar to the parental cells. Northern blot analysis of L cells transfected with pc42 or pc43 DNA sequences showed that the transfected cells expressed mRNAs of a size expected to encode the particular protocadherin.

EXAMPLE 6

Rabbit polyclonal antibodies specific for pc42 and pc43 were generated as well as a mouse monoclonal antibody specific for pc43.

Preparation of Polyclonal Antibodies Specific for pc42 and pc43

DNA sequences encoding portions of the extracellular domain of pc42 and pc43 were each fused to a maltose binding protein-encoding sequence and expressed in bacteria. Specifically, DNAs corresponding to EC-4 through EC-7 of pc42 and EC-3 through EC-5 of pc43 were prepared by PCR and subcloned in the correct reading frame into the multicloning site of the pMAL expression vector (New England Biolabs, Beverly, Mass.) which contains sequences encoding maltose binding protein immediately upstream of the multicloning site. The resulting plasmids were then introduced into *E. coli* NM522 cells (Invitrogen, San Diego, Calif.) by a single step transformation method. Expression of the fusion proteins was induced by the addition of IPTG and the fusion proteins were purified from cell extracts by amylose resin affinity chromatography (New England Biolabs) as described by the manufacturer. The fusion proteins were used for the immunization of rabbits without further purification.

Polyclonal antibodies were prepared in rabbits by immunization at four subcutaneous sites with 500 μg of purified fusion protein in Freund's complete adjuvant. Subsequent immunizations with 100 μg of the fusion protein were in Freund's incomplete adjuvant. Immune sera was passed through sepharose coupled to maltose binding protein (New England Biolabs) and polyclonal antibodies were purified from immune sera using Sepharose affinity columns prepared by reaction of the purified fusion protein with CNBr Sepharose (Pharmacia). Reactivity of the polyclonal sera with purified pc42 fusion protein and pc42 transfected cell extracts (described in Example 5) was confirmed.

Preparation of Monoclonal Antibodies Specific for pc43

The pc43 fusion protein (containing the EC-3 through EC-5 subdomains of pc43) was used to generate monoclonal antibodies in mice according to the method of Kennett, *Methods in Enzymol.*, 58:345–359 (1978). Briefly, mice were immunized with the pc43 fusion protein (100 μg) at two subcutaneous sites. The spleen from the highest titer mouse was fused to the NS1 myeloma cell line. The resulting hybridoma supernatants were screened in a ELISA assay for reactivity with the pc43 fusion protein and with maltose binding protein. The fusion wells with the highest reactivity to the pc43 extracellular domains were subcloned. The hybridoma cell line designated 38I2C (ATCC HB 11207) produced a $IgG_1$ subtype monoclonal antibody specific for pc43. Reactivity of the monoclonal antibody produced by hybridoma cell line 38I2C to pc43 was confirmed by immunoblotting the pc43 L cell transfectants described in Example 5. The 38I2C monoclonal antibody is specific for human pc43.

EXAMPLE 7

L cells transfected with DNA sequences encoding pc42 and pc43 as prepared in Example 5 were assayed for expression of the protocadherins by immunoblot and by immunofluorescence microscopy.

Immunoblot Analysis

Cell extracts of pc42 and pc43 transfectants were subjected to SDS-PAGE and then blotted electrophoretically onto a PVDF membrane (Millipore, Bedford, Mass.). The membranes were incubated with 5% skim milk in Tris-buffered saline (TBS) for two hours and then respectively with either pc42 polyclonal sera or pc43 monoclonal antibody for one hour. The membranes were washed three times (for 5 minutes each wash) with TBS containing 0.05% Tween 20 and respectively incubated with alkaline phosphatase-conjugated anti-rabbit IgG antibody or anti-mouse IgG antibody (Promega, Madison, Wis.) in the same buffer for one hour. After washing the membranes with TBS containing 0.05% Tween 20, reactive bands were visualized by using Western Blue solution (Promega).

Anti-pc42 polyclonal antibodies stained a band of about 170 kDa molecular weight in pc42 transfected cells, but not parental L cells. The pc43-specific monoclonal antibody (3812C) and polyclonal antibodies stained two adjacent bands of about 150 kDa molecular weight in pc43 transfected cells. The pc43 antibodies did not stain bands in parental L-cells. The molecular weights indicated by the staining of bands by the pc42 and pc43 antibodies are significantly larger than the molecular weights predicted from the deduced amino acid sequences. This discrepancy in molecular weight is common among various cadherin-related proteins and may be attributable to the glycosylation and/or cadherin specific structural properties. The pc42 antibody also stained smaller bands, which may be proteolytic degradation products.

When transfected cells were trypsinized and cell extracts were prepared, run on SDS/PAGE and immunoblotted with the appropriate antibody, the pc42 and pc43 polypeptides expressed by the transfected cells were found to be highly sensitive to proteolysis and were easily digested by 0.01% trypsin treatment. In contrast to the classic cadherins, however, these proteins were not protected from the digestion in the presence of 1–5 mM $Ca^{2+}$.

Immunofluorescence Microscopy

Transfected cells were grown on a cover slip precoated with fibronectin and were fixed with 4% paraformaldehyde for 5 minutes at room temperature or with cold methanol on ice for 10 minutes followed by 4% paraformaldehyde fixation. After washing with TBS, the cells were incubated with TBS containing 1 % BSA for 30 minutes and then with anti-pc42 polyclonal antibody or anti-pc43 monoclonal antibody in TBS containing 1 % BSA for 1 hour at room temperature. Cover slips were then washed with TBS containing 0.01 % BSA and respectively incubated with FITC-conjugated anti-rabbit antibody or anti-mouse antibody (Cappel, Durham, N.C.) for 60 minutes at room temperature. The cells were washed again with TBS containing 0.01 % BSA and subjected to fluorescence microscopy. Both pc42-specific and pc43-specific polyclonal antibodies stained the cell periphery of transfected cells expressing the protocadherin proteins, mainly at the cell-cell contact sites. The antibodies did not stain the parent L cells, nor did rabbit preimmune sera stain the pc42 and pc43 transfectants.

EXAMPLE 8

The cell aggregation properties of the transfected L cells expressing protocadherin proteins were examined. Transfected L cells were cultured in Dulbecco's Modified Eagles Medium (DMEM) (Gibco, Grand Island, N.Y.) supplemented with 10% fetal bovine serum at 37° C. in 5% $CO_2$. Cells grown near confluence were treated with 0.01 % trypsin in the presence of 1 mM EGTA for 25 minutes on a rotary shaker at 37° C. and collected by centrifugation. The cells were washed three times with $Ca^{2+}$ free HEPES-buffered saline (HBS) after adding soybean trypsin inhibitor, and were resuspended in HBS containing 1% BSA. The cell aggregation assay [Urushihara et al., Dev. Biol., 70: 206–216 (1979)] was performed by incubating the resuspended cells in a 1:1 mixture of DMEM and HBS containing 1% BSA, 2 mM $CaCl_2$ and 20 µg/ml of deoxyribonucelease on a rotary shaker at 37° C. for 30 minutes to 6 hours.

The pc42 and pc43 transfectants did not show any significant cell aggregation activity during periods of incubation less than 1 hour. This is in contrast to the cell aggregation that occurs with classic cadherins in similar experiments (Nagafuchi et al., supra, and Hatta et al., supra). However, prolonged incubation of transfected cells (more than 1–2 hours) resulted in gradual re-aggregation of the cells into small aggregates. Similar results were obtained when single cell suspensions of transfected cells were prepared by trypsin treatment in the presence of $Ca^{2+}$. No re-aggregation was observed under the same conditions when untransfected L cells or L cells transfected with pRC/RSV vector alone were tested. When pc43 transfectants labelled with DiO (Molecular Probes, Eugene, Oreg.) were incubated with unlabelled pc42 transfectants in the cell aggregation assay, aggregation of labelled and unlabelled cells was almost mutually exclusive indicating that protocadherin binding is homophilic.

In view of the fact that the protocadherin cytoplasmic domains exhibit no apparent homology to cadherin domains, experiments were performed to determine if the difference in cytoplasmic domains could account for the difference in cell aggregation activity observed in cadherin and protocadherin transfectants. The cytoplasmic domain of pc43 was replaced with the cytoplasmic domain of E-cadherin and aggregation of cells transfected with the chimeric construct was analyzed.

The Bluescript SK(+) clone described in Example 2 which contained the entire coding sequence for pc43 was digested with EcoRV and then partially digested with XbaI to remove the sequence corresponding to the cytoplasmic domain, and the plasmid DNA was purified by agarose gel electrophoresis. The cDNA corresponding to the cytoplasmic domain of mouse E-cadherin was synthesized by PCR using mouse cDNA made from mouse lung mRNA as a template and specific primers corresponding to a region near the N-terminus of the cytoplasmic domain sequence or the region containing the stop codon of mouse E-cadherin (Nagafuchi et al., supra). A XbaI sequence was included to the 5' end of the upstream primer. The E-cadherin cytoplasmic domain cDNA was then subcloned into the linearized pc43 Bluescript clone. The DNA containing the entire resulting chimeric sequence was cut out with SpeI and EcoRV and was subcloned into the SpeI-blunted XbaI site of the expression vector pRc/RSV vector. Finally, L cells were transfected with the resultant construct by a calcium phosphate method. After screening with G418 for about 10 days, the transfectants were stained with FITC-labeled 3812C anti-pc43 antibody and subjected to FACS analysis. A portion of highly labeled cells were isolated and cloned. Transfectants showed a morphology similar to that of parental L cells and the expressed protein was localized at the cell periphery using pc43 antibody for immunofluorescence microscopy.

Cell aggregation activity of the chimeric transfectants was analyzed as follows. The chimeric pc43 transfectants were labeled with DiO for 20 minutes at room temperature. The resultant cells were trypsinized in the presence of 1 mM EGTA and single cell suspension was made. Then, the cells were mixed with unlabeled other type of transfectants and incubated on a rotary shaker for two hours. The results were examined with a fluorescence and a phase contrast microscope apparatus. Antibody inhibition of cell aggregation was examined by incubation of the transfectants in the presence of polyclonal anti-pc43 antibody (100 ng/ml) in the standard assay medium.

In the cell aggregation assay, the chimeric pc43 transfectants showed clear $Ca^{2+}$-dependent cell aggregation within forty minutes of incubation. Cell aggregation was inhibited by the addition of pc43-specific polyclonal antibody.

EXAMPLE 9

The procedures of Maruyama et al., *J. Biochem.*, 95: 511–519 (1984) were used to determine the calcium binding properties of pc43 by Western blot analysis in the presence or absence of calcium-45. The pc43 fusion protein described in Example 6 containing pc43 subdomains EC-3 through EC-5 was compared to the calcium binding protein calmodulin. Samples of purified pc43 fusion protein were run on SDS/PAGE and electrophoretically transferred to PVDF membrane. Binding of the $^{45}Ca^{2+}$ to the pc43 fusion protein was detected by autoradiography and was determined to be nearly as efficient as binding of $^{45}Ca^{2+}$ to calmodulin. In contrast, there was no binding of calcium to purified maltose binding protein lacking the pc43 extracellular domain. The pc43 subdomains EC-3 through EC-5 contain sequences highly homologous to the putative $Ca^{2+}$ binding motifs found in E-cadherin. [See, Ringwald et al., *EMBO J.*, 6: 3647–3653 (1987).]

EXAMPLE 10

The expression of mRNA encoding pc42 and pc43 was assayed in various tissues and cell lines by Northern blot.

Total RNAs were prepared by the guanidium isothiocyanate method and poly(A)+ RNAs were isolated using a FastTrack kit (Invitrogen). RNA preparations were electrophoresed in a 0.8% agarose gel under denaturing conditions and transferred onto a nitrocellulose filter using a capillary method. Northern blot analyses were performed according to the method of Thomas, *Proc. Natl. Acad. Sci. USA*, 77: 5201–5205 (1980). The final wash was in 0.2× standard saline citrate containing 0.1% sodium dodecyl sulfate at 65° C. for 10 minutes.

Protocadherin mRNA Expression in Adult Rat Tissues

Total mRNA preparations of rat tissues including brain, heart, liver, lung, skin, kidney and muscle were separated electrophoretically under denaturing conditions (10 µg mRNA/lane) and transferred onto nitrocellulose filters. The filters were hybridized with $^{32}$P-labelled cDNA fragments MOUSE-326 (which corresponds to EC-4 of human pc42) and RAT-218 (which corresponds to EC-5 of human pc43). The mRNAs of both protocadherins were highly expressed in brain. The pc42 probe detected a major band of 7 kb and a minor band of 4 kb in size, possibly representing the products of alternative splicing. The pc43 probe hybridized to a major band of 5 kb in size and with minor bands of smaller sizes.

Developmental Expression of Protocadherin mRNA in Rat Brain

To examine the developmental regulation of mRNA expression of the protocadherins, brain mRNA from rats at embryonic days 17 and 20, neonatal days 5 and 11 and from adult rats was prepared and subjected to Northern blot analysis as described above for other rat tissues. β-actin was used as an internal standard. mRNA levels for pc42 and pc43 proteins increased during embryonic development of the brain as compared with β-actin expression.

Protocadherin mRNA Expression in Human Cell Lines

Several neuronal and glial cell lines (including human SK-N-SH neuroblastoma, human U251 glioma, and mouse Neuro-2a neuroblastoma cell lines) were assayed by Northern blot using $^{32}$P-labelled for expression of pc42 and pc43 mRNA. Human cell lines were probed with HUMAN-42 (which corresponds to EC-4 of human pc42) and HUMAN-43 (which corresponds to EC-5 of human pc43) cDNA fragments while the mouse cell line was probed with MOUSE-326 (which corresponds to EC-4 of human pc42) and RAT-322 (which corresponds to EC-5 of human pc43) cDNA fragments. SK-N-SH human neuroblastoma cells and U251 human glioma cells were found to express pc43 mRNA and Neuro-2a mouse neuroblastoma cells were found to express pc42 mRNA.

EXAMPLE 11

Expression of pc43 protein in various tissues, extracts and cells was assayed by Western blot and immunofluorescence microscopy.

Expression in Rat Cardiac Muscle Extracts

A rat heart non-ionic detergent extract was prepared by freezing a heart in liquid nitrogen after removal, powdering in a mortar and pestle, grinding briefly in a polytron in 0.5% Nonidet P40 in [10 mM PIPES (pH 6.8), 50 mM NaCl, 250 mM $NH_4SO_4$, 300 mM sucrose, 3 mM $MgCl_2$] and microfuging for 15 minutes. Samples were separated by SDS/PAGE and electrophoretically transferred to nitrocellulose (Towbin et al., *PNAS* 76:4350–4354, 1979). Two pc43 protein bands with molecular weights of 150 KDa and 140 KDa were detected with rabbit polyclonal antibodies to pc43 by the immunoblot method described in Example 7.

Expression in Tissue Sections and Cells

To determine the localization of the protocadherins in various tissues, human and rat adult tissues were removed, incubated in 30% sucrose in PBS for 30 minutes at 4° C., embedded in OCT compound (Tissue-Tek, Elkhart, Ind.) in cryomolds and quickly frozen. Six micron sections were cut and placed on glass slides. The slides were washed with PBS and fixed in 3% p-formaldehyde for 5 minutes. To permeablize the tissue sections, the slides were immersed in −20° C. acetone for 10 minutes and air dried. The sections were blocked with 2% goat serum and 1% BSA in PBS for 30 minutes and then incubated with the rabbit anti-pc43 polyclonal antisera for 1 hour at room temperature. The sections were rinsed 3 times in PBS containing 0. 1% BSA and incubated with a biotinylated anti-rabbit (Vector Laboratories, Burlingame, Calif.) in 1 % BSA in PBS for 30 minutes. After rinsing 3 times, strepavidin-conjugated with FITC (Vector Laboratories) was added for 30 minutes and again washed 3 times. For co-localization studies, an appropriate primary antibody was used with a TRITC-conjugated secondary antibody.

A. Muscle

Immunolocalization of pc43 in rat cardiac muscle shows that pc43 is localized in a repeating pattern which is consistent with pc43 being associated with the sarcomeres. Sarcomeres are repetitive contractile units between the *fascia adherens* in skeletal and cardiac muscle. Co-localization with cytoskeletal proteins shows that pc43 is present at the ends of the sarcomeres in the Z lines which are associated with desmin and the actin-binding protein vinculin, and alpha-actinin. The thin microfilaments of F-actin are associated with the thick myosin filaments between the Z lines. In contrast, N-cadherin is localized at the ends of cardiac myocytes at the *fascia adherens* junctions at sites of mycocyte:myocyte contact. The localization of pc43 in cardiac muscle suggests that pc43 may play a role in muscle contraction in the anchoring of the contractile apparatus to the plasma membrane.

Similar localization for pc43 was observed in rat skeletal muscle. Ultrastructural studies have shown that dystrophin, the gene product lacking in Duchenne muscular dystrophy, is a component of the sarcolemma [Porter et al., *J. Cell. Biol.*, 117:997–1005 (1992)]. The sarcolemma is connected to the contractile apparatus at the M and Z lines where pc43 is localized.

17

B. Brain

Reactivity of anti-pc43 polyclonal antibody and monoclonal antibody 38I2C on frozen sections of rat and human cerebellum, respectively, shows that the major sites of pc43 expression are located in Purkinje cells and the granule cell layer which contains numerous small neurons.

C. Placenta

Strong reactivity of monoclonal antibody 38I2C with human syncytiotrophoblasts was also observed in development of the placenta at an early state (5–7 weeks of gestation). Expression appeared to gradually decrease as the stage progressed indicating that pc43 may be involved in the implantation of fertilized eggs into the placenta.

D. Neuroblastoma and Astrocytoma Cells

Immunocytochemical localization of pc43 in Sk-N-SH neuroblastoma cells and UW28 astrocytoma cells using anti-pc43 antibodies reveals a punctate cell surface distribution of pc43 and in some cells there is a localization at the tips of extensions of neuronal foot processes. At sites of cell-cell contact of UW28 astrocytoma cells, pc43 is organized in a series of parallel lines. The lines start at the contact site and extend approximately 5 micron. F-actin microfilaments were identified with rhodamine-phalloidin (Molecular Probes, Eugene, Oreg., as described by the manufacturer) showing that the microfilaments in the cell appear to end in the pc43 linear structures which extend from the edge of the cell at sites of cell contact.

Immunoblotting studies with pc43 specific antibodies show that a protein with a molecular weight of 140 kDa is recognized in human Sk-N-SH neuroblastoma cells and in UW28 astrocytoma cells.

E. Osteoblasts

Immunocytochemical localization of pc43 using monoclonal antibody 38I2C in tow human ostogenic sarcoma cell lines [SaOS (ATCC HTB 85) and MG-63 (ATCC CRL 1427)] and in cultures of normal human trabecular osteoblasts [culture system described in Civitelli et al., *J. Clin. Invest.*, 91: 1888–1896 (1993)] showed that pc43 is expressed in osteoblasts in a pattern similar to that seen in UW28 astrocytoma cells. At sites of cell-cell contact, pc43 is organized in a series of parallel lines that appear to correspond to the actin stress fibers. In addition, in some cells, pc43 appears to localize at the tips of contacting cell processes. Northern blot analysis provides additional evidence that pc43 is expressed in normal human trabecular osteoblasts. A pc43 specific DNA probe hybridized to a major band of 5 kb in samples of poly-A mRNA isolated from normal human trabecular osteoblasts.

EXAMPLE 12

In situ hybridization experiments using protocadherin specific RNA probes were performed on cryosections of rat tissue.

Sense and antisense $^{35}$S-riboprobes were made using the standard procedure described by Promega (Madison, Wis.). An approximately 400 bp EcoRI-XbaI fragment of the MOUSE-326 cDNA clone was used as a pc42 specific probe. This fragment encodes the middle of EC-3 to the end of EC-4 of pc42. An approximately 700 bp SmaI fragment of the RAT-218 cDNA clone was used as a pc43 specific probe. The fragment encodes the end of EC-3 to the end of EC-5 of pc43.

Rat adult tissues were harvested and immediately embedded with OCT Compound (Tissue-Tek) in cryomolds and quickly frozen in a bath of 95% ethanol/dry ice. The frozen blocks were stored at −80° C. until cut. Six micron tissue sections were cut using a cryostat (Reichert-Jung, Model

18

2800 Frigocut N, Leica, Inc., Gilroy, Calif.). Cut tissue sections were stored at −80° C.

The in situ protocol used was a variation of that described by Angerer et al., *Methods in Enzymology*, 152: 649–660, (1987). All solutions were treated with diethylpyrocarbonate (DEPC, Sigma, St. Louis, Mo.) to remove RNase contamination. The tissue sections were first fixed in 4% paraformaldehyde at 4° C. for 20 minutes. To remove excess paraformaldehyde and stop the tissue fixation, the slides were washed in PBS (phosphate buffered saline), denatured in a graded series of alcohols (70, 95, 100%) and then dried. To prevent the tissue from detaching from the glass slide during the in situ procedure, the tissue sections were treated in a poly-L-lysine solution (Sigma) at room temperature for 10 minutes. To denature all RNA in the tissue, the sections were placed in a solution of 70% formamide/2×SSC (0.15M NaCl/0.3M Na citrate, pH 7.0) at 70° C. for 2 minutes after which they were rinsed in chilled 2×SSC, dehydrated in a graded series of alcohols and then dried. Once dried, the sections were prehybridized in hybridization buffer [50% formamide/50 mM DTT (dithiothrietol)/0.3M NaCl/20 mM Tris, pH 8.0/5 mM EDTA/1× Denhardt's (0.02% Ficoll Type 400/0.02% polyvinylpyrrolidone/0.02% BSA)/10% Dextran Sulfate] at the final hybridization temperature for approximately 4 hours. After prehybridization, approximately $1×10^6$ cpm of the appropriate riboprobe was added to each section. The sections were generally hybridized at 45° C. overnight (12–16 hours). To insure that the hybridization seen was specific, in some experiments the hybridization stringency was increased by raising the hybridization temperature to 50° C. As both the 45° C. and 50° C. experiments gave comparable results, the standard hybridization temperature used was 45° C.

To remove excess, nonhybridized probe, the sections were put through a series of washes. The sections were first rinsed in 4×SSC to remove the bulk of the hybridization solution and probe. Next a 15 minute wash in 4×SSC/50 mM DTT was carried out at room temperature. Washes at increased stringencies were also utilized. A 40 minute wash in 50% formamide/2×SSC/50 mM DTT was performed at 60° C. Four final room temperature washes were carried out for 10 minutes each: two in 2×SSC and two in 0.1×SSC. The washed slides were dehydrated in a graded series of alcohols and dried.

To visualize the hybridized probe, the slides were dipped in Kodak NTB2 nuclear emulsion (International Biotechnology, New Haven, Conn.) which had been diluted 1:1 in $dH_2O$. Once dry, the slides were stored at 4° C. in light-tight boxes for the appropriate exposure time. The in situ slides were independently viewed by two persons and scored positive or negative for hybridization signal.

All in situ hybridization studies were performed on rat tissue. Because results from Northern blot experiments (see Example 9) indicated that both pc42 and pc43 are expressed in adult brain, in situ hybridization studies were carried out to localize the expression of these molecules to specific brain cell types. Hybridization seen in the normal adult rat brain was specific (no background hybridization was seen with the sense probes) and was localized to specific regions in the brain. The overall pattern of expression seen for pc42 and pc43 was very similar, with the major difference being in the level of expression. pc43 appears to be expressed at a lower level than pc42. Both molecules are expressed in the germinal and pyramidal cells of the hippocampus, Purkinje cells of the cerebellum and neurons in grey matter. In addition, pc42 is expressed in glial cells in the white matter but, in contrast to the expression of pc43 in glioma cell lines (as described in Example 9), expression of pc43 in normal glial cells was not observed. In the spinal chord, both protocadherins are expressed in the motor neurons in the gray matter and pc42 is expressed in the glial cells in the white matter.

When expression of both protocadherin molecules was analyzed in brains and spinal chords from rats having EAE (experimental allergic encephalomyelitis) [Vandenbark et al., Cell. Immunol., 12: 85–93 (1974)], the same structures as described above were found to be positive. In addition, expression of pc42 was observed in the leukocytic infiltrates in the EAE tissues. Expression of pc42 in leukocytes was confirmed by in situ hybridization analysis of two leukocytic cell lines, RBL-1 and y3.

Expression of both protocadherin-42 and -43 was observed in the developing brain of rat embryos at all embryological days tested (E15–E19). In addition protocadherin-43 was observed in the developing rat heart at all embryological days tested (E13–E19). This finding is consistent with the immunohistochemistry results showing protocadherin-43 expression in adult heart.

To determine possible roles of protocadherins in the development of the nervous system, expression profiles of protocadherin members in developing rat brain and adult rat brain were also examined by in situ hybridization. A series of coronal, sagittal and horizontal sections of rat brains at postnatal days 0, 6, 14, 30 (P0 through P30) and at 3 months (young adult) were hybridized with labelled cRNA probes corresponding to various protocadherins of the invention including pc42, pc43, RAT-212, RAT-411, and RAT-418. In developing brain, RAT-411 was expressed at high levels in neurons of the olfactory bulb, i.e., mitral cells and periglomerular cells. The expression of RAT-411 mRNA was transient; expression appeared at P0, peaked at P6, diminished by P14, and was undetectable at P30 and in adult brain. In the adult, pc43 mRNA was found to be expressed predominantly in Purkinje cells in the cerebellum. The expression of pc43 mRNA in Purkinje cells was observed from the beginning of Purkinje cell differentiation at around P6. Other protocadherin members were expressed at very low levels in various areas of developing and adult brains. These results indicate that protocadherin members are differentially expressed during the development of the central nervous system, and suggest that RAT-411 and pc43 have specific roles during the development of olfactory bulb neurons and Purkinje cells, respectively.

EXAMPLE 13

Conventional immunoprecipitations using pc43-specific polyclonal antibodies and monoclonal antibody 38I2C were performed to identify proteins that interacted with pc43 in L cell transfectants.

The pc43 and chimeric pc43 transfectants were metabolically labeled by incubating the cells in Dulbecco's modified Eagle's medium containing [$^{35}$S] methionine (50 uCi/ml) overnight. After washing, the transfectants were lysed with PBS containing Triton X 100 and incubated with anti-pc43 antibody. The immunocomplexes were then collected using protein A-Sepharose beads. The resulting beads were washed five times with a washing buffer (50 mM Tris-HCl, pH 8.0, containing 0.5M NaCl, 0.1% ovalbumin, 0.5% NP-40, 0.5% Triton X 100 and 1 mM EDTA) at room temperature. Protein was separated by SDS-PAGE and subjected to autoradiography.

The chimeric pc43 co-precipitated with 105 kDa and a 95 kDa bands that are likely to correspond to α- and β-catenins, respectively, because anti-α-catenin and anti-β-catenin antibodies stained comparable bands. Pc43, on the other hand, co-precipitated with a 120 kDa band.

While the present invention has been described in terms of specific methods and compositions, it is understood that variations and modifications will occur to those skilled in the art. Therefore, only such limitations as appear in the claims should be placed on the invention.

What is claimed is:

1. A purified and isolated polynucleotide comprising a sequence encoding a human protocadherin pc3 having SEQ ID NO: 110.

2. A purified and isolated polynucleotide comprising a sequence encoding a human protocadherin pc5 having SEQ ID NO: 112.

3. The polynucleotide of claim 1 or 2 which is a DNA.

4. The DNA of claim 3 which is a cDNA.

5. The DNA of claim 3 which is a genomic DNA.

6. The DNA of claim 3 which is wholly or partially chemically synthesized.

7. A biologically functional DNA vector comprising a DNA according to claim 3.

8. The vector of claim 7 wherein said DNA is operatively linked to an expression control DNA sequence.

9. A host cell transformed or transfected with a DNA sequence according to claim 3 in a manner allowing the expression in said host cell of a protocadherin polypeptide.

10. A method for producing a protocadherin polypeptide comprising the steps of growing a host cell according to claim 9 under conditions that allow expression of the protocadherin polypeptide and isolating protocadherin polypeptide.

11. A polynucleotide according to claim 1, wherein said sequence comprises SEQ ID NO: 109.

12. A polynucleotide according to claim 1, wherein said sequence comprises SEQ ID NO: 111.

* * * * *

UNITED STATES PATENT AND TRADEMARK OFFICE
CERTIFICATE OF CORRECTION

PATENT NO. : 5,798,224
DATED : August 25, 1998
INVENTOR(S) : Shintaro Suzuki

It is certified that error appears in the above-identified patent and that said Letters Patent is hereby corrected as shown below:

Title page,
In Other Publications, under Hynes, "specification" should be --specificities--.
In Other Publications, under Kennett, "Kenneth" should be --Kennett--.
In Other Publications, under Lord, quotations are needed around title.
In Other Publications, under Napolitano, "Bell Biol." should be --Cell Biol.--.
Column 1, line 48, replace "an cytoplasmic" with --a cytoplasmic--.
Column 6, line 15, replace "M13 mp18" with --M13mp18--.
Column 10, line 49, replace "(7W)" with --(TW)--.
Column 10, line 54, replace "453-442 (1929)" with --442-453 (1929)--.
Column 11, line 49, replace "or by" with --or--.
Column 13, line 9, replace "(3812C)" with --(3I2C)--.
Column 14, line 27, replace "Xba1" with --XbaI--.
Column 15, line 61, replace "neuroblasloma" with --neuroblastoma--.
Column 17, line 22, replace "5 micron" with --5 microns--.
Column 17, line 56, replace "XBa1" with --XbaI--.

Signed and Sealed this

Thirtieth Day of May, 2000

*Attest:*

Q. TODD DICKINSON

*Attesting Officer*    *Director of Patents and Trademarks*

UNITED STATES PATENT AND TRADEMARK OFFICE
CERTIFICATE OF CORRECTION

PATENT NO. : 5,798,224
DATED : August 25, 1998
INVENTOR(S) : Shintaro Suzuki

It is certified that error appears in the above-identified patent and that said Letters Patent is hereby corrected as shown below:

Claim 12,
Replace the dependency on "claim 1" with -- claim 2 --.

Signed and Sealed this

Sixteenth Day of April, 2002

Attest:

JAMES E. ROGAN
Attesting Officer  Director of the United States Patent and Trademark Office

SEQUENCE LISTING ( 1 ) GENERAL INFORMATION:

( i i i ) NUMBER OF SEQUENCES: 115

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AARSSNNTNG AYTRYGA         1 7

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TTRCTRTTRC GNGGNNN 17

( 2 ) INFORMATION FOR SEQ ID NO:3:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AAGGGAGTGG ACTTTGAGGA GCAGCCTGAG CTTAGTCTCA TCCTCACGGC TTTGGATGGA 60

GGGACTCCAT CCAGGTCTGG GACTGCATTG GTTCAAGTGG AAGTCATAGA TGCCAATGAC 120

AACGCACCGT A 131

( 2 ) INFORMATION FOR SEQ ID NO:4:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Lys Gly Val Asp Phe Glu Glu Gln Pro Glu Leu Ser Leu Ile Leu Thr
  1               5                  10                  15

Ala Leu Asp Gly Gly Thr Pro Ser Arg Ser Gly Thr Ala Leu Val Gln
                20                  25                  30

Val Glu Val Ile Asp Ala Asn Asp Asn Ala Pro
                35                  40
```

( 2 ) INFORMATION FOR SEQ ID NO:5:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AAACGCATGG ATTTCGAGGA GTCTTCCTCC TACCAGATCT ATGTGCAAGC TACTGACCGG 60

GGACCAGTAC CCATGGCGGG TCATTGCAAG GTGTTGGTGG ACATTATAGA TGTGAACGAC 120

AACGCACCTA A 131

( 2 ) INFORMATION FOR SEQ ID NO:6:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Lys Ala Met Asp Phe Glu Glu Ser Ser Ser Tyr Gln Ile Tyr Val Gln
  1               5                  10                  15
```

```
Ala  Thr  Asp  Arg  Gly  Pro  Val  Pro  Met  Ala  Gly  His  Cys  Lys  Val  Leu
               20                    25                    30

Val  Asp  Ile  Ile  Asp  Val  Asn  Asp  Asn  Ala  Pro
               35                    40
```

( 2 ) INFORMATION FOR SEQ ID NO:7:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
AAGCGACTGG  ACTTTGAGAC  CCTGCAGACC  TTCGAGTTCA  GCGTGGGTGC  CACAGACCAT    60

GGCTCCCCCT  CGCTCCGCAG  TCAGGCTCTG  GTGCGCGTGG  TGGTGCTGGA  CCACAATGAC   120

AATGCCCCCA  A                                                            131
```

( 2 ) INFORMATION FOR SEQ ID NO:8:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Lys  Arg  Leu  Asp  Phe  Glu  Thr  Leu  Gln  Thr  Phe  Glu  Phe  Ser  Val  Gly
 1                    5                    10                    15

Ala  Thr  Asp  His  Gly  Ser  Pro  Ser  Leu  Arg  Ser  Gln  Ala  Leu  Val  Arg
               20                    25                    30

Val  Val  Val  Leu  Asp  His  Asn  Asp  Asn  Ala  Pro
               35                    40
```

( 2 ) INFORMATION FOR SEQ ID NO:9:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
AAGGGCCTGG  ATTACGAGGC  ACTGCAGTCC  TTCGAGTTCT  ACGTGGGCGC  TACAGATGGA    60

GGCTCACCCG  CGCTCAGCAG  CCAGACTCTG  GTGCGGATGG  TGGTGCTGGA  TGACAACGAC   120

AACGCCCCTA  A                                                            131
```

( 2 ) INFORMATION FOR SEQ ID NO:10:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Lys Gly Leu Asp Tyr Glu Ala Leu Gln Ser Phe Glu Phe Tyr Val Gly
1               5                   10                  15

Ala Thr Asp Gly Gly Ser Pro Ala Leu Ser Ser Gln Thr Leu Val Arg
            20                  25                  30

Met Val Val Leu Asp Asp Asn Asp Asn Ala Pro
        35              40
```

( 2 ) INFORMATION FOR SEQ ID NO:11:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
AAGGCGTTTG ATTTTGAGGA TCAGAGAGAG TTCCAGCTAA CCGCTCATAT AAACGACGGA    60
GGTACCCCGG TTTTGGCCAC CAACATCAGC GTGAACATAT TTGTTACTGA CCGCAATGAC   120
AACGCCCCGC A                                                        131
```

( 2 ) INFORMATION FOR SEQ ID NO:12:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Lys Ala Phe Asp Phe Glu Asp Gln Arg Glu Phe Gln Leu Thr Ala His
1               5                   10                  15

Ile Asn Asp Gly Gly Thr Pro Val Leu Ala Thr Asn Ile Ser Val Asn
            20                  25                  30

Ile Phe Val Thr Asp Arg Asn Asp Asn Ala Pro
        35              40
```

( 2 ) INFORMATION FOR SEQ ID NO:13:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

```
AAGGCGGTGG ATTACGAAAT CACCAAGTCC TATGAGATAG ATGTTCAAGC CCAAGATCTG    60
GGTCCCAATT CTATTCCTGC TCATTGCAAA ATTATAATTA AGGTCGTGGA TGTCAACGAC   120
AACGCTCCCA A                                                        131
```

( 2 ) INFORMATION FOR SEQ ID NO:14:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

| Lys | Ala | Val | Asp | Tyr | Glu | Ile | Thr | Lys | Ser | Tyr | Glu | Ile | Asp | Val | Gln |
|---|---|---|---|---|---|---|---|---|---|---|---|---|---|---|---|
| 1 | | | | 5 | | | | | 10 | | | | | 15 | |

| Ala | Gln | Asp | Leu | Gly | Pro | Asn | Ser | Ile | Pro | Ala | His | Cys | Lys | Ile | Ile |
|---|---|---|---|---|---|---|---|---|---|---|---|---|---|---|---|
| | | | 20 | | | | | 25 | | | | | 30 | | |

| Ile | Lys | Val | Val | Asp | Val | Asn | Asp | Asn | Ala | Pro |
|---|---|---|---|---|---|---|---|---|---|---|
| | | 35 | | | | | 40 | | | |

( 2 ) INFORMATION FOR SEQ ID NO:15:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

```
TATGACCATG ATTACGAGAC AACCAAAGAA TATACACTGC GGATCCGGGC CCAGGATGGT        60

GGCCGGACTC CACTTTCCAA CGTCTCCGGT CTAGTAACCG TGCAGGTCCT AGACATCAAC       120

GACAATGCCC CCCCA                                                        135
```

( 2 ) INFORMATION FOR SEQ ID NO:16:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

| Tyr | Asp | His | Asp | Tyr | Glu | Thr | Thr | Lys | Glu | Tyr | Thr | Leu | Arg | Ile | Arg |
|---|---|---|---|---|---|---|---|---|---|---|---|---|---|---|---|
| 1 | | | | 5 | | | | | 10 | | | | | 15 | |

| Ala | Gln | Asp | Gly | Gly | Arg | Thr | Pro | Leu | Ser | Asn | Val | Ser | Gly | Leu | Val |
|---|---|---|---|---|---|---|---|---|---|---|---|---|---|---|---|
| | | | 20 | | | | | 25 | | | | | 30 | | |

| Thr | Val | Gln | Val | Leu | Asp | Ile | Asn | Asp | Asn | Ala | Pro |
|---|---|---|---|---|---|---|---|---|---|---|---|
| | | 35 | | | | | 40 | | | | |

( 2 ) INFORMATION FOR SEQ ID NO:17:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
GGGGGGTCGA TTACGAGGAG AACGGCATGT TAGAGATCGA CGTGCAGGCC AGAGACCTAG        60

GACCTAACCC AATTCCAGCC CATTGCAAGG TCACAGTCAA GCTCATCGAC CGCAATGATA       120

ACGCCCCCA                                                               129
```

( 2 ) INFORMATION FOR SEQ ID NO:18:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear -continued (ii) MOLECULE TYPE: protein (xi) SEQUENCE DESCRIPTION: SEQ ID NO:18:

```
Arg Gly Val Asp Tyr Glu Glu Asn Gly Met Leu Glu Ile Asp Val Gln
1               5                   10                  15

Ala Arg Asp Leu Gly Pro Asn Pro Ile Pro Ala His Cys Lys Val Thr
                20                  25                  30

Val Lys Leu Ile Asp Arg Asn Asp Asn Ala Pro
                35                  40
```

(2) INFORMATION FOR SEQ ID NO:19:

(i) SEQUENCE CHARACTERISTICS:
      (A) LENGTH: 131 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:19:

```
AAGGGGTTGG ACTACGAAGA CACCAAACTC CATGAGATTT ACATCCAGGC CAAAGACAAA        60
GGTGCCAATC CGGAAGGAGC GCATTGCAAA GTACTGGTAG AGGTTGTGGA CGTTAACGAC       120
AATGCCCCTC A                                                            131
```

(2) INFORMATION FOR SEQ ID NO:20:

(i) SEQUENCE CHARACTERISTICS:
      (A) LENGTH: 43 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:20:

```
Lys Gly Leu Asp Tyr Glu Asp Thr Lys Leu His Glu Ile Tyr Ile Gln
1               5                   10                  15

Ala Lys Asp Lys Gly Ala Asn Pro Glu Gly Ala His Cys Lys Val Leu
                20                  25                  30

Val Glu Val Val Asp Val Asn Asp Asn Ala Pro
                35                  40
```

(2) INFORMATION FOR SEQ ID NO:21:

(i) SEQUENCE CHARACTERISTICS:
      (A) LENGTH: 131 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:21:

```
AAGGGTTTGG ACTTTGAGCA AGTAGATGTC TACAAAATCC GCGTTGACGC GACGGACAAA        60
GGACACCCTC CGATGGCAGG CCATTGCACT GTTTAGTGA GGGTATTGGA TGAAAACGAC        120
AATGCGCCTC T                                                            131
```

(2) INFORMATION FOR SEQ ID NO:22:

(i) SEQUENCE CHARACTERISTICS:
      (A) LENGTH: 43 amino acids
      (B) TYPE: amino acid
      (C) STRANDEDNESS: single ( D ) TOPOLOGY: linear ( i i ) MOLECULE TYPE: protein ( x i ) SEQUENCE DESCRIPTION: SEQ ID NO:22:

Lys Gly Leu Asp Phe Glu Gln Val Asp Val Tyr Lys Ile Arg Val Asp
1               5                   10                  15

Ala Thr Asp Lys Gly His Pro Pro Met Ala Gly His Cys Thr Val Leu
            20                  25                  30

Val Arg Val Leu Asp Glu Asn Asp Asn Ala Pro
            35                  40

( 2 ) INFORMATION FOR SEQ ID NO:23:

( i ) SEQUENCE CHARACTERISTICS:
       ( A ) LENGTH: 134 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:23:

AAGGGTATAG ACTTCGAGCA GATCAAGGAC TTCAGCTTTC AAGTGGAAGC CCGGGACGCC    60

GGCAGTCCCC AGGCGCTGTC CGGCAACTGC ACTGTCAACA TCTTGATAGT GGATCAGAAC   120

GACAACGCCC CTAA                                                     134

( 2 ) INFORMATION FOR SEQ ID NO:24:

( i ) SEQUENCE CHARACTERISTICS:
       ( A ) LENGTH: 44 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:24:

Lys Gly Ile Asp Phe Glu Gln Ile Lys Asp Phe Ser Phe Gln Val Glu
1               5                   10                  15

Ala Arg Asp Ala Gly Ser Pro Gln Ala Leu Ala Gly Asn Thr Thr Val
            20                  25                  30

Asn Ile Leu Ile Val Asp Gln Asn Asp Asn Ala Pro
            35                  40

( 2 ) INFORMATION FOR SEQ ID NO:25:

( i ) SEQUENCE CHARACTERISTICS:
       ( A ) LENGTH: 134 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:25:

AAGCCGTTCG ACTATGAGCA AACCGCCAAC ACGCTGGCAC AGATTGACGC CGTGCTGGAA    60

AAACAGGGCA GCAATAAATC GAGCATTCTG GATGCCACCA TTTCCTGGC CGATAAAAAC   120

GACAATGCGC CAGA                                                    134

( 2 ) INFORMATION FOR SEQ ID NO:26:

( i ) SEQUENCE CHARACTERISTICS:
       ( A ) LENGTH: 44 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:26:

| Lys | Pro | Phe | Asp | Tyr | Glu | Gln | Thr | Ala | Asn | Thr | Leu | Ala | Gln | Ile | Asp |
|---|---|---|---|---|---|---|---|---|---|---|---|---|---|---|---|
| 1 | | | | 5 | | | | | 10 | | | | | 15 | |
| Ala | Val | Leu | Glu | Lys | Gln | Gly | Ser | Asn | Lys | Ser | Ser | Ile | Leu | Asp | Ala |
| | | | 20 | | | | | 25 | | | | | 30 | | |
| Thr | Ile | Phe | Leu | Ala | Asp | Lys | Asn | Asp | Asn | Ala | Pro | | | | |
| | | 35 | | | | | 40 | | | | | | | | |

( 2 ) INFORMATION FOR SEQ ID NO:27:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:27:

```
AAGCGGCTGG ATTTCGAACA GTTCCAGCAG CACAAGCTGC TCGTAAGGGC TGTTGATGGA        60
GGAATGCCGC CACTGAGCAG CGATGTGGTC GTCACTGTGG ATGTCACCGA CCTCAACGAT       120
AACGCGCCCT A                                                            131
```

( 2 ) INFORMATION FOR SEQ ID NO:28:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:28:

| Lys | Arg | Leu | Asp | Phe | Glu | Gln | Phe | Gln | Gln | His | Lys | Leu | Leu | Val | Arg |
|---|---|---|---|---|---|---|---|---|---|---|---|---|---|---|---|
| 1 | | | | 5 | | | | | 10 | | | | | 15 | |
| Ala | Val | Asp | Gly | Gly | Met | Pro | Pro | Leu | Ser | Ser | Asp | Val | Val | Val | Thr |
| | | | 20 | | | | | 25 | | | | | 30 | | |
| Val | Asp | Val | Thr | Asp | Leu | Asn | Asp | Asn | Ala | Pro | | | | | |
| | | 35 | | | | | 40 | | | | | | | | |

( 2 ) INFORMATION FOR SEQ ID NO:29:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:29:

```
AAGGGGATAG ACTTTGAGAG TGAGAATTAC TATGAATTTG ATGTGCGGGC TCGCGATGGG        60
GGTTCTCCAG CCATGGAGCA ACATTGCAGC CTTCGAGTGG ATCTGCTGGA CGTAAATGAC       120
AACGCCCCAC T                                                            131
```

( 2 ) INFORMATION FOR SEQ ID NO:30:

(i) SEQUENCE CHARACTERISTICS:
  (A) LENGTH: 43 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:30:

```
Lys Gly Ile Asp Phe Glu Ser Glu Asn Tyr Tyr Glu Phe Asp Val Arg
 1               5                  10                  15
Ala Arg Asp Gly Gly Ser Pro Ala Met Glu Gln His Cys Ser Leu Arg
            20                  25                  30
Val Asp Leu Leu Asp Val Asn Asp Asn Ala Pro
            35                  40
```

(2) INFORMATION FOR SEQ ID NO:31:

(i) SEQUENCE CHARACTERISTICS:
  (A) LENGTH: 131 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:31:

```
AAGGCATTGG ACTTTGAGGC CGGCGACTG TATTCGCTGA CAGTTCAGGC CACGGACCGA      60
GGCGTGCCCT CGCTCACCGG GCGTGCCGAA GCGCTTATCC AGCTGCTAGA TGTCAACGAC    120
AACGCACCCA T                                                        131
```

(2) INFORMATION FOR SEQ ID NO:32:

(i) SEQUENCE CHARACTERISTICS:
  (A) LENGTH: 43 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:32:

```
Lys Ala Leu Asp Phe Glu Ala Arg Arg Leu Tyr Ser Leu Thr Val Gln
 1               5                  10                  15
Ala Thr Asp Arg Gly Val Pro Ser Leu Thr Gly Arg Ala Glu Ala Leu
            20                  25                  30
Ile Gln Leu Leu Asp Val Asn Asp Asn Ala Pro
            35                  40
```

(2) INFORMATION FOR SEQ ID NO:33:

(i) SEQUENCE CHARACTERISTICS:
  (A) LENGTH: 125 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:33:

```
AAGCCAATTG ATTACGAGGC AACTCCATAC TATAACATGG AAATTGTAGC CACAGACAGC     60
GGAGGTCTTT CGGGAAAATG CACTGTGTCT ATACAGGTGG TGGATGTGAA CGACAACGCC    120
CCCAA                                                                125
```

( 2 ) INFORMATION FOR SEQ ID NO:34:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
Lys Pro Ile Asp Tyr Glu Ala Thr Pro Tyr Tyr Asn Met Glu Ile Val
 1               5                  10                  15

Ala Thr Asp Ser Gly Gly Leu Ser Gly Lys Cys Thr Val Ser Ile Gln
            20                  25                  30

Val Val Asp Val Asn Asp Asn Ala Pro
            35                  40
```

( 2 ) INFORMATION FOR SEQ ID NO:35:

( i ) SEQUENCE CHARACTERISTICS:
        ( A ) LENGTH: 446 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

```
AAGCGGGTAG ACTTCGAAAT GTGCAAAAGA TTTTACCTTG TGGTGGAAGC TAAAGACGGA    60
GGCACCCCAG CCCTCAGCAC GGCAGCCACT GTCAGCATCG ACCTCACAGA TGTGAATGAT   120
AACCCTCCTC GGTTCAGCCA AGATGTCTAC AGTGCTGTCA TCAGTGAGGA TGCCTTAGAG   180
GGGGACTCTG TCATTCTGCT GATAGCAGAA GATGTGGATA GCAAGCCTAA TGGACAGATT   240
CGGTTTTCCA TCGTGGGTGG AGATAGGGAC AATGAATTTG CTGTCGATCC AATCTTGGGA   300
CTTGTGAAAG TTAAGAAGAA ACTGGACCGG GAGCGGGTGT CAGGATACTC CCTGCTCATC   360
CAGGCAGTAG ATAGTGGCAT TCCTGCAATG TCCTCAACGA CAACTGTCAA CATTGATATT   420
TCTGATGTGA ACGACAACGC CCCCCT                                        446
```

( 2 ) INFORMATION FOR SEQ ID NO:36:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

```
Lys Arg Val Asp Phe Glu Met Cys Lys Arg Phe Tyr Leu Val Val Glu
 1               5                  10                  15

Ala Lys Asp Gly Gly Thr Pro Ala Leu Ser Thr Ala Ala Thr Val Ser
            20                  25                  30

Ile Asp Leu Thr Asp Val Asn Asp Asn Pro Pro Arg Phe Ser Gln Asp
            35                  40                  45

Val Tyr Asp Ala Val Ile Ser Glu Asp Ala Leu Glu Gly Asp Ser Val
        50                  55                  60

Ile Leu Leu Ile Ala Glu Asp Val Asp Ser Lys Pro Asn Gly Gln Ile
65                  70                  75                  80

Arg Phe Ser Ile Val Gly Gly Asp Arg Asp Asn Glu Phe Ala Val Asp
                85                  90                  95
```

```
Pro  Ile  Leu  Gly  Leu  Val  Lys  Val  Lys  Lys  Leu  Asp  Arg  Glu  Arg
          100                      105                     110

Val  Ser  Gly  Tyr  Ser  Leu  Leu  Ile  Gln  Ala  Val  Asp  Ser  Gly  Ile  Pro
          115                      120                     125

Ala  Met  Ser  Ser  Thr  Thr  Thr  Val  Asn  Ile  Asp  Ile  Ser  Asp  Val  Asn
          130                      135                     140

Asp  Asn  Ala  Pro
145
```

( 2 ) INFORMATION FOR SEQ ID NO:37:

( i ) SEQUENCE CHARACTERISTICS:
   ( A ) LENGTH: 440 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:37:

```
AAGGGGGTTG  ATTATGAGAC  AAACCCACGG  CTACGACTGG  TGCTACAGGC  AGAGAGTGGA    60
GGAGCCTTTG  CTTTCTCGGT  GCTGACCCTG  ACCCTTCAAG  ATGCCAATGA  CAATGCTCCC   120
CGTTTCCTGC  AGCCTCACTA  CGTGGCTTTC  CTGCCAGAGT  CCCGACCCTT  GGAAGGGCCC   180
CTGCTGCAGG  TGGAAGCAGA  CGACCTGGAT  CAAGGCTCTG  GAGGACAGAT  CTCCTACAGT   240
CTGGCTGCAT  CCCAGCCAGC  ACGGGGCTTG  TTCCATGTAG  ACCCAGCCAC  AGGCACTATC   300
ACTACCACAG  CCATCCTGGA  CCGGGAAATC  TGGGCTGAAA  CACGGCTGGT  ACTGATGGCC   360
ACAGACAGAG  GAAGCCCAGC  ATTGGTGGGC  TCAGCTACCC  TGACAGTGAT  GGTCATCGAT   420
ACCAACGACA  ATGCTCCCCT                                                   440
```

( 2 ) INFORMATION FOR SEQ ID NO:38:

( i ) SEQUENCE CHARACTERISTICS:
   ( A ) LENGTH: 146 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:38:

```
Lys  Gly  Val  Asp  Tyr  Glu  Thr  Asn  Pro  Arg  Leu  Arg  Leu  Val  Leu  Gln
1              5                      10                      15

Ala  Glu  Ser  Gly  Gly  Ala  Phe  Ala  Phe  Ser  Val  Leu  Thr  Leu  Thr  Leu
          20                      25                      30

Gln  Asp  Ala  Asn  Asp  Asn  Ala  Pro  Arg  Phe  Leu  Gln  Pro  His  Tyr  Val
          35                      40                      45

Ala  Phe  Leu  Pro  Glu  Ser  Arg  Pro  Leu  Glu  Gly  Pro  Leu  Leu  Gln  Val
     50                      55                      60

Glu  Ala  Asn  Asp  Leu  Asp  Gln  Gly  Ser  Gly  Gly  Gln  Ile  Ser  Tyr  Ser
65                           70                      75                       80

Leu  Ala  Ala  Ser  Gln  Pro  Ala  Arg  Gly  Leu  Phe  His  Val  Asp  Pro  Ala
                    85                       90                      95

Thr  Gly  Thr  Ile  Thr  Thr  Thr  Ala  Ile  Leu  Asp  Arg  Glu  Ile  Trp  Ala
               100                     105                     110

Glu  Thr  Arg  Leu  Val  Leu  Met  Ala  Thr  Asp  Arg  Gly  Ser  Pro  Ala  Leu
          115                     120                     125

Val  Gly  Ser  Ala  Thr  Leu  Thr  Val  Met  Val  Ile  Asp  Thr  Asn  Asp  Asn
```

( 2 ) INFORMATION FOR SEQ ID NO:39:

( i ) SEQUENCE CHARACTERISTICS:
        ( A ) LENGTH: 124 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

```
AAGGTCTCGA TTATGAGGCA ACTCCATATT ATAACGTGGA AATTGTAGCC ACAGATGGTG      60
GGGGCCTTTC AGGAAAATGC ACTGTGGCTA TAGAAGTGGT GGATGTGAAC GACGGCGCTC     120
CAAT                                                                  124
```

( 2 ) INFORMATION FOR SEQ ID NO:40:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

```
Lys Gly Leu Asp Tyr Glu Ala Thr Pro Tyr Tyr Asn Val Glu Ile Val
1               5                   10                  15
Ala Thr Asp Gly Gly Ala Phe Asp Glu Asn Cys Thr Val Ala Ile Glu
            20                  25                  30
Val Val Asp Val Asn Asp Asn Ala Pro
        35                  40
```

( 2 ) INFORMATION FOR SEQ ID NO:41:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

```
Asp Xaa Asn Glu Xaa Pro Xaa Phe
1               5
```

( 2 ) INFORMATION FOR SEQ ID NO:42:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

```
Asp Xaa Asp Glu Xaa Pro Xaa Phe
1               5
```

( 2 ) INFORMATION FOR SEQ ID NO:43:

( i ) SEQUENCE CHARACTERISTICS:
   ( A ) LENGTH: 9 amino acids
   ( B ) TYPE: amino acid
   ( C ) STRANDEDNESS: single
   ( D ) TOPOLOGY: linear ( i i ) MOLECULE TYPE: DNA ( x i ) SEQUENCE DESCRIPTION: SEQ ID NO:43:

```
Asp  Xaa  Asn  Asp  Asn  Xaa  Pro  Xaa  Phe
1                   5
```

( 2 ) INFORMATION FOR SEQ ID NO:44:

( i ) SEQUENCE CHARACTERISTICS:
   ( A ) LENGTH: 131 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:44:

```
AAGCGGATGG ATTTGAAGA  CACCAAACTC CATGAGATTT ACATCCAGGC CAAAGACAAA      60
GGTGCCAATC CCGAAGGAGC GCATTGCAAA GTACTTGTAG AGGTTGTAGA CGTAAACGAC     120
AACGCCCCAG T                                                          131
```

( 2 ) INFORMATION FOR SEQ ID NO:45:

( i ) SEQUENCE CHARACTERISTICS:
   ( A ) LENGTH: 43 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:45:

```
Leu  Arg  Met  Asp  Phe  Glu  Asp  Thr  Lys  Leu  His  Glu  Ile  Tyr  Ile  Gln
1                   5                        10                       15

Ala  Lys  Asp  Lys  Gly  Ala  Asn  Pro  Glu  Gly  Ala  His  Cys  Lys  Val  Leu
               20                        25                       30

Val  Glu  Val  Val  Asp  Val  Asn  Asp  Asn  Ala  Pro
          35                   40
```

( 2 ) INFORMATION FOR SEQ ID NO:46:

( i ) SEQUENCE CHARACTERISTICS:
   ( A ) LENGTH: 131 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:46:

```
AAGGCTTTGG ATTACGAGGA TCAGAGAGAG TTCCAACTAA CAGCTCATAT AAACGACGGA      60
GGTACCCCAG TCTTAGCCAC CAACATCAGC GTGAACGTAT TTGTTACTGA CCGCAATGAT     120
AACGCCCCCT A                                                          131
```

( 2 ) INFORMATION FOR SEQ ID NO:47:

( i ) SEQUENCE CHARACTERISTICS:
   ( A ) LENGTH: 43 amino acids
   ( B ) TYPE: amino acid (C) STRANDEDNESS: single
(D) TOPOLOGY: linear (i i) MOLECULE TYPE: protein (x i) SEQUENCE DESCRIPTION: SEQ ID NO:47:

```
Lys Ala Leu Asp Tyr Glu Asp Gln Arg Glu Phe Gln Leu Thr Ala His
  1               5                  10                  15

Ile Asn Asp Gly Gly Thr Pro Val Leu Ala Thr Asn Ile Ser Val Asn
             20                  25                  30

Val Phe Val Thr Asp Arg Asn Asp Asn Ala Pro
             35                  40
```

(2) INFORMATION FOR SEQ ID NO:48:

(i) SEQUENCE CHARACTERISTICS:
    (A) LENGTH: 131 base pairs
    (B) TYPE: nucleic acid
    (C) STRANDEDNESS: single
    (D) TOPOLOGY: linear (i i) MOLECULE TYPE: cDNA (x i) SEQUENCE DESCRIPTION: SEQ ID NO:48:

AAGCGCTTGG ACTACGAGGA GAGTAACAAT TATGAAATTC ACGTGGATGC TACAGATAAA    60

GGATACCCAC CTATGGTTGC TCACTGCACC GTACTCGTGG GAATCTTGGA TGAAAATGAC   120

AACGCACCCA T                                                        131

(2) INFORMATION FOR SEQ ID NO:49:

(i) SEQUENCE CHARACTERISTICS:
    (A) LENGTH: 43 amino acids
    (B) TYPE: amino acid
    (C) STRANDEDNESS: single
    (D) TOPOLOGY: linear (i i) MOLECULE TYPE: protein (x i) SEQUENCE DESCRIPTION: SEQ ID NO:49:

```
Lys Arg Leu Asp Tyr Glu Glu Ser Asn Asn Tyr Glu Ile His Val Asp
  1               5                  10                  15

Ala Thr Asp Lys Gly Tyr Pro Pro Met Val Ala His Cys Thr Val Leu
             20                  25                  30

Val Gly Ile Leu Asp Glu Asn Asp Asn Ala Pro
             35                  40
```

(2) INFORMATION FOR SEQ ID NO:50:

(i) SEQUENCE CHARACTERISTICS:
    (A) LENGTH: 131 base pairs
    (B) TYPE: nucleic acid
    (C) STRANDEDNESS: single
    (D) TOPOLOGY: linear (i i) MOLECULE TYPE: cDNA (x i) SEQUENCE DESCRIPTION: SEQ ID NO:50:

AAACCGGTGG ACTACGAGAA AGTCAAAGAC TATACCATCG AGATCGTGGC TGTGGATTCC    60

GGCAACCCTC CACTCTCTAG CACCAACTCC CTCAAGGTGC AGGTGGTAGA CGTCAACGAT   120

AACGCCCCTC T                                                        131

(2) INFORMATION FOR SEQ ID NO:51:

(i) SEQUENCE CHARACTERISTICS:

(A) LENGTH: 43 amino acids
(B) TYPE: amino acid
(C) STRANDEDNESS: single
(D) TOPOLOGY: linear ( i i ) MOLECULE TYPE: protein ( x i ) SEQUENCE DESCRIPTION: SEQ ID NO:51:

```
Lys Pro Val Asp Tyr Glu Lys Val Lys Asp Tyr Thr Ile Glu Ile Val
1               5                   10                  15
Ala Val Asp Ser Gly Asn Pro Pro Leu Ser Ser Thr Asn Ser Leu Lys
            20                  25                  30
Val Gln Val Val Asp Val Asn Asp Asn Ala Pro
        35                  40
```

( 2 ) INFORMATION FOR SEQ ID NO:52:

( i ) SEQUENCE CHARACTERISTICS:
(A) LENGTH: 131 base pairs
(B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:52:

```
AAGCCTTTTG ATTCGAGGA CACCAAACTC CATGAGATTT ACATCCAGGC CAAAGACAAG       60
GGCGCCAATC CGAAGGAGC ACATTGCAAA GTGTTGGTGG AGGTTGTGGA TGTGAACGAC      120
AATGCCCCTC A                                                          131
```

( 2 ) INFORMATION FOR SEQ ID NO:53:

( i ) SEQUENCE CHARACTERISTICS:
(A) LENGTH: 43 amino acids
(B) TYPE: amino acid
(C) STRANDEDNESS: single
(D) TOPOLOGY: linear ( i i ) MOLECULE TYPE: protein ( x i ) SEQUENCE DESCRIPTION: SEQ ID NO:53:

```
Lys Pro Phe Asp Phe Glu Asp Thr Lys Leu His Glu Ile Tyr Ile Gln
1               5                   10                  15
Ala Lys Asp Lys Gly Ala Asn Pro Glu Gly Ala His Cys Lys Val Leu
            20                  25                  30
Val Glu Val Val Asp Val Asn Asp Asn Ala Pro
        35                  40
```

( 2 ) INFORMATION FOR SEQ ID NO:54:

( i ) SEQUENCE CHARACTERISTICS:
(A) LENGTH: 122 base pairs
(B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:54:

```
AAAGGTGTCG ATTACGAGGT GAGTCCACGG CTGCGACTGG TGCTGCAGGC AGAGAGTCGA       60
GGAGCCTTTG CCTTCACTGT GCTGACCCTG ACCCTGCAAG ATGCCAACGA CAACGCCCCG      120
AG                                                                    122
```

( 2 ) INFORMATION FOR SEQ ID NO:55:

( i ) SEQUENCE CHARACTERISTICS:
- ( A ) LENGTH: 40 amino acids
- ( B ) TYPE: amino acid
- ( C ) STRANDEDNESS: single
- ( D ) TOPOLOGY: linear ( i i ) MOLECULE TYPE: protein ( x i ) SEQUENCE DESCRIPTION: SEQ ID NO:55:

```
Lys Gly Val Asp Tyr Glu Val Ser Pro Arg Leu Arg Leu Val Leu Gln
1               5                   10                  15
Ala Glu Ser Arg Gly Ala Phe Ala Phe Thr Val Leu Thr Leu Thr Leu
            20                  25                  30
Gln Asp Ala Asn Asp Asn Ala Pro
            35                  40
```

( 2 ) INFORMATION FOR SEQ ID NO:56:

( i ) SEQUENCE CHARACTERISTICS:
- ( A ) LENGTH: 131 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:56:

```
AAAGGGATTG ATTACGAGCA GTTGAGAGAC CTACAGCTGT GGGTGACAGC CAGCGACAGC        60
GGGGACCCGC CTCTTAGCAG CAACGTGTCA CTGAGCCTGT TTGTGCTGGA CCAGAACGAC        120
AACGCCCCC T                                                              131
```

( 2 ) INFORMATION FOR SEQ ID NO:57:

( i ) SEQUENCE CHARACTERISTICS:
- ( A ) LENGTH: 43 amino acids
- ( B ) TYPE: amino acid
- ( C ) STRANDEDNESS: single
- ( D ) TOPOLOGY: linear ( i i ) MOLECULE TYPE: protein ( x i ) SEQUENCE DESCRIPTION: SEQ ID NO:57:

```
Lys Gly Ile Asp Tyr Glu Gln Leu Arg Asp Leu Gln Leu Trp Val Thr
1               5                   10                  15
Ala Ser Asp Ser Gly Asp Pro Pro Leu Ser Ser Asn Val Ser Leu Ser
            20                  25                  30
Leu Phe Val Leu Asp Gln Asn Asp Asn Ala Pro
            35                  40
```

( 2 ) INFORMATION FOR SEQ ID NO:58:

( i ) SEQUENCE CHARACTERISTICS:
- ( A ) LENGTH: 125 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:58:

```
AAGGCGGTCG ATTTTGAGCG CACATCCTCT TATCAACTCA TCATTCAGGC CACCAATATG        60
GCAGGAATGG CTTCCAATGC TACAGTCAAT ATTCAGATTG TTGATGAAAA CGACAACGCC        120
CCCCA                                                                    125
```

( 2 ) INFORMATION FOR SEQ ID NO:59:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:59:

```
Lys Ala Val Asp Phe Glu Arg Thr Ser Ser Tyr Gln Leu Ile Ile Gln
 1               5                  10                  15
Ala Thr Asn Met Ala Gly Met Ala Ser Asn Ala Thr Val Asn Ile Gln
            20                  25                  30
Ile Val Asp Glu Asn Asp Asn Ala Pro
            35              40
```

( 2 ) INFORMATION FOR SEQ ID NO:60:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

```
AAACGGCTAG ACTTTGAAAA GATACAAAAA TATGTTGTAT GGATAGAGGC CAGAGATGGT      60
GGTTTCCCTC CTTTCTCCTC TTACGAGAAA CTTGATATAA CAGTATTAGA TGTCAACGAT     120
AACGCGCCTA A                                                         131
```

( 2 ) INFORMATION FOR SEQ ID NO:61:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:61:

```
Lys Arg Leu Asp Phe Glu Lys Ile Gln Lys Tyr Val Val Trp Ile Glu
 1               5                  10                  15
Ala Arg Asp Gly Gly Phe Pro Pro Phe Ser Ser Tyr Glu Lys Leu Asp
            20                  25                  30
Ile Thr Val Leu Asp Val Asn Asp Asn Ala Pro
            35              40
```

( 2 ) INFORMATION FOR SEQ ID NO:62:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

```
AAGGGGATCG ATTATGAGAA GGTCAAAGAC TACACCATTG AGATTGTGGC TGTGGACTCT      60
GGCAACCCCC CACTCTCCAG CACTAACTCC CTCAAGGTGC AGGTGGTGGA CGTCAATGAC     120
```

```
AACGCACCGT G                                                                                     131
```

( 2 ) INFORMATION FOR SEQ ID NO:63:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:63:

```
Lys  Gly  Ile  Asp  Tyr  Glu  Lys  Val  Lys  Asp  Tyr  Thr  Ile  Glu  Ile  Val
 1                   5                        10                       15
Ala  Val  Asp  Ser  Gly  Asn  Pro  Pro  Leu  Ser  Ser  Thr  Asn  Ser  Leu  Lys
               20                       25                       30
Val  Gln  Val  Val  Asp  Val  Asn  Asp  Asn  Ala  Pro
          35                       40
```

( 2 ) INFORMATION FOR SEQ ID NO:64:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:64:

```
AAGGGACTCG ACTACGAGGA TCGGCGGGAA TTTGAATTAA CAGCTCATAT CAGCGATGGG        60
GGCACCCCGG TCCTAGCCAC CAACATCAGC GTGAACATAT TTGTCACTGA TCGCAACGAT       120
AATGCCCCCG T                                                            131
```

( 2 ) INFORMATION FOR SEQ ID NO:65:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:65:

```
Lys  Gly  Leu  Asp  Tyr  Glu  Asp  Arg  Arg  Glu  Phe  Glu  Leu  Thr  Ala  His
 1                   5                        10                       15
Ile  Ser  Asp  Gly  Gly  Thr  Pro  Val  Leu  Ala  Thr  Asn  Ile  Ser  Val  Asn
               20                       25                       30
Ile  Phe  Val  Thr  Asp  Arg  Asn  Asp  Asn  Ala  Pro
          35                       40
```

( 2 ) INFORMATION FOR SEQ ID NO:66:

( i ) SEQUENCE CHARACTERISTICS:
        ( A ) LENGTH: 470 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:66:

```
AAGGGTTTGG ACTACGAGAC CACACAGGCC TACCAGCTCA CGGTCAACGC CACAGATCAA        60
```

```
GACAACACCA  GGCCTCTGTC  CACCCTGGCC  AACTTGGCCA  TCATCATCAC  AGATGTCCAG      120

GACATGGACC  CCATCTTCAT  CAACCTGCCT  TACAGCACCA  ACATCTACGA  GCATTCTCCT      180

CCGGGCACGA  CGGTGCGCAT  CATCACCGCC  ATAGACCAGG  ATCAAGGACG  TCCCCGGGGC      240

ATTGGCTACA  CCATCGTTTC  AGGGAATACC  AACAGCATCT  TTGCCCTGGA  CTACATCAGC      300

GGAGTGCTGA  CCTTGAATGG  CCTGCTGGAC  CGGGAGAACC  CCCTGTACAG  CCATGGCTTC      360

ATCCTGACTG  TGAAGGGCAC  GGAGCTGAAC  GATGACCGCA  CCCCATCTGA  CGCTACAGTC      420

ACCACGACCT  TCAATATCCT  GGTTATTGAC  ATCAACGACA  ACGCCCCACT                  470
```

( 2 ) INFORMATION FOR SEQ ID NO:67:

( i ) SEQUENCE CHARACTERISTICS:
( A ) LENGTH: 156 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:67:

```
Lys  Gly  Leu  Asp  Tyr  Glu  Thr  Thr  Gln  Ala  Tyr  Gln  Leu  Thr  Val  Asn
 1              5                        10                       15

Ala  Thr  Asp  Gln  Asp  Asn  Thr  Arg  Pro  Leu  Ser  Thr  Leu  Ala  Asn  Leu
               20                        25                       30

Ala  Ile  Ile  Ile  Thr  Asp  Val  Gln  Asp  Met  Asp  Pro  Ile  Phe  Ile  Asn
          35                        40                       45

Leu  Pro  Tyr  Ser  Thr  Asn  Ile  Tyr  Glu  His  Ser  Pro  Pro  Gly  Thr  Thr
     50                        55                       60

Val  Arg  Ile  Ile  Thr  Ala  Ile  Asp  Gln  Asp  Gln  Gly  Arg  Pro  Arg  Gly
 65                       70                       75                   80

Ile  Gly  Tyr  Thr  Ile  Val  Ser  Gly  Asn  Thr  Asn  Ser  Ile  Phe  Ala  Leu
               85                        90                       95

Asp  Tyr  Ile  Ser  Gly  Val  Leu  Thr  Leu  Asn  Gly  Leu  Leu  Asp  Arg  Glu
               100                       105                      110

Asn  Pro  Leu  Tyr  Ser  Gly  Gly  Phe  Ile  Leu  Thr  Val  Lys  Gly  Thr  Glu
          115                       120                      125

Leu  Asn  Asp  Asp  Arg  Thr  Pro  Ser  Asp  Ala  Thr  Val  Thr  Thr  Thr  Phe
     130                       135                      140

Asn  Ile  Leu  Val  Ile  Asp  Ile  Asn  Asp  Asn  Ala  Pro
145                       150                      155
```

( 2 ) INFORMATION FOR SEQ ID NO:68:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:68:

```
AAGGGGGTCG  ATTACGAGGT  ACTACAGGCC  TTTGAGTTCC  ACGTGAGCGC  CACAGACCGA      60

GGCTCACCGG  GGCTCAGCAG  CCAGGCTCTG  GTGCGCGTGG  TGGTGCTGGA  CGACAATGAC      120

AACGCTCCCG  T                                                               131
```

( 2 ) INFORMATION FOR SEQ ID NO:69:

( i ) SEQUENCE CHARACTERISTICS:

( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:69:

| Lys | Gly | Val | Asp | Tyr | Glu | Val | Leu | Gln | Ala | Phe | Glu | Phe | His | Val | Ser |
|---|---|---|---|---|---|---|---|---|---|---|---|---|---|---|---|
| 1 | | | | 5 | | | | | 10 | | | | | 15 | |

| Ala | Thr | Asp | Arg | Gly | Ser | Pro | Gly | Leu | Ser | Ser | Gln | Ala | Leu | Val | Arg |
|---|---|---|---|---|---|---|---|---|---|---|---|---|---|---|---|
| | | | 20 | | | | 25 | | | | | 30 | | | |

| Val | Val | Val | Leu | Asp | Asp | Asn | Asp | Asn | Ala | Pro |
|---|---|---|---|---|---|---|---|---|---|---|
| | | 35 | | | | 40 | | | | |

( 2 ) INFORMATION FOR SEQ ID NO:70:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:70:

```
AAGGGGCTGG ATTATGAGCA GTTCCAGACC CTACAACTGG GAGTGACCGC TAGTGACAGT        60
GGAAACCCAC CATTAAGAAG CAATATTTCA CTGACCCTTT TCGTGCTGGA CCAGAATGAT       120
AACGCCCCAA A                                                            131
```

( 2 ) INFORMATION FOR SEQ ID NO:71:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:71:

| Lys | Gly | Leu | Asp | Tyr | Glu | Gln | Phe | Gln | Thr | Leu | Gln | Leu | Gly | Val | Thr |
|---|---|---|---|---|---|---|---|---|---|---|---|---|---|---|---|
| 1 | | | | 5 | | | | | 10 | | | | | 15 | |

| Ala | Ser | Asp | Ser | Gly | Asn | Pro | Pro | Leu | Arg | Ser | Asn | Ile | Ser | Leu | Thr |
|---|---|---|---|---|---|---|---|---|---|---|---|---|---|---|---|
| | | | 20 | | | | 25 | | | | | 30 | | | |

| Leu | Phe | Val | Leu | Asp | Gln | Asn | Asp | Asn | Ala | Pro |
|---|---|---|---|---|---|---|---|---|---|---|
| | | 35 | | | | 40 | | | | |

( 2 ) INFORMATION FOR SEQ ID NO:72:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:72:

```
AAGCGGGTTG ATTACGAGGA TGTCCAGAAA TACTCGCTGA GCATTAAGGC CCAGGATGGG        60
CGGCCCCCGC TCATCAATTC TTCAGGGGTG GTGTCTGTGC AGGTGCTGGA TGTCAACGAC       120
AATGCCCCGG A                                                            131
```

( 2 ) INFORMATION FOR SEQ ID NO:73:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:73:

Lys Arg Val Asp Tyr Glu Asp Val Gln Lys Tyr Ser Leu Ser Ile Lys
1               5                   10                  15
Ala Gln Asp Gly Arg Pro Pro Leu Ile Asn Ser Ser Gly Val Val Ser
            20                  25                  30
Val Gln Val Leu Asp Val Asn Asp Asn Ala Pro
        35                  40

( 2 ) INFORMATION FOR SEQ ID NO:74:

( i ) SEQUENCE CHARACTERISTICS:
( A ) LENGTH: 125 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:74:

```
AAACCGGTAG ACTTTGAGCT ACAGCAGTTC TATGAAGTAG CTGTGGTGGC TTGGAACTCT        60
GAGGGATTTC ATGTCAAAAG GGTCATTAAA GTGCAACTTT TAGATGACAA CGACAATGCC       120
CCGAT                                                                   125
```

( 2 ) INFORMATION FOR SEQ ID NO:75:

( i ) SEQUENCE CHARACTERISTICS:
( A ) LENGTH: 41 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:75:

Lys Pro Val Asp Phe Glu Leu Gln Gln Phe Tyr Glu Val Ala Val Val
1               5                   10                  15
Ala Trp Asn Ser Glu Gly Phe His Val Lys Arg Val Ile Lys Val Gln
            20                  25                  30
Leu Leu Asp Asp Asn Asp Asn Ala Pro
        35                  40

( 2 ) INFORMATION FOR SEQ ID NO:76:

( i ) SEQUENCE CHARACTERISTICS:
( A ) LENGTH: 125 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:76:

```
AAGGGATTAG ATTTTGAAAC TTTGCCCATT TACACATTGA TAATACAAGG AACTAACATG        60
GCTGGTTTGT CCACTAATAC AACGGTTCTA GTTCACTTGC AGGATGAGAA TGATAACGCC       120
CCAAA                                                                   125
```

( 2 ) INFORMATION FOR SEQ ID NO:77:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:77:

```
Lys Gly Leu Asp Phe Glu Thr Leu Pro Ile Tyr Thr Leu Ile Ile Gln
  1               5                  10                  15
Gly Thr Asn Met Ala Gly Leu Ser Thr Asn Thr Thr Val Leu Val His
              20                  25                  30
Leu Gln Asp Glu Asn Asp Asn Ala Pro
              35                  40
```

( 2 ) INFORMATION FOR SEQ ID NO:78:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:78:

```
AAGCGGGCGG ATTTCGAGGC GATCCGGGAG TACAGTCTGA GGATCAAAGC GCAGGACGGG      60
GGGCGGCCTC CCCTCAGCAA CACCACGGGC ATGGTCACAG TGCAGGTCGT GGACGTCAAT     120
GACAACGCAC CCCT                                                      134
```

( 2 ) INFORMATION FOR SEQ ID NO:79:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:79:

```
Lys Arg Ala Asp Phe Glu Ala Ile Arg Glu Tyr Ser Leu Arg Ile Lys
  1               5                  10                  15
Ala Gln Asp Gly Gly Arg Pro Pro Leu Ser Asn Thr Thr Gly Met Val
              20                  25                  30
Thr Val Gln Val Val Asp Val Asn Asp Asn Ala Pro
              35                  40
```

( 2 ) INFORMATION FOR SEQ ID NO:80:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:80:

```
AAGCGGTTGG ATTACGAAAA GGCATCGGAA TATGAAATCT ATGTTCAAGC CGCTGACAAA      60
GGCGCTGTCC CTATGGCTGG CCATTGCAAA GTGTTGCTGG AGATCGTGGA TGTCAACGAC     120
```

AACGCCCCCT T                                                                                     131

( 2 ) INFORMATION FOR SEQ ID NO:81:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:81:

```
Lys  Arg  Leu  Asp  Tyr  Glu  Lys  Ala  Ser  Glu  Tyr  Glu  Ile  Tyr  Val  Gln
1                   5                        10                       15

Ala  Ala  Asp  Lys  Gly  Ala  Val  Pro  Met  Ala  Gly  His  Cys  Lys  Val  Leu
               20                       25                       30

Leu  Glu  Ile  Val  Asp  Val  Asn  Asp  Asn  Ala  Pro
               35                       40
```

( 2 ) INFORMATION FOR SEQ ID NO:82:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:82:

AAGGGGATCG ATTATGAGGA TCAGGTCTCT TACACATTAG CAGTAACAGC ACATGACTAT         60

GGCATCCCTC AAAAATCAGA CACTACCTAT TTGGAAATCT TAGTAATTGA TGTTAACGAC        120

AACGCGCCCC A                                                             131

( 2 ) INFORMATION FOR SEQ ID NO:83:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:83:

```
Lys  Gly  Ile  Asp  Tyr  Glu  Asp  Gln  Val  Ser  Tyr  Thr  Leu  Ala  Val  Thr
1                   5                        10                       15

Ala  His  Asp  Tyr  Gly  Ile  Pro  Gln  Lys  Ser  Asp  Thr  Thr  Tyr  Leu  Glu
               20                       25                       30

Ile  Leu  Val  Ile  Asp  Val  Asn  Asp  Asn  Ala  Pro
               35                       40
```

( 2 ) INFORMATION FOR SEQ ID NO:84:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:84:

AAAGGGTTAG ATTTCGAGGG CACTAAAGAT TCAGCGTTTA AAATAGTGGC AGCTGACACA         60

GGGAAGCCCA GCCTCAACCA GACAGCCCTG GTGAGAGTAG AGCTGGAGGA TGAGAACGAC    120

AACGCCCCAA T    131

( 2 ) INFORMATION FOR SEQ ID NO:85:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:85:

```
Lys Gly Leu Asp Phe Glu Gly Thr Lys Asp Ser Ala Phe Lys Ile Val
 1               5                  10                  15

Ala Ala Asp Thr Gly Lys Pro Ser Leu Asn Gln Thr Ala Leu Val Arg
            20                  25                  30

Val Glu Leu Glu Asp Glu Asn Asp Asn Ala Pro
            35                  40
```

( 2 ) INFORMATION FOR SEQ ID NO:86:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:86:

AAGGGTGTGG ATTTTGAAAG TGTGCGTAGC TACAGGCTGG TTATTCGTGC TCAAGATGGA    60

GGCAGCCCCT CCAGAAGTAA CACCACCCAG CTCTTGGTCA ACGTCATCGA TCGAATGACA    120

ATGCGCCGCT    130

( 2 ) INFORMATION FOR SEQ ID NO:87:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:87:

```
Lys Gly Val Asp Phe Glu Ser Val Arg Ser Tyr Arg Leu Val Ile Arg
 1               5                  10                  15

Ala Gln Asp Gly Gly Ser Pro Ser Arg Ser Asn Thr Thr Gln Leu Leu
            20                  25                  30

Val Asn Val Ile Asp Val Asn Asp Asn Ala Pro
            35                  40
```

( 2 ) INFORMATION FOR SEQ ID NO:88:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:88:

```
AAGGGTGTGG  ACTTCGAGCT  GACACATCTG  TATGAGATTT  GGATTGAGGC  TGCCGATGGA        60

GACACGCCAA  GTCTGCGTAG  TGTAACTCTT  ATAACGCTCA  ACGTAACGGA  TGCCAATGAC       120

AATGCTCCCA  A                                                                131
```

( 2 ) INFORMATION FOR SEQ ID NO:89:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:89:

```
Lys  Gly  Val  Asp  Phe  Glu  Leu  Thr  His  Leu  Tyr  Glu  Ile  Trp  Ile  Glu
 1              5                        10                        15

Ala  Ala  Asp  Gly  Asp  Thr  Pro  Ser  Leu  Arg  Ser  Val  Thr  Leu  Ile  Thr
            20                        25                        30

Leu  Asn  Val  Thr  Asp  Ala  Asn  Asp  Asn  Ala  Pro
            35                        40
```

( 2 ) INFORMATION FOR SEQ ID NO:90:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:90:

```
CAAGGCGTTT  GATTTGAAG   AGACAAGTAG  ATATGTGTTG  AGTGTGGAAG  CTAAGGATGG        60

AGGAGTACAC  ACAGCTCACT  GTAATGTTCA  AATAGAAATT  GTTGACGAGA  ATGACAATGC       120

CCCAGAGGTG  ACATTCATGT  CCTTCTCTAA  CCAGATTCCA  GAGGATTCAG  ACCTTGGAAC       180

TGTAATAGCC  CTCATAAAAG  TGCGAGACAA  GGATTCTGGG  CAAAATGGCA  TGGTGACATG       240

CTATACTCAG  GAAGAAGTTC  CTTTCAAATT  AGAATCCACC  TCGAAGAATT  ATTACAAGCT       300

GGTGATTGCT  GGAGCCCTAA  ACCGGGAGCA  GACAGCAGAC  TACAACGTCA  CAATCATAGC       360

CACCGACAAG  GGCAAACCAG  CCCTTTCCTC  CAGGACAAGC  ATCACCCTGC  ACATCTCCGA       420

CATCAACGAT  AATGCCCCCG  T                                                   441
```

( 2 ) INFORMATION FOR SEQ ID NO:91:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:91:

```
Lys  Ala  Phe  Asp  Phe  Glu  Glu  Thr  Ser  Arg  Tyr  Val  Leu  Ser  Val  Glu
 1              5                        10                        15

Ala  Lys  Asp  Gly  Gly  Val  His  Thr  Ala  His  Cys  Asn  Val  Gln  Ile  Glu
            20                        25                        30

Ile  Val  Asp  Glu  Asn  Asp  Asn  Ala  Pro  Glu  Val  Thr  Phe  Met  Ser  Phe
            35                        40                        45

Ser  Asn  Gln  Ile  Pro  Glu  Asp  Ser  Asp  Leu  Gly  Thr  Val  Ile  Ala  Leu
```

5,798,224

|     |     |     |     | 50  |     |     |     |     | 55  |     |     |     |     | 60  |     |     |
| --- | --- | --- | --- | --- | --- | --- | --- | --- | --- | --- | --- | --- | --- | --- | --- | --- |
| Ile | Lys | Val | Arg | Asp | Lys | Asp | Ser | Gly | Gln | Asn | Gly | Met | Val | Thr | Cys |
| 65  |     |     |     |     | 70  |     |     |     |     | 75  |     |     |     |     | 80  |
| Tyr | Thr | Gln | Glu | Glu | Val | Pro | Phe | Lys | Leu | Glu | Ser | Thr | Ser | Lys | Asn |
|     |     |     |     | 85  |     |     |     |     | 90  |     |     |     |     | 95  |     |
| Tyr | Tyr | Lys | Leu | Val | Ile | Ala | Gly | Ala | Leu | Asn | Arg | Glu | Gln | Thr | Ala |
|     |     |     |     | 100 |     |     |     |     | 105 |     |     |     |     | 110 |     |
| Asp | Tyr | Asn | Val | Thr | Ile | Ile | Ala | Thr | Asp | Lys | Gly | Lys | Pro | Ala | Leu |
|     |     |     | 115 |     |     |     |     | 120 |     |     |     |     | 125 |     |     |
| Ser | Ser | Arg | Thr | Ser | Ile | Thr | Leu | His | Ile | Ser | Asp | Ile | Asn | Asp | Asn |
|     |     |     | 130 |     |     |     | 135 |     |     |     |     | 140 |     |     |     |
| Ala | Pro |
| 145 |     |

( 2 ) INFORMATION FOR SEQ ID NO:92:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:92:

```
AAGCGAGTGG ATTACGAGGC CACTCGGAAT TATAAGCTGA GAGTTAAGGC TACTGATCTT      60
GGGATTCCAC CGAGATCTTC TAACATGACA CTGTTCATTC ATGTCCTTGA TGTTAACGAC     120
AACGCTCCCT T                                                          131
```

( 2 ) INFORMATION FOR SEQ ID NO:93:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:93:

|     |     |     |     | 5   |     |     |     |     | 10  |     |     |     |     | 15  |     |
| --- | --- | --- | --- | --- | --- | --- | --- | --- | --- | --- | --- | --- | --- | --- | --- |
| Lys | Arg | Val | Asp | Tyr | Glu | Ala | Thr | Arg | Asn | Tyr | Lys | Leu | Arg | Val | Lys |
| 1   |     |     |     | 5   |     |     |     |     | 10  |     |     |     |     | 15  |     |
| Ala | Thr | Asp | Leu | Gly | Ile | Pro | Pro | Arg | Ser | Ser | Asn | Met | Thr | Leu | Phe |
|     |     |     | 20  |     |     |     |     | 25  |     |     |     |     | 30  |     |     |
| Ile | His | Val | Leu | Asp | Val | Asn | Asp | Asn | Ala | Pro |
|     |     | 35  |     |     |     |     | 40  |     |     |     |

( 2 ) INFORMATION FOR SEQ ID NO:94:

( i ) SEQUENCE CHARACTERISTICS:
        ( A ) LENGTH: 4104 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 495..3572

( x i ) SEQUENCE DESCRIPTION: SEQ ID NO:94:

```
CCTCTATTCG ACATTCTCTT TGGATTGTTT TGCTATAACT TGAAATTTGG GATGTCACAA      60
```

-continued

```
ACGAAACTGT CATCTGTTTC CGCCAAACTG TGGTTCTGCT AATCTCCCAG GCTGGCAGCA         120

TTGGAGACTT GCTGACTTCT TTCATCCCCC ACTCTTTTCA CCTGAAATTC CTTTCCTTGG         180

TTTTGCTCTA AGTCCTATGC TTCAGTCAGG GGCCAACCAA ATCTCACTGC CTCCTTTTTA         240

TCATGAAGCC TTTGATCACT GATAGTTCTT TTTATATCTT GAAAAATCAC CCTTCCCAGT         300

ACAGTTAATA TTTAGTATCT CTACTCATCT TGGCACTTAC TCACAGCTCC ATAATTCAGT         360

CGTTTTCGTA CCTCTTCATG GTGATGGGGA GCCCTTTGGA GGTGGTGACT GTGCTTATA          420

CTCCTCATGA TGCTTCACAT GTGGCAGGCG TGGAGTGCCC GGAGGCGGCC CTCCTGATTC         480

TGGGGCCTCC CAGG ATG GAG CCC CTG AGG CAC AGC CCA GGC CCT GGG GGG          530
              Met Glu Pro Leu Arg His Ser Pro Gly Pro Gly Gly
               1             5                  10

CAA CGG CTA CTG CTG CCC TCC ATG CTG CTA GCA CTG CTG CTC CTG CTG           578
Gln Arg Leu Leu Leu Pro Ser Met Leu Leu Ala Leu Leu Leu Leu Leu
         15              20                  25

GCT CCA TCC CCA GGC CAC GCC ACT CGG GTA GTG TAC AAG GTG CCG GAG           626
Ala Pro Ser Pro Gly His Ala Thr Arg Val Val Tyr Lys Val Pro Glu
     30              35                  40

GAA CAG CCA CCC AAC ACC CTC ATT GGG AGC CTC GCA GCC GAC TAT GGT           674
Glu Gln Pro Pro Asn Thr Leu Ile Gly Ser Leu Ala Ala Asp Tyr Gly
 45              50                  55                  60

TTT CCA GAT GTG GGG CAC CTG TAC AAG CTA GAG GTG GGT GCC CCG TAC           722
Phe Pro Asp Val Gly His Leu Tyr Lys Leu Glu Val Gly Ala Pro Tyr
             65                  70                  75

CTT CGC GTG GAT GGC AAG ACA GGT GAC ATT TTC ACC ACC GAG ACC TCC           770
Leu Arg Val Asp Gly Lys Thr Gly Asp Ile Phe Thr Thr Glu Thr Ser
             80                  85                  90

ATC GAC CGT GAG GGG CTC CGT GAA TGC CAG AAC CAG CTC CCT GGT GAT           818
Ile Asp Arg Glu Gly Leu Arg Glu Cys Gln Asn Gln Leu Pro Gly Asp
             95                 100                 105

CCC TGC ATC CTG GAG TTT GAG GTA TCT ATC ACA GAC CTC GTG CAG AAT           866
Pro Cys Ile Leu Glu Phe Glu Val Ser Ile Thr Asp Leu Val Gln Asn
 110                 115                 120

GCG AGC CCC CGG CTG CTA GAG GGC CAG ATA GAA GTA CAA GAC ATC AAT           914
Ala Ser Pro Arg Leu Leu Glu Gly Gln Ile Glu Val Gln Asp Ile Asn
 125                 130                 135                 140

GAC AAC ACA CCC AAC TTC GCC TCA CCA GTC ATC ACT CTG GCC ATC CCT           962
Asp Asn Thr Pro Asn Phe Ala Ser Pro Val Ile Thr Leu Ala Ile Pro
                 145                 150                 155

GAG AAC ACC AAC ATC GGC TCA CTC TTC CCC ATC CCG CTG GCT TCA GAC          1010
Glu Asn Thr Asn Ile Gly Ser Leu Phe Pro Ile Pro Leu Ala Ser Asp
                 160                 165                 170

CGT GAT GCT GGT CCC AAC GGT GTG GCA TCC TAT GAG CTG CAG GTG GCA          1058
Arg Asp Ala Gly Pro Asn Gly Val Ala Ser Tyr Glu Leu Gln Val Ala
         175                 180                 185

GAG GAC CAG GAG GAG AAG CAA CCA CAG CTC ATT GTG ATG GGC AAC CTG          1106
Glu Asp Gln Glu Glu Lys Gln Pro Gln Leu Ile Val Met Gly Asn Leu
 190                 195                 200

GAC CGT GAG CGC TGG GAC TCC TAT GAC CTC ACC ATC AAG GTG CAG GAT          1154
Asp Arg Glu Arg Trp Asp Ser Tyr Asp Leu Thr Ile Lys Val Gln Asp
 205                 210                 215                 220

GGC GGC AGC CCC CCA CGC GCC ACG AGT GCC CTG CTG CGT GTC ACC GTG          1202
Gly Gly Ser Pro Pro Arg Ala Thr Ser Ala Leu Leu Arg Val Thr Val
                 225                 230                 235

CTT GAC ACC AAT GAC AAC GCC CCC AAG TTT GAG CGG CCC TCC TAT GAG          1250
Leu Asp Thr Asn Asp Asn Ala Pro Lys Phe Glu Arg Pro Ser Tyr Glu
                 240                 245                 250

GCC GAA CTA TCT GAG AAT AGC CCC ATA GGC CAC TCG GTC ATC CAG GTG          1298
Ala Glu Leu Ser Glu Asn Ser Pro Ile Gly His Ser Val Ile Gln Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 255 |     |     |     |     | 260 |     |     |     |     |     | 265 |     |     |      |
| AAG | GCC | AAT | GAC | TCA | GAC | CAA | GGT | GCC | AAT | GCA | GAA | ATC | GAA | TAC | ACA | 1346 |
| Lys | Ala | Asn | Asp | Ser | Asp | Gln | Gly | Ala | Asn | Ala | Glu | Ile | Glu | Tyr | Thr |      |
|     |     | 270 |     |     |     | 275 |     |     |     |     | 280 |     |     |     |     |      |
| TTC | CAC | CAG | GCG | CCC | GAA | GTT | GTG | AGG | CGT | CTT | CTT | CGA | CTG | GAC | AGG | 1394 |
| Phe | His | Gln | Ala | Pro | Glu | Val | Val | Arg | Arg | Leu | Leu | Arg | Leu | Asp | Arg |      |
| 285 |     |     |     |     | 290 |     |     |     |     | 295 |     |     |     |     | 300 |      |
| AAC | ACT | GGA | CTT | ATC | ACT | GTT | CAG | GGC | CCG | GTG | GAC | CGT | GAG | GAC | CTA | 1442 |
| Asn | Thr | Gly | Leu | Ile | Thr | Val | Gln | Gly | Pro | Val | Asp | Arg | Glu | Asp | Leu |      |
|     |     |     |     | 305 |     |     |     |     | 310 |     |     |     |     | 315 |     |      |
| AGC | ACC | CTG | CGC | TTC | TCA | GTG | CTT | GCT | AAG | GAC | CGA | GGC | ACC | AAC | CCC | 1490 |
| Ser | Thr | Leu | Arg | Phe | Ser | Val | Leu | Ala | Lys | Asp | Arg | Gly | Thr | Asn | Pro |      |
|     |     |     | 320 |     |     |     |     | 325 |     |     |     |     | 330 |     |     |      |
| AAG | AGT | GCC | CGT | GCC | CAG | GTG | GTT | GTG | ACC | GTG | AAG | GAC | ATG | AAT | GAC | 1538 |
| Lys | Ser | Ala | Arg | Ala | Gln | Val | Val | Val | Thr | Val | Lys | Asp | Met | Asn | Asp |      |
|     |     | 335 |     |     |     |     | 340 |     |     |     |     | 345 |     |     |     |      |
| AAT | GCC | CCC | ACC | ATT | GAG | ATC | CGG | GGC | ATA | GGG | CTA | GTG | ACT | CAT | CAA | 1586 |
| Asn | Ala | Pro | Thr | Ile | Glu | Ile | Arg | Gly | Ile | Gly | Leu | Val | Thr | His | Gln |      |
| 350 |     |     |     |     | 355 |     |     |     |     | 360 |     |     |     |     |     |      |
| GAT | GGG | ATG | GCT | AAC | ATC | TCA | GAG | GAT | GTG | GCA | GAG | GAG | ACA | GCT | GTG | 1634 |
| Asp | Gly | Met | Ala | Asn | Ile | Ser | Glu | Asp | Val | Ala | Glu | Glu | Thr | Ala | Val |      |
| 365 |     |     |     |     | 370 |     |     |     |     | 375 |     |     |     |     | 380 |      |
| GCC | CTG | GTG | CAG | GTG | TCT | GAC | CGA | GAT | GAG | GGA | GAG | AAT | GCA | GCT | GTC | 1682 |
| Ala | Leu | Val | Gln | Val | Ser | Asp | Arg | Asp | Glu | Gly | Glu | Asn | Ala | Ala | Val |      |
|     |     |     |     | 385 |     |     |     |     | 390 |     |     |     |     | 395 |     |      |
| ACC | TGT | GTG | GTG | GCA | GGT | GAT | GTG | CCC | TTC | CAG | CTG | CGC | CAG | GCC | AGT | 1730 |
| Thr | Cys | Val | Val | Ala | Gly | Asp | Val | Pro | Phe | Gln | Leu | Arg | Gln | Ala | Ser |      |
|     |     |     | 400 |     |     |     |     | 405 |     |     |     |     | 410 |     |     |      |
| GAG | ACA | GGC | AGT | GAC | AGC | AAG | AAG | AAG | TAT | TTC | CTG | CAG | ACT | ACC | ACC | 1778 |
| Glu | Thr | Gly | Ser | Asp | Ser | Lys | Lys | Lys | Tyr | Phe | Leu | Gln | Thr | Thr | Thr |      |
|     |     | 415 |     |     |     |     | 420 |     |     |     |     | 425 |     |     |     |      |
| CCG | CTA | GAC | TAC | GAG | AAG | GTC | AAA | GAC | TAC | ACC | ATT | GAG | ATT | GTG | GCT | 1826 |
| Pro | Leu | Asp | Tyr | Glu | Lys | Val | Lys | Asp | Tyr | Thr | Ile | Glu | Ile | Val | Ala |      |
|     | 430 |     |     |     |     | 435 |     |     |     |     | 440 |     |     |     |     |      |
| GTG | GAC | TCT | GGC | AAC | CCC | CCA | CTC | TCC | AGC | ACT | AAC | TCC | CTC | AAG | GTG | 1874 |
| Val | Asp | Ser | Gly | Asn | Pro | Pro | Leu | Ser | Ser | Thr | Asn | Ser | Leu | Lys | Val |      |
| 445 |     |     |     |     | 450 |     |     |     |     | 455 |     |     |     |     | 460 |      |
| CAG | GTG | GTG | GAC | GTC | AAT | GAC | AAC | GCA | CCT | GTC | TTC | ACT | CAG | AGT | GTC | 1922 |
| Gln | Val | Val | Asp | Val | Asn | Asp | Asn | Ala | Pro | Val | Phe | Thr | Gln | Ser | Val |      |
|     |     |     |     | 465 |     |     |     |     | 470 |     |     |     |     | 475 |     |      |
| ACT | GAG | GTC | GCC | TTC | CCG | GAA | AAC | AAC | AAG | CCT | GGT | GAA | GTG | ATT | GCT | 1970 |
| Thr | Glu | Val | Ala | Phe | Pro | Glu | Asn | Asn | Lys | Pro | Gly | Glu | Val | Ile | Ala |      |
|     |     |     | 480 |     |     |     |     | 485 |     |     |     |     | 490 |     |     |      |
| GAG | ATC | ACT | GCC | AGT | GAT | GCT | GAC | TCT | GGC | TCT | AAT | GCT | GAG | CTG | GTT | 2018 |
| Glu | Ile | Thr | Ala | Ser | Asp | Ala | Asp | Ser | Gly | Ser | Asn | Ala | Glu | Leu | Val |      |
|     |     | 495 |     |     |     |     | 500 |     |     |     |     | 505 |     |     |     |      |
| TAC | TCT | CTG | GAG | CCT | GAG | CCG | GCT | GCT | AAG | GGC | CTC | TTC | ACC | ATC | TCA | 2066 |
| Tyr | Ser | Leu | Glu | Pro | Glu | Pro | Ala | Ala | Lys | Gly | Leu | Phe | Thr | Ile | Ser |      |
| 510 |     |     |     |     | 515 |     |     |     |     | 520 |     |     |     |     |     |      |
| CCC | GAG | ACT | GGA | GAG | ATC | CAG | GTG | AAG | ACA | TCT | CTG | GAT | CGG | GAA | CAG | 2114 |
| Pro | Glu | Thr | Gly | Glu | Ile | Gln | Val | Lys | Thr | Ser | Leu | Asp | Arg | Glu | Gln |      |
| 525 |     |     |     |     | 530 |     |     |     |     | 535 |     |     |     |     | 540 |      |
| CGG | GAG | AGC | TAT | GAG | TTG | AAG | GTG | GTG | GCA | GCT | GAC | CGG | GGC | AGT | CCT | 2162 |
| Arg | Glu | Ser | Tyr | Glu | Leu | Lys | Val | Val | Ala | Ala | Asp | Arg | Gly | Ser | Pro |      |
|     |     |     |     | 545 |     |     |     |     | 550 |     |     |     |     | 555 |     |      |
| AGC | CTC | CAG | GGC | ACA | GCC | ACT | GTC | CTT | GTC | AAT | GTG | CTG | GAC | TGC | AAT | 2210 |
| Ser | Leu | Gln | Gly | Thr | Ala | Thr | Val | Leu | Val | Asn | Val | Leu | Asp | Cys | Asn |      |
|     |     |     | 560 |     |     |     |     | 565 |     |     |     |     | 570 |     |     |      |
| GAC | AAT | GAC | CCC | AAA | TTT | ATG | CTG | AGT | GGC | TAC | AAC | TTC | TCA | GTG | ATG | 2258 |
| Asp | Asn | Asp | Pro | Lys | Phe | Met | Leu | Ser | Gly | Tyr | Asn | Phe | Ser | Val | Met |      |

```
                575                          580                          585

GAG AAC ATG CCA GCA CTG AGT CCA GTG GGC ATG GTG ACT GTC ATT GAT          2306
Glu Asn Met Pro Ala Leu Ser Pro Val Gly Met Val Thr Val Ile Asp
    590                 595                 600

GGA GAC AAG GGG GAG AAT GCC CAG GTG CAG CTC TCA GTG GAG CAG GAC          2354
Gly Asp Lys Gly Glu Asn Ala Gln Val Gln Leu Ser Val Glu Gln Asp
605                 610                 615                 620

AAC GGT GAC TTT GTT ATC CAG AAT GGC ACA GGC ACC ATC CTA TCC AGC          2402
Asn Gly Asp Phe Val Ile Gln Asn Gly Thr Gly Thr Ile Leu Ser Ser
                625                 630                 635

CTG AGC TTT GAT CGA GAG CAA CAA AGC ACC TAC ACC TTC CAG CTG AAG          2450
Leu Ser Phe Asp Arg Glu Gln Gln Ser Thr Tyr Thr Phe Gln Leu Lys
            640                 645                 650

GCA GTG GAT GGT GGC GTC CCA CCT CGC TCA GCT TAC GTT GGT GTC ACC          2498
Ala Val Asp Gly Gly Val Pro Pro Arg Ser Ala Tyr Val Gly Val Thr
        655                 660                 665

ATC AAT GTG CTG GAC GAG AAT GAC AAC GCA CCC TAT ATC ACT GCC CCT          2546
Ile Asn Val Leu Asp Glu Asn Asp Asn Ala Pro Tyr Ile Thr Ala Pro
    670                 675                 680

TCT AAC ACC TCT CAC AAG CTG CTG ACC CCC CAG ACA CGT CTT GGT GAG          2594
Ser Asn Thr Ser His Lys Leu Leu Thr Pro Gln Thr Arg Leu Gly Glu
685                 690                 695                 700

ACG GTC AGC CAG GTG GCA GCC GAG GAC TTT GAC TCT GGT GTC AAT GCC          2642
Thr Val Ser Gln Val Ala Ala Glu Asp Phe Asp Ser Gly Val Asn Ala
                705                 710                 715

GAG CTG ATC TAC AGC ATT GCA GGT GGC AAC CCT TAT GGA CTC TTC CAG          2690
Glu Leu Ile Tyr Ser Ile Ala Gly Gly Asn Pro Tyr Gly Leu Phe Gln
            720                 725                 730

ATT GGG TCA CAT TCA GGT GCC ATC ACC CTG GAG AAG GAG ATT GAG CGG          2738
Ile Gly Ser His Ser Gly Ala Ile Thr Leu Glu Lys Glu Ile Glu Arg
        735                 740                 745

CGC CAC CAT GGG CTA CAC CGC CTG GTG GTG AAG GTC AGT GAC CGC GGC          2786
Arg His His Gly Leu His Arg Leu Val Val Lys Val Ser Asp Arg Gly
    750                 755                 760

AAG CCC CCA CGC TAT GGC ACA GCC TTG GTC CAT CTT TAT GTC AAT GAG          2834
Lys Pro Pro Arg Tyr Gly Thr Ala Leu Val His Leu Tyr Val Asn Glu
765                 770                 775                 780

ACT CTG GCC AAC CGC ACG CTG CTG GAG ACC CTC CTG GGC CAC AGC CTG          2882
Thr Leu Ala Asn Arg Thr Leu Leu Glu Thr Leu Leu Gly His Ser Leu
                785                 790                 795

GAC ACG CCG CTG GAT ATT GAC ATT GCT GGG GAT CCA GAA TAT GAG CGC          2930
Asp Thr Pro Leu Asp Ile Asp Ile Ala Gly Asp Pro Glu Tyr Glu Arg
            800                 805                 810

TCC AAG CAG CGT GGC AAC ATT CTC TTT GGT GTG GTG GCT GGT GTG GTG          2978
Ser Lys Gln Arg Gly Asn Ile Leu Phe Gly Val Val Ala Gly Val Val
        815                 820                 825

GCC GTG GCC TTG CTC ATC GCC CTG GCG GTT CTT GTG CGC TAC TGC AGA          3026
Ala Val Ala Leu Leu Ile Ala Leu Ala Val Leu Val Arg Tyr Cys Arg
    830                 835                 840

CAG CGG GAG GCC AAA AGT GGT TAC CAG GCT GGT AAG AAG GAG ACC AAG          3074
Gln Arg Glu Ala Lys Ser Gly Tyr Gln Ala Gly Lys Lys Glu Thr Lys
845                 850                 855                 860

GAC CTG TAT GCC CCC AAG CCC AGT GGC AAG GCC TCC AAG GGA AAC AAA          3122
Asp Leu Tyr Ala Pro Lys Pro Ser Gly Lys Ala Ser Lys Gly Asn Lys
                865                 870                 875

AGC AAA GGC AAG AAG AGC AAG TCC CCA AAG CCC GTG AAG CCA GTG GAG          3170
Ser Lys Gly Lys Lys Ser Lys Ser Pro Lys Pro Val Lys Pro Val Glu
            880                 885                 890

GAC GAG GAT GAG GCC GGG CTG CAG AAG TCC CTC AAG TTC AAC CTG ATG          3218
Asp Glu Asp Glu Ala Gly Leu Gln Lys Ser Leu Lys Phe Asn Leu Met
```

|     |     |     |     |     |     |     |     |     |     |     |     |     |     |     |     |      |
|---|---|---|---|---|---|---|---|---|---|---|---|---|---|---|---|---|
|     | 895 |     |     |     |     | 900 |     |     |     |     | 905 |     |     |     |     |      |
| AGC | GAT | GCC | CCT | GGG | GAC | AGT | CCC | CGC | ATC | CAC | CTG | CCC | CTC | AAC | TAC | 3266 |
| Ser | Asp | Ala | Pro | Gly | Asp | Ser | Pro | Arg | Ile | His | Leu | Pro | Leu | Asn | Tyr |      |
|     | 910 |     |     |     |     | 915 |     |     |     |     | 920 |     |     |     |     |      |
| CCA | CCA | GGC | AGC | CCT | GAC | CTG | GGC | CGC | CAC | TAT | CGC | TCT | AAC | TCC | CCA | 3314 |
| Pro | Pro | Gly | Ser | Pro | Asp | Leu | Gly | Arg | His | Tyr | Arg | Ser | Asn | Ser | Pro |      |
| 925 |     |     |     |     | 930 |     |     |     |     | 935 |     |     |     |     | 940 |      |
| CTG | CCT | TCC | ATC | CAG | CTG | CAG | CCC | CAG | TCA | CCC | TCA | GCC | TCC | AAG | AAG | 3362 |
| Leu | Pro | Ser | Ile | Gln | Leu | Gln | Pro | Gln | Ser | Pro | Ser | Ala | Ser | Lys | Lys |      |
|     |     |     |     | 945 |     |     |     |     | 950 |     |     |     |     | 955 |     |      |
| CAC | CAG | GTG | GTA | CAG | GAC | CTG | CCA | CCT | GCA | AAC | ACA | TTC | GTG | GGC | ACC | 3410 |
| His | Gln | Val | Val | Gln | Asp | Leu | Pro | Pro | Ala | Asn | Thr | Phe | Val | Gly | Thr |      |
|     |     |     | 960 |     |     |     |     | 965 |     |     |     |     | 970 |     |     |      |
| GGG | GAC | ACC | ACG | TCC | ACG | GGC | TCT | GAG | CAG | TAC | TCC | GAC | TAC | AGC | TAC | 3458 |
| Gly | Asp | Thr | Thr | Ser | Thr | Gly | Ser | Glu | Gln | Tyr | Ser | Asp | Tyr | Ser | Tyr |      |
|     |     | 975 |     |     |     |     | 980 |     |     |     |     | 985 |     |     |     |      |
| CGC | ACC | AAC | CCC | CCC | AAA | TAC | CCC | AGC | AAG | CAG | GTA | GGC | CAG | CCC | TTT | 3506 |
| Arg | Thr | Asn | Pro | Pro | Lys | Tyr | Pro | Ser | Lys | Gln | Val | Gly | Gln | Pro | Phe |      |
|     | 990 |     |     |     |     | 995 |     |     |     | 1000|     |     |     |     |     |      |
| CAG | CTC | AGC | ACA | CCC | CAG | CCC | CTA | CCC | CAC | CCC | TAC | CAC | GGA | GCC | ATC | 3554 |
| Gln | Leu | Ser | Thr | Pro | Gln | Pro | Leu | Pro | His | Pro | Tyr | His | Gly | Ala | Ile |      |
| 1005|     |     |     |     | 1010|     |     |     |     | 1015|     |     |     |     | 1020|      |
| TGG | ACC | GAG | GTG | TGG | GAG | TGATGGAGCA | GGTTTACTGT | GCCTGCCCGT |     |     |     |     |     |     |     | 3602 |
| Trp | Thr | Glu | Val | Trp | Glu |     |     |     |     |     |     |     |     |     |     |      |
|     |     |     |     | 1025|     |     |     |     |     |     |     |     |     |     |     |      |

| | | | |
|---|---|---|---|
| GTTGGGGGCC | AGCCTGAGCC | AGCAGTGGGA | GGTGGGGCCT | TAGTGCCTCA | CCGGGCACAC | 3662 |
| GGATTAGGCT | GAGTGAAGAT | TAAGGGAGGG | TGTGCTCTGT | GGTCTCCTCC | CTGCCCTCTC | 3722 |
| CCCACTGGGG | AGAGACCTGT | GATTTGCCAA | GTCCCTGGAC | CCTGGACCAG | CTACTGGGCC | 3782 |
| TTATGGGTTG | GGGGTGGTAG | GCAGGTGAGC | GTAAGTGGGG | AGGGAAATGG | GTAAGAAGTC | 3842 |
| TACTCCAAAC | CTAGGTCTCT | ATGTCAGACC | AGACCTAGGT | GCTTCTCTAG | GAGGGAAACA | 3902 |
| GGGAGACCTG | GGGTCCTGTG | GATAACTGAG | TGGGGAGTCT | GCCAGGGGAG | GGCACCTTCC | 3962 |
| CATTGTGCCT | TCTGTGTGTA | TTGTGCATTA | ACCTCTTCCT | CACCACTAGG | CTTCTGGGGC | 4022 |
| TGGGTCCCAC | ATGCCCTTGA | CCCTGACAAT | AAAGTTCTCT | ATTTTTGGAA | AAAAAAAAA | 4082 |
| AAAAAAAAAA | AAAAAAAAAA | AA | | | | 4104 |

( 2 ) INFORMATION FOR SEQ ID NO:95:

( i ) SEQUENCE CHARACTERISTICS:
        ( A ) LENGTH: 1026 amino acids
        ( B ) TYPE: amino acid
        ( D ) TOPOLOGY: linear ( i i ) MOLECULE TYPE: protein ( x i ) SEQUENCE DESCRIPTION: SEQ ID NO:95:

| | | | | | | | | | | | | | | |
|---|---|---|---|---|---|---|---|---|---|---|---|---|---|---|
| Met | Glu | Pro | Leu | Arg | His | Ser | Pro | Gly | Pro | Gly | Gly | Gln | Arg | Leu | Leu |
| 1 | | | | 5 | | | | | 10 | | | | | 15 | |
| Leu | Pro | Ser | Met | Leu | Leu | Ala | Leu | Leu | Leu | Leu | Ala | Pro | Ser | Pro |
| | | | 20 | | | | 25 | | | | | 30 | | |
| Gly | His | Ala | Thr | Arg | Val | Val | Tyr | Lys | Val | Pro | Glu | Gln | Pro | Pro |
| | | 35 | | | | 40 | | | | | 45 | | | |
| Asn | Thr | Leu | Ile | Gly | Ser | Leu | Ala | Ala | Asp | Tyr | Gly | Phe | Pro | Asp | Val |
| | 50 | | | | | 55 | | | | | 60 | | | | |
| Gly | His | Leu | Tyr | Lys | Leu | Glu | Val | Gly | Ala | Pro | Tyr | Leu | Arg | Val | Asp |
| 65 | | | | | 70 | | | | | 75 | | | | | 80 |
| Gly | Lys | Thr | Gly | Asp | Ile | Phe | Thr | Thr | Glu | Thr | Ser | Ile | Asp | Arg | Glu |

-continued

```
                    85                              90                              95
Gly Leu Arg Glu Cys Gln Asn Gln Leu Pro Gly Asp Pro Cys Ile Leu
            100                 105                 110
Glu Phe Glu Val Ser Ile Thr Asp Leu Val Gln Asn Ala Ser Pro Arg
        115                 120                 125
Leu Leu Glu Gly Gln Ile Glu Val Gln Asp Ile Asn Asp Thr Pro
    130                 135                 140
Asn Phe Ala Ser Pro Val Ile Thr Leu Ala Ile Pro Glu Asn Thr Asn
145                 150                 155                 160
Ile Gly Ser Leu Phe Pro Ile Pro Leu Ala Ser Arg Asp Ala Gly
                165                 170                 175
Pro Asn Gly Val Ala Ser Tyr Glu Leu Gln Val Ala Glu Asp Gln Glu
            180                 185                 190
Glu Lys Gln Pro Gln Leu Ile Val Met Gly Asn Leu Asp Arg Glu Arg
        195                 200                 205
Trp Asp Ser Tyr Asp Leu Thr Ile Lys Val Gln Asp Gly Gly Ser Pro
    210                 215                 220
Pro Arg Ala Thr Ser Ala Leu Leu Arg Val Thr Val Leu Asp Thr Asn
225                 230                 235                 240
Asp Asn Ala Pro Lys Phe Glu Arg Pro Ser Tyr Glu Ala Glu Leu Ser
                245                 250                 255
Glu Asn Ser Pro Ile Gly His Ser Val Ile Gln Val Lys Ala Asn Asp
            260                 265                 270
Ser Asp Gln Gly Ala Asn Ala Glu Ile Glu Tyr Thr Phe His Gln Ala
        275                 280                 285
Pro Glu Val Val Arg Arg Leu Leu Arg Leu Asp Arg Asn Thr Gly Leu
    290                 295                 300
Ile Thr Val Gln Gly Pro Val Asp Arg Glu Asp Leu Ser Thr Leu Arg
305                 310                 315                 320
Phe Ser Val Leu Ala Lys Asp Arg Gly Thr Asn Pro Lys Ser Ala Arg
                325                 330                 335
Ala Gln Val Val Val Thr Val Lys Asp Met Asn Asp Asn Ala Pro Thr
            340                 345                 350
Ile Glu Ile Arg Gly Ile Gly Leu Val Thr His Gln Asp Gly Met Ala
        355                 360                 365
Asn Ile Ser Glu Asp Val Ala Glu Glu Thr Ala Val Ala Leu Val Gln
    370                 375                 380
Val Ser Asp Arg Asp Glu Gly Glu Asn Ala Ala Val Thr Cys Val Val
385                 390                 395                 400
Ala Gly Asp Val Pro Phe Gln Leu Arg Gln Ala Ser Glu Thr Gly Ser
                405                 410                 415
Asp Ser Lys Lys Lys Tyr Phe Leu Gln Thr Thr Thr Pro Leu Asp Tyr
            420                 425                 430
Glu Lys Val Lys Asp Tyr Thr Ile Glu Ile Val Ala Val Asp Ser Gly
        435                 440                 445
Asn Pro Pro Leu Ser Ser Thr Asn Ser Leu Lys Val Gln Val Val Asp
    450                 455                 460
Val Asn Asp Asn Ala Pro Val Phe Thr Gln Ser Val Thr Glu Val Ala
465                 470                 475                 480
Phe Pro Glu Asn Asn Lys Pro Gly Glu Val Ile Ala Glu Ile Thr Ala
                485                 490                 495
Ser Asp Ala Asp Ser Gly Ser Asn Ala Glu Leu Val Tyr Ser Leu Glu
            500                 505                 510
```

| | | | | | | | | | | | | | | |
|---|---|---|---|---|---|---|---|---|---|---|---|---|---|---|
| Pro | Glu | Pro<br>515 | Ala | Ala | Lys | Gly | Leu | Phe | Thr | Ile | Ser | Pro<br>525 | Glu | Thr | Gly |
| Glu | Ile<br>530 | Gln | Val | Lys | Thr | Ser<br>535 | Leu | Asp | Arg | Glu | Gln<br>540 | Arg | Glu | Ser | Tyr |
| Glu<br>545 | Leu | Lys | Val | Val | Ala<br>550 | Ala | Asp | Arg | Gly | Ser<br>555 | Pro | Ser | Leu | Gln | Gly<br>560 |
| Thr | Ala | Thr | Val | Leu<br>565 | Val | Asn | Val | Leu | Asp<br>570 | Cys | Asn | Asp | Asn<br>575 | | Pro |
| Lys | Phe | Met | Leu<br>580 | Ser | Gly | Tyr | Asn | Phe<br>585 | Ser | Val | Met | Glu<br>590 | Asn | Met | Pro |
| Ala | Leu | Ser<br>595 | Pro | Val | Gly | Met | Val<br>600 | Thr | Val | Ile | Asp<br>605 | Gly | Asp | Lys | Gly |
| Glu | Asn<br>610 | Ala | Gln | Val | Gln | Leu<br>615 | Ser | Val | Glu | Gln<br>620 | Asp | Asn | Gly | Asp | Phe |
| Val<br>625 | Ile | Gln | Asn | Gly | Thr<br>630 | Gly | Thr | Ile | Leu | Ser<br>635 | Ser | Leu | Ser | Phe | Asp<br>640 |
| Arg | Glu | Gln | Gln | Ser<br>645 | Thr | Tyr | Thr | Phe | Gln<br>650 | Leu | Lys | Ala | Val | Asp<br>655 | Gly |
| Gly | Val | Pro | Pro<br>660 | Arg | Ser | Ala | Tyr | Val<br>665 | Gly | Val | Thr | Ile | Asn<br>670 | Val | Leu |
| Asp | Glu<br>675 | Asn | Asp | Asn | Ala | Pro<br>680 | Tyr | Ile | Thr | Ala | Pro<br>685 | Ser | Asn | Thr | Ser |
| His | Lys<br>690 | Leu | Leu | Thr | Pro | Gln<br>695 | Thr | Arg | Leu | Gly | Glu<br>700 | Thr | Val | Ser | Gln |
| Val<br>705 | Ala | Ala | Glu | Asp | Phe<br>710 | Asp | Ser | Gly | Val | Asn<br>715 | Ala | Glu | Leu | Ile | Tyr<br>720 |
| Ser | Ile | Ala | Gly | Gly<br>725 | Asn | Pro | Tyr | Gly | Leu<br>730 | Phe | Gln | Ile | Gly | Ser<br>735 | His |
| Ser | Gly | Ala | Ile<br>740 | Thr | Leu | Glu | Lys | Glu<br>745 | Ile | Glu | Arg | Arg | His<br>750 | | His | Gly |
| Leu | His | Arg<br>755 | Leu | Val | Val | Lys | Val<br>760 | Ser | Asp | Arg | Gly | Lys<br>765 | Pro | Pro | Arg |
| Tyr | Gly<br>770 | Thr | Ala | Leu | Val | His<br>775 | Leu | Tyr | Val | Asn | Glu<br>780 | Thr | Leu | Ala | Asn |
| Arg<br>785 | Thr | Leu | Leu | Glu | Thr<br>790 | Leu | Leu | Gly | His | Ser<br>795 | Leu | Asp | Thr | Pro | Leu<br>800 |
| Asp | Ile | Asp | Ile | Ala<br>805 | Gly | Asp | Pro | Glu | Tyr<br>810 | Glu | Arg | Ser | Lys | Gln<br>815 | Arg |
| Gly | Asn | Ile | Leu<br>820 | Phe | Gly | Val | Val | Ala<br>825 | Gly | Val | Val | Ala | Val<br>830 | Ala | Leu |
| Leu | Ile | Ala<br>835 | Leu | Ala | Val | Leu | Val<br>840 | Arg | Tyr | Cys | Arg | Gln<br>845 | Arg | Glu | Ala |
| Lys | Ser<br>850 | Gly | Tyr | Gln | Ala | Gly<br>855 | Lys | Lys | Glu | Thr | Lys<br>860 | Asp | Leu | Tyr | Ala |
| Pro<br>865 | Lys | Pro | Ser | Gly | Lys<br>870 | Ala | Ser | Lys | Gly | Asn<br>875 | Lys | Ser | Lys | Gly | Lys<br>880 |
| Lys | Ser | Lys | Ser | Pro<br>885 | Lys | Pro | Val | Lys | Pro<br>890 | Val | Glu | Asp | Glu<br>895 | | Asp | Glu |
| Ala | Gly | Leu | Gln<br>900 | Lys | Ser | Leu | Lys | Phe<br>905 | Asn | Leu | Met | Ser<br>910 | Asp | Ala | Pro |
| Gly | Asp | Ser<br>915 | Pro | Arg | Ile | His | Leu<br>920 | Pro | Leu | Asn | Tyr | Pro<br>925 | Pro | Gly | Ser |
| Pro | Asp<br>930 | Leu | Gly | Arg | His | Tyr<br>935 | Arg | Ser | Asn | Ser | Pro<br>940 | Leu | Pro | Ser | Ile |

```
Gln  Leu  Gln  Pro  Gln  Ser  Pro  Ser  Ala  Ser  Lys  His  Gln  Val  Val
945                 950                      955                      960

Gln  Asp  Leu  Pro  Pro  Ala  Asn  Thr  Phe  Val  Gly  Thr  Gly  Asp  Thr  Thr
                    965                      970                      975

Ser  Thr  Gly  Ser  Glu  Gln  Tyr  Ser  Asp  Tyr  Ser  Tyr  Arg  Thr  Asn  Pro
               980                      985                      990

Pro  Lys  Tyr  Pro  Ser  Lys  Gln  Val  Gly  Gln  Pro  Phe  Gln  Leu  Ser  Thr
          995                      1000                     1005

Pro  Gln  Pro  Leu  Pro  His  Pro  Tyr  His  Gly  Ala  Ile  Trp  Thr  Glu  Val
     1010                     1015                     1020

Trp  Glu
1025
```

(2) INFORMATION FOR SEQ ID NO:96:

(i) SEQUENCE CHARACTERISTICS:
        (A) LENGTH: 4705 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 115..2827

(xi) SEQUENCE DESCRIPTION: SEQ ID NO:96:

```
CGAAAGCCAT   GTCGGACTCG   TCGCCCAGCG   CCCAAGCGCT   AACCCGCTGA   AAGTTTCTCA        60

GCGAAATCTC   AGGGACGATC   TGGACCCCGC   TGAGAGGAAC   TGCTTTTGAG   TGAG ATG         117
                                                                    Met
                                                                     1

GTC  CCA  GAG  GCC  TGG  AGG  AGC  GGA  CTG  GTA  AGC  ACC  GGG  AGG  GTA  GTG   165
Val  Pro  Glu  Ala  Trp  Arg  Ser  Gly  Leu  Val  Ser  Thr  Gly  Arg  Val  Val
               5                        10                       15

GGA  GTT  TTG  CTT  CTG  CTT  GGT  GCC  TTG  AAC  AAG  GCT  TCC  ACG  GTC  ATT   213
Gly  Val  Leu  Leu  Leu  Leu  Gly  Ala  Leu  Asn  Lys  Ala  Ser  Thr  Val  Ile
          20                       25                       30

CAC  TAT  GAG  ATC  CCG  GAG  GAA  AGA  GAG  AAG  GGT  TTC  GCT  GTG  GGC  AAC   261
His  Tyr  Glu  Ile  Pro  Glu  Glu  Arg  Glu  Lys  Gly  Phe  Ala  Val  Gly  Asn
     35                       40                       45

GTG  GTC  GCG  AAC  CTT  GGT  TTG  GAT  CTC  GGT  AGC  CTC  TCA  GCC  CGC  AGG   309
Val  Val  Ala  Asn  Leu  Gly  Leu  Asp  Leu  Gly  Ser  Leu  Ser  Ala  Arg  Arg
50                       55                       60                       65

TTC  CCG  GTG  GTG  TCT  GGA  GCT  AGC  CGA  AGA  TTC  TTT  GAG  GTG  AAC  CGG   357
Phe  Pro  Val  Val  Ser  Gly  Ala  Ser  Arg  Arg  Phe  Phe  Glu  Val  Asn  Arg
               70                       75                       80

GAG  ACC  GGA  GAG  ATG  TTT  GTG  AAC  GAC  CGT  CTG  GAT  CGA  GAG  GAG  CTG   405
Glu  Thr  Gly  Glu  Met  Phe  Val  Asn  Asp  Arg  Leu  Asp  Arg  Glu  Glu  Leu
          85                       90                       95

TGT  GGG  ACA  CTG  CCC  TCT  TGC  ACT  GTA  ACT  CTG  GAG  TTG  GTA  GTG  GAG   453
Cys  Gly  Thr  Leu  Pro  Ser  Cys  Thr  Val  Thr  Leu  Glu  Leu  Val  Val  Glu
     100                      105                      110

AAC  CCG  CTG  GAG  CTG  TTC  AGC  GTG  GAA  GTG  GTG  ATC  CAG  GAC  ATC  AAC   501
Asn  Pro  Leu  Glu  Leu  Phe  Ser  Val  Glu  Val  Val  Ile  Gln  Asp  Ile  Asn
115                      120                      125

GAC  AAC  AAT  CCT  GCT  TTC  CCT  ACC  CAG  GAA  ATG  AAA  TTG  GAG  ATT  AGC   549
Asp  Asn  Asn  Pro  Ala  Phe  Pro  Thr  Gln  Glu  Met  Lys  Leu  Glu  Ile  Ser
130                      135                      140                      145

GAG  GCC  GTG  GCT  CCG  GGG  ACG  CGC  TTT  CCG  CTC  GAG  AGC  GCG  CAC  GAT   597
Glu  Ala  Val  Ala  Pro  Gly  Thr  Arg  Phe  Pro  Leu  Glu  Ser  Ala  His  Asp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 150 |     |     |     |     | 155 |     |     |     |     | 160 |     |      |
| CCC | GAT | CTG | GGA | AGC | AAC | TCT | TTA | CAA | ACC | TAT | GAG | CTG | AGC | CGA | AAT | 645  |
| Pro | Asp | Leu | Gly | Ser | Asn | Ser | Leu | Gln | Thr | Tyr | Glu | Leu | Ser | Arg | Asn |      |
|     |     |     | 165 |     |     |     |     | 170 |     |     |     |     | 175 |     |     |      |
| GAA | TAC | TTT | GCG | CTT | CGC | GTG | CAG | ACG | CGG | GAG | GAC | AGC | ACC | AAG | TAC | 693  |
| Glu | Tyr | Phe | Ala | Leu | Arg | Val | Gln | Thr | Arg | Glu | Asp | Ser | Thr | Lys | Tyr |      |
|     |     | 180 |     |     |     |     | 185 |     |     |     |     | 190 |     |     |     |      |
| GCG | GAG | CTG | GTG | TTG | GAG | CGC | GCC | CTG | GAC | CGA | GAA | CGG | GAG | CCT | AGT | 741  |
| Ala | Glu | Leu | Val | Leu | Glu | Arg | Ala | Leu | Asp | Arg | Glu | Arg | Glu | Pro | Ser |      |
|     | 195 |     |     |     |     | 200 |     |     |     |     | 205 |     |     |     |     |      |
| CTC | CAG | TTA | GTG | CTG | ACG | GCG | TTG | GAC | GGA | GGG | ACC | CCA | GCT | CTC | TCC | 789  |
| Leu | Gln | Leu | Val | Leu | Thr | Ala | Leu | Asp | Gly | Gly | Thr | Pro | Ala | Leu | Ser |      |
| 210 |     |     |     |     | 215 |     |     |     |     | 220 |     |     |     |     | 225 |      |
| GCC | AGC | CTG | CCT | ATT | CAC | ATC | AAG | GTG | CTG | GAC | GCG | AAT | GAC | AAT | GCG | 837  |
| Ala | Ser | Leu | Pro | Ile | His | Ile | Lys | Val | Leu | Asp | Ala | Asn | Asp | Asn | Ala |      |
|     |     |     |     | 230 |     |     |     |     | 235 |     |     |     |     | 240 |     |      |
| CCT | GTC | TTC | AAC | CAG | TCC | TTG | TAC | CGG | GCG | CGC | GTT | CCT | GGA | GGA | TGC | 885  |
| Pro | Val | Phe | Asn | Gln | Ser | Leu | Tyr | Arg | Ala | Arg | Val | Pro | Gly | Gly | Cys |      |
|     |     |     | 245 |     |     |     |     | 250 |     |     |     |     | 255 |     |     |      |
| ACC | TCC | GGC | ACG | CGC | GTG | GTA | CAA | GTC | CTT | GCA | ACG | GAT | CTG | GAT | GAA | 933  |
| Thr | Ser | Gly | Thr | Arg | Val | Val | Gln | Val | Leu | Ala | Thr | Asp | Leu | Asp | Glu |      |
|     |     | 260 |     |     |     |     | 265 |     |     |     |     | 270 |     |     |     |      |
| GGC | CCC | AAC | GGT | GAA | ATT | ATT | TAC | TCC | TTC | GGC | AGC | CAC | AAC | CGC | GCC | 981  |
| Gly | Pro | Asn | Gly | Glu | Ile | Ile | Tyr | Ser | Phe | Gly | Ser | His | Asn | Arg | Ala |      |
|     | 275 |     |     |     |     | 280 |     |     |     |     | 285 |     |     |     |     |      |
| GGC | GTG | CGG | CAA | CTA | TTC | GCC | TTA | GAC | CTT | GTA | ACC | GGG | ATG | CTG | ACA | 1029 |
| Gly | Val | Arg | Gln | Leu | Phe | Ala | Leu | Asp | Leu | Val | Thr | Gly | Met | Leu | Thr |      |
| 290 |     |     |     |     | 295 |     |     |     |     | 300 |     |     |     |     | 305 |      |
| ATC | AAG | GGT | CGG | CTG | GAC | TTC | GAG | GAC | ACC | AAA | CTC | CAT | GAG | ATT | TAC | 1077 |
| Ile | Lys | Gly | Arg | Leu | Asp | Phe | Glu | Asp | Thr | Lys | Leu | His | Glu | Ile | Tyr |      |
|     |     |     |     | 310 |     |     |     |     | 315 |     |     |     |     | 320 |     |      |
| ATC | CAG | GCC | AAA | GAC | AAG | GGC | GCC | AAT | CCC | GAA | GGA | GCA | CAT | TGC | AAA | 1125 |
| Ile | Gln | Ala | Lys | Asp | Lys | Gly | Ala | Asn | Pro | Glu | Gly | Ala | His | Cys | Lys |      |
|     |     |     | 325 |     |     |     |     | 330 |     |     |     |     | 335 |     |     |      |
| GTG | TTG | GTG | GAG | GTT | GTG | GAT | GTG | AAT | GAC | AAC | GCC | CCG | GAG | ATC | ACA | 1173 |
| Val | Leu | Val | Glu | Val | Val | Asp | Val | Asn | Asp | Asn | Ala | Pro | Glu | Ile | Thr |      |
|     |     | 340 |     |     |     |     | 345 |     |     |     |     | 350 |     |     |     |      |
| GTC | ACC | TCC | GTG | TAC | AGC | CCA | GTA | CCC | GAG | GAT | GCC | TCT | GGG | ACT | GTC | 1221 |
| Val | Thr | Ser | Val | Tyr | Ser | Pro | Val | Pro | Glu | Asp | Ala | Ser | Gly | Thr | Val |      |
|     | 355 |     |     |     |     | 360 |     |     |     |     | 365 |     |     |     |     |      |
| ATC | GCT | TTG | CTC | AGT | GTG | ACT | GAC | CTG | GAT | GCT | GGC | GAG | AAC | GGG | CTG | 1269 |
| Ile | Ala | Leu | Leu | Ser | Val | Thr | Asp | Leu | Asp | Ala | Gly | Glu | Asn | Gly | Leu |      |
| 370 |     |     |     |     | 375 |     |     |     |     | 380 |     |     |     |     | 385 |      |
| GTG | ACC | TGC | GAA | GTT | CCA | CCG | GGT | CTC | CCT | TTC | AGC | CTT | ACT | TCT | TCC | 1317 |
| Val | Thr | Cys | Glu | Val | Pro | Pro | Gly | Leu | Pro | Phe | Ser | Leu | Thr | Ser | Ser |      |
|     |     |     |     | 390 |     |     |     |     | 395 |     |     |     |     | 400 |     |      |
| CTC | AAG | AAT | TAC | TTC | ACT | TTG | AAA | ACC | AGT | GCA | GAC | CTG | GAT | CGG | GAG | 1365 |
| Leu | Lys | Asn | Tyr | Phe | Thr | Leu | Lys | Thr | Ser | Ala | Asp | Leu | Asp | Arg | Glu |      |
|     |     |     | 405 |     |     |     |     | 410 |     |     |     |     | 415 |     |     |      |
| ACT | GTG | CCA | GAA | TAC | AAC | CTC | AGC | ATC | ACC | GCC | CGA | GAC | GCC | GGA | ACC | 1413 |
| Thr | Val | Pro | Glu | Tyr | Asn | Leu | Ser | Ile | Thr | Ala | Arg | Asp | Ala | Gly | Thr |      |
|     |     | 420 |     |     |     |     | 425 |     |     |     |     | 430 |     |     |     |      |
| CCT | TCC | CTC | TCA | GCC | CTT | ACA | ATA | GTG | CGT | GTT | CAA | GTG | TCC | GAC | ATC | 1461 |
| Pro | Ser | Leu | Ser | Ala | Leu | Thr | Ile | Val | Arg | Val | Gln | Val | Ser | Asp | Ile |      |
|     | 435 |     |     |     |     | 440 |     |     |     |     | 445 |     |     |     |     |      |
| AAT | GAC | AAC | CCT | CCA | CAA | TCT | TCT | CAA | TCT | TCC | TAC | GAC | GTT | TAC | ATT | 1509 |
| Asn | Asp | Asn | Pro | Pro | Gln | Ser | Ser | Gln | Ser | Ser | Tyr | Asp | Val | Tyr | Ile |      |
| 450 |     |     |     |     | 455 |     |     |     |     | 460 |     |     |     |     | 465 |      |
| GAA | GAA | AAC | AAC | CTC | CCC | GGG | GCT | CCA | ATA | CTA | AAC | CTA | AGT | GTC | TGG | 1557 |
| Glu | Glu | Asn | Asn | Leu | Pro | Gly | Ala | Pro | Ile | Leu | Asn | Leu | Ser | Val | Trp |      |

-continued

|     |     |     | 470 |     |     |     |     | 475 |     |     |     |     | 480 |     |      |
|-----|-----|-----|-----|-----|-----|-----|-----|-----|-----|-----|-----|-----|-----|-----|------|
| GAC | CCC | GAC | GCC | CCG | CAG | AAT | GCT | CGG | CTT | TCT | TTC | TTT | CTC | TTG | GAG  | 1605 |
| Asp | Pro | Asp | Ala | Pro | Gln | Asn | Ala | Arg | Leu | Ser | Phe | Phe | Leu | Leu | Glu  |
|     |     |     | 485 |     |     |     |     | 490 |     |     |     |     | 495 |     |      |
| CAA | GGA | GCT | GAA | ACC | GGG | CTA | GTG | GGT | CGC | TAT | TTC | ACA | ATA | AAT | CGT  | 1653 |
| Gln | Gly | Ala | Glu | Thr | Gly | Leu | Val | Gly | Arg | Tyr | Phe | Thr | Ile | Asn | Arg  |
|     |     |     | 500 |     |     |     |     | 505 |     |     |     |     | 510 |     |      |
| GAC | AAT | GGC | ATA | GTG | TCA | TCC | TTA | GTG | CCC | CTA | GAC | TAT | GAG | GAT | CGG  | 1701 |
| Asp | Asn | Gly | Ile | Val | Ser | Ser | Leu | Val | Pro | Leu | Asp | Tyr | Glu | Asp | Arg  |
|     |     |     | 515 |     |     |     |     | 520 |     |     |     |     | 525 |     |      |
| CGG | GAA | TTT | GAA | TTA | ACA | GCT | CAT | ATC | AGC | GAT | GGG | GGC | ACC | CCG | GTC  | 1749 |
| Arg | Glu | Phe | Glu | Leu | Thr | Ala | His | Ile | Ser | Asp | Gly | Gly | Thr | Pro | Val  |
|     |     |     | 530 |     |     |     |     | 535 |     |     |     |     | 540 |     | 545  |
| CTA | GCC | ACC | AAC | ATC | AGC | GTG | AAC | ATA | TTT | GTC | ACT | GAT | CGC | AAT | GAC  | 1797 |
| Leu | Ala | Thr | Asn | Ile | Ser | Val | Asn | Ile | Phe | Val | Thr | Asp | Arg | Asn | Asp  |
|     |     |     |     | 550 |     |     |     |     | 555 |     |     |     |     | 560 |      |
| AAT | GCC | CCC | CAG | GTC | CTA | TAT | CCT | CGG | CCA | GGT | GGG | AGC | TCG | GTG | GAG  | 1845 |
| Asn | Ala | Pro | Gln | Val | Leu | Tyr | Pro | Arg | Pro | Gly | Gly | Ser | Ser | Val | Glu  |
|     |     |     | 565 |     |     |     |     | 570 |     |     |     |     | 575 |     |      |
| ATG | CTG | CCT | CGA | GGT | ACC | TCA | GCT | GGC | CAC | CTA | GTG | TCA | CGG | GTG | GTA  | 1893 |
| Met | Leu | Pro | Arg | Gly | Thr | Ser | Ala | Gly | His | Leu | Val | Ser | Arg | Val | Val  |
|     |     |     | 580 |     |     |     |     | 585 |     |     |     |     | 590 |     |      |
| GGC | TGG | GAC | GCG | GAT | GCA | GGG | CAC | AAT | GCC | TGG | CTC | TCC | TAC | AGT | CTC  | 1941 |
| Gly | Trp | Asp | Ala | Asp | Ala | Gly | His | Asn | Ala | Trp | Leu | Ser | Tyr | Ser | Leu  |
|     |     |     | 595 |     |     |     |     | 600 |     |     |     |     | 605 |     |      |
| TTT | GGA | TCC | CCT | AAC | CAG | AGC | CTT | TTT | GCC | ATA | GGG | CTG | CAC | ACT | GGT  | 1989 |
| Phe | Gly | Ser | Pro | Asn | Gln | Ser | Leu | Phe | Ala | Ile | Gly | Leu | His | Thr | Gly  |
|     |     |     | 610 |     |     |     |     | 615 |     |     |     |     | 620 |     | 625  |
| CAA | ATC | AGT | ACT | GCC | CGT | CCA | GTC | CAA | GAC | ACA | GAT | TCA | CCC | AGG | CAG  | 2037 |
| Gln | Ile | Ser | Thr | Ala | Arg | Pro | Val | Gln | Asp | Thr | Asp | Ser | Pro | Arg | Gln  |
|     |     |     |     | 630 |     |     |     |     | 635 |     |     |     |     | 640 |      |
| ACT | CTC | ACT | GTC | TTG | ATC | AAA | GAC | AAT | GGG | GAG | CCT | TCG | CTC | TCC | ACC  | 2085 |
| Thr | Leu | Thr | Val | Leu | Ile | Lys | Asp | Asn | Gly | Glu | Pro | Ser | Leu | Ser | Thr  |
|     |     |     |     | 645 |     |     |     |     | 650 |     |     |     |     | 655 |      |
| ACT | GCT | ACC | CTC | ACT | GTG | TCA | GTA | ACC | GAG | GAC | TCT | CCT | GAA | GCC | CGA  | 2133 |
| Thr | Ala | Thr | Leu | Thr | Val | Ser | Val | Thr | Glu | Asp | Ser | Pro | Glu | Ala | Arg  |
|     |     |     | 660 |     |     |     |     | 665 |     |     |     |     | 670 |     |      |
| GCC | GAG | TTC | CCC | TCT | GGC | TCT | GCC | CCC | CGG | GAG | CAG | AAA | AAA | AAT | CTC  | 2181 |
| Ala | Glu | Phe | Pro | Ser | Gly | Ser | Ala | Pro | Arg | Glu | Gln | Lys | Lys | Asn | Leu  |
|     |     |     | 675 |     |     |     |     | 680 |     |     |     |     | 685 |     |      |
| ACC | TTT | TAT | CTA | CTT | CTT | TCT | CTA | ATC | CTG | GTT | TCT | GTG | GGC | TTC | GTG  | 2229 |
| Thr | Phe | Tyr | Leu | Leu | Leu | Ser | Leu | Ile | Leu | Val | Ser | Val | Gly | Phe | Val  |
|     |     |     | 690 |     |     |     |     | 695 |     |     |     |     | 700 |     | 705  |
| GTC | ACA | GTG | TTC | GGA | GTA | ATC | ATA | TTC | AAA | GTT | TAC | AAG | TGG | AAG | CAG  | 2277 |
| Val | Thr | Val | Phe | Gly | Val | Ile | Ile | Phe | Lys | Val | Tyr | Lys | Trp | Lys | Gln  |
|     |     |     |     | 710 |     |     |     |     | 715 |     |     |     |     | 720 |      |
| TCT | AGA | GAC | CTA | TAC | CGA | GCC | CCG | GTG | AGC | TCA | CTG | TAC | CGA | ACA | CCA  | 2325 |
| Ser | Arg | Asp | Leu | Tyr | Arg | Ala | Pro | Val | Ser | Ser | Leu | Tyr | Arg | Thr | Pro  |
|     |     |     | 725 |     |     |     |     | 730 |     |     |     |     | 735 |     |      |
| GGG | CCC | TCC | TTG | CAC | GCG | GAC | GCC | GTG | CGG | GGA | GGC | CTG | ATG | TCG | CCG  | 2373 |
| Gly | Pro | Ser | Leu | His | Ala | Asp | Ala | Val | Arg | Gly | Gly | Leu | Met | Ser | Pro  |
|     |     |     | 740 |     |     |     |     | 745 |     |     |     |     | 750 |     |      |
| CAC | CTT | TAC | CAT | CAG | GTG | TAT | CTC | ACC | ACG | GAC | TCC | CGC | CGC | AGC | GAC  | 2421 |
| His | Leu | Tyr | His | Gln | Val | Tyr | Leu | Thr | Thr | Asp | Ser | Arg | Arg | Ser | Asp  |
|     |     |     | 755 |     |     |     |     | 760 |     |     |     |     | 765 |     |      |
| CCG | CTG | CTG | AAG | AAA | CCT | GGT | GCA | GCC | AGT | CCA | CTG | GCC | AGC | CGC | CAG  | 2469 |
| Pro | Leu | Leu | Lys | Lys | Pro | Gly | Ala | Ala | Ser | Pro | Leu | Ala | Ser | Arg | Gln  |
|     |     |     | 770 |     |     |     |     | 775 |     |     |     |     | 780 |     | 785  |
| AAC | ACG | CTG | CGG | AGC | TGT | GAT | CCG | GTG | TTC | TAT | AGG | CAG | GTG | TTG | GGT  | 2517 |
| Asn | Thr | Leu | Arg | Ser | Cys | Asp | Pro | Val | Phe | Tyr | Arg | Gln | Val | Leu | Gly  |

```
              790                        795                        800
GCA AGA AGC GCC CCT CCC GGA CAG CAA GCC CCG CCC AAC ACG GAC TGG                2565
Ala Glu Ser Ala Pro Pro Gly Gln Gln Ala Pro Pro Asn Thr Asp Trp
                805                 810                 815

CGT TTC TCT CAG GCC CAG AGA CCC GGC ACC AGC GGC TCC CAA AAT GGC                2613
Arg Phe Ser Gln Ala Gln Arg Pro Gly Thr Ser Gly Ser Gln Asn Gly
            820                 825                 830

GAT GAC ACC GGC ACC TGG CCC AAC AAC CAG TTT GAC ACA GAG ATG CTG                2661
Asp Asp Thr Gly Thr Trp Pro Asn Asn Gln Phe Asp Thr Glu Met Leu
        835                 840                 845

CAA GCC ATG ATC TTG GCG TCC GCC AGT GAA GCT GCT GAT GGG AGC TCC                2709
Gln Ala Met Ile Leu Ala Ser Ala Ser Glu Ala Ala Asp Gly Ser Ser
850                 855                 860                 865

ACC CTG GGA GGG GGT GCC GGC ACC ATG GGA TTG AGC GCC CGC TAC GGA                2757
Thr Leu Gly Gly Gly Ala Gly Thr Met Gly Leu Ser Ala Arg Tyr Gly
                870                 875                 880

CCC CAG TTC ACC CTG CAG CAC GTG CCC GAC TAC CGC CAG AAT GTC TAC                2805
Pro Gln Phe Thr Leu Gln His Val Pro Asp Tyr Arg Gln Asn Val Tyr
            885                 890                 895

ATC CCA GGC AGC AAT GCA CAC T GACCAACGCA GCTGGCAAGC GGATGGCAAG                 2857
Ile Pro Gly Ser Asn Ala His
        900

GCCCAGCAGG TGGCAATGGC AACAAGAAGA AGTCGGCAAG AAGGAGAAGA AGTAACATGG             2917
AGGCCAGGCC AAGAGCCACA GGGCAGCCTC TCCCCGAACC AGCCCAGCTT CTCCTTACCT             2977
GCACCCAGGC CTCAGAGTTT CAGGGCTAAC CCCAGAATA CTGGTAGGGG CCAAGGCATC              3037
TCCCTTGGAA ACAGAAACAA GTGCCATCAC ACCATCCCTT CCCCAGGTGT AATATCCAAA             3097
GCAGTTCCGC TGGGAACCCC ATCCAATCAG TGGCTGTACC CATTTGGGTA GTGGGGTTCA             3157
TGTAGACACC AAGAACCATT TGCCACACCC CGTTTAGTTA CAGCTGAACC CTCCATCTTC             3217
CAAATCAATC AGGCCCATCC ATCCCATGCC TCCCTCCTCC CCACCCCACT CCAACAGTTC             3277
CTCTTTCCCG AGTAAGGTGG TTGGGGTGTT GAAGTACCAA GTAACCTACA AGCCTCCTAG             3337
TTCTGAAAAG TTGGAAGGGC ATCATGACCT CTTGGCCTCT CCTTTGATTC TCAATCTTCC             3397
CCCAAAGCAT GGTTTGGTGC CAGCCCCTTC ACCTCCTTCC AGAGCCCAAG ATCAATGCTC             3457
AAGTTTTGGA GGACATGATC ACCATCCCCA TGGTACTGAT GCTTGCTGGA TTTAGGGAGG             3517
GCATTTGCT ACCAAGCCTC TTCCCAACGC CCTGGGACCA GTCTTCTGTT TTGTTTTTCA              3577
TTGTTTGAGC TTTCCACTGC ATGCCTTGAC TTCCCCCACC TCCTCCTCAA ACAAGAGACT             3637
CCACTGCATG TTCCAAGACA GTATGGGGTG GTAAGATAAG GAAGGGAAGT GTGTGGATGT             3697
GGATGGTGGG GGCATGGACA AAGCTTGACA CATCAAGTTA TCAAGGCCTT GGAGGAGGCT             3757
CTGTATGTCC TCAGGGGACT GACAACATCC TCCAGATTCC AGCCATAAAC CAATAACTAG             3817
GCTGGACCCT TCCCACTACA TAATAGGGCT CAGCCAGGCA GCCAGCTTTG GCTGAGCTA              3877
ACAGGACCAA TGGATTAACT GGCATTTCAG TCCAAGGAAG CTCGAAGCAG GTTTAGGACC             3937
AGGTCCCCTT GAGAGGTCAG AGGGGCCTCT GTGGGTGCTG GGTACTCCAG AGGTGCCACT             3997
GGTGGAAGGG TCAGCGGAGC CCCAGCAGGA AGGGTGGGCC AGCCAGGCCA TTCTTAGTCC             4057
CTGGGTTGGG GAGGCAGGGA GCTAGGGCAG GGACCAAATG AACAGAAAGT CTCAGCCCAG             4117
GATGGGGCTT CTTCAACAGG CCCCTGCCCT CCTGAAGCCT CAGTCCTTCA CCTTGCCAGG             4177
TGCCGTTTCT CTTCCGTGAA GGCCACTGCC CAGGTCCCCA GTGCGCCCCC TAGTGGCCAT             4237
AGCCTGGTTA AAGTTCCCCA GTGCCTCCTT GTGATAGACC TTCTTCTCCC ACCCCCTTCT             4297
GCCCCTGGGT CCCCGGCCAT CCAGCGGGGC TGCCAGAGAA CCCCAGACCT GCCCTTACAG             4357
```

-continued

| | | | | | |
|---|---|---|---|---|---|
| TAGTGTAGCG | CCCCCTCCCT | CTTTCGGCTG | GTGTAGAATA | GCCAGTAGTG | TAGTGCGGTG | 4417 |
| TGCTTTTACG | TGATGGCGGG | TGGGCAGCGG | GCGGCGGCGT | CCGCGCAGCC | GTCTGTCCTT | 4477 |
| GATCTGCCCG | CGGCGGCCCG | TGTTGTGTTT | TGTGCTGTGT | CCAGCGCTAA | GGCGACCCCC | 4537 |
| TCCCCCGTAC | TGACTTCTCC | TATAAGCGCT | TCTCTTCGCA | TAGTCACGTA | GCTCCCACCC | 4597 |
| CACCCTCTTC | CTGTGTCTCA | CGCAAGTTTT | ATACTCTAAT | ATTTATATGG | CTTTTTTCT | 4657 |
| TCGACAAAAA | AATAATAAAA | CGTTTCTTCT | GAAAAAAAAA | AAAAAAA | | 4705 |

( 2 ) INFORMATION FOR SEQ ID NO:97:

( i ) SEQUENCE CHARACTERISTICS:
        ( A ) LENGTH: 904 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

```
Met Val Pro Glu Ala Trp Arg Ser Gly Leu Val Ser Thr Gly Arg Val
 1               5                  10                  15

Val Gly Val Leu Leu Leu Gly Ala Leu Asn Lys Ala Ser Thr Val
                20                  25                  30

Ile His Tyr Glu Ile Pro Glu Glu Arg Glu Lys Gly Phe Ala Val Gly
            35                  40                  45

Asn Val Ala Asn Leu Gly Leu Asp Leu Gly Ser Leu Ser Ala Arg
        50                  55                  60

Arg Phe Pro Val Val Ser Gly Ala Ser Arg Arg Phe Phe Glu Val Asn
 65                  70                  75                  80

Arg Glu Thr Gly Glu Met Phe Val Asn Asp Arg Leu Asp Arg Glu Glu
                85                  90                  95

Leu Cys Gly Thr Leu Pro Ser Cys Thr Val Thr Leu Glu Leu Val Val
               100                 105                 110

Glu Asn Pro Leu Glu Leu Phe Ser Val Glu Val Val Ile Gln Asp Ile
           115                 120                 125

Asn Asp Asn Asn Pro Ala Phe Pro Thr Gln Glu Met Lys Leu Glu Ile
       130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
            180                 185                 190

Tyr Ala Glu Leu Val Leu Glu Arg Ala Leu Asp Arg Glu Arg Glu Pro
        195                 200                 205

Ser Leu Gln Leu Val Leu Thr Ala Leu Asp Gly Gly Thr Pro Ala Leu
    210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
            260                 265                 270

Glu Gly Pro Asn Gly Glu Ile Ile Tyr Ser Phe Gly Ser His Asn Arg
        275                 280                 285

Ala Gly Val Arg Gln Leu Phe Ala Leu Asp Leu Val Thr Gly Met Leu
    290                 295                 300
```

```
Thr  Ile  Lys  Gly  Arg  Leu  Asp  Phe  Glu  Asp  Thr  Lys  Leu  His  Glu  Ile
305            310                 315                 320

Tyr  Ile  Gln  Ala  Lys  Asp  Lys  Gly  Ala  Asn  Pro  Glu  Gly  Ala  His  Cys
                325                 330                 335

Lys  Val  Leu  Val  Glu  Val  Val  Asp  Val  Asn  Asp  Asn  Ala  Pro  Glu  Ile
                340                 345                 350

Thr  Val  Thr  Ser  Val  Tyr  Ser  Pro  Val  Pro  Glu  Asp  Ala  Ser  Gly  Thr
                355                 360                 365

Val  Ile  Ala  Leu  Leu  Ser  Val  Thr  Asp  Leu  Asp  Ala  Gly  Glu  Asn  Gly
          370                 375                 380

Leu  Val  Thr  Cys  Glu  Val  Pro  Pro  Gly  Leu  Pro  Phe  Ser  Leu  Thr  Ser
385                 390                 395                      400

Ser  Leu  Lys  Asn  Tyr  Phe  Thr  Leu  Lys  Thr  Ser  Ala  Asp  Leu  Asp  Arg
                405                 410                 415

Glu  Thr  Val  Pro  Glu  Tyr  Asn  Leu  Ser  Ile  Thr  Ala  Arg  Asp  Ala  Gly
                420                 425                 430

Thr  Pro  Ser  Leu  Ser  Ala  Leu  Thr  Ile  Val  Arg  Val  Gln  Val  Ser  Asp
          435                 440                 445

Ile  Asn  Asp  Asn  Pro  Pro  Gln  Ser  Ser  Gln  Ser  Ser  Tyr  Asp  Val  Tyr
450                 455                 460

Ile  Glu  Glu  Asn  Asn  Leu  Pro  Gly  Ala  Pro  Ile  Leu  Asn  Leu  Ser  Val
465                 470                 475                      480

Trp  Asp  Pro  Asp  Ala  Pro  Gln  Asn  Ala  Arg  Leu  Ser  Phe  Phe  Leu  Leu
                485                 490                 495

Glu  Gln  Gly  Ala  Glu  Thr  Gly  Leu  Val  Gly  Arg  Tyr  Phe  Thr  Ile  Asn
                500                 505                 510

Arg  Asp  Asn  Gly  Ile  Val  Ser  Ser  Leu  Val  Pro  Leu  Asp  Tyr  Glu  Asp
                515                 520                 525

Arg  Arg  Glu  Phe  Glu  Leu  Thr  Ala  His  Ile  Ser  Asp  Gly  Gly  Thr  Pro
          530                 535                 540

Val  Leu  Ala  Thr  Asn  Ile  Ser  Val  Asn  Ile  Phe  Val  Thr  Asp  Arg  Asn
545                 550                 555                      560

Asp  Asn  Ala  Pro  Gln  Val  Leu  Tyr  Pro  Arg  Pro  Gly  Gly  Ser  Ser  Val
                565                 570                 575

Glu  Met  Leu  Pro  Arg  Gly  Thr  Ser  Ala  Gly  His  Leu  Val  Ser  Arg  Val
                580                 585                 590

Val  Gly  Trp  Asp  Ala  Asp  Ala  Gly  His  Asn  Ala  Trp  Leu  Ser  Tyr  Ser
          595                 600                 605

Leu  Phe  Gly  Ser  Pro  Asn  Gln  Ser  Leu  Phe  Ala  Ile  Gly  Leu  His  Thr
     610                 615                 620

Gly  Gln  Ile  Ser  Thr  Ala  Arg  Pro  Val  Gln  Asp  Thr  Asp  Ser  Pro  Arg
625                 630                 635                      640

Gln  Thr  Leu  Thr  Val  Leu  Ile  Lys  Asp  Asn  Gly  Glu  Pro  Ser  Leu  Ser
                645                 650                 655

Thr  Thr  Ala  Thr  Leu  Thr  Val  Ser  Val  Thr  Glu  Asp  Ser  Pro  Glu  Ala
                660                 665                 670

Arg  Ala  Glu  Phe  Pro  Ser  Gly  Ser  Ala  Pro  Arg  Glu  Gln  Lys  Lys  Asn
                675                 680                 685

Leu  Thr  Phe  Tyr  Leu  Leu  Leu  Ser  Leu  Ile  Leu  Val  Ser  Val  Gly  Phe
     690                 695                 700

Val  Val  Thr  Val  Phe  Gly  Val  Ile  Ile  Phe  Lys  Val  Tyr  Lys  Trp  Lys
705                 710                 715                      720

Gln  Ser  Arg  Asp  Leu  Tyr  Arg  Ala  Pro  Val  Ser  Ser  Leu  Tyr  Arg  Thr
```

|     |     |     |     |     |     | 725 |     |     |     | 730 |     |     |     | 735 |     |
|-----|-----|-----|-----|-----|-----|-----|-----|-----|-----|-----|-----|-----|-----|-----|-----|
| Pro | Gly | Pro | Ser | Leu | His | Ala | Asp | Ala | Val | Arg | Gly | Gly | Leu | Met | Ser |

Pro Gly Pro Ser Leu His Ala Asp Ala Val Arg Gly Gly Leu Met Ser
                          725                 730                 735

Pro His Leu Tyr His Gln Val Tyr Leu Thr Thr Asp Ser Arg Arg Ser
        740                 745                 750

Asp Pro Leu Leu Lys Lys Pro Gly Ala Ala Ser Pro Leu Ala Ser Arg
    755                 760                 765

Gln Asn Thr Leu Arg Ser Cys Asp Pro Val Phe Tyr Arg Gln Val Leu
770         775                 780
785             790                 795                 800

Gly Ala Glu Ser Ala Pro Pro Gly Gln Gln Ala Pro Pro Asn Thr Asp
            805                 810                 815

Trp Arg Phe Ser Gln Ala Gln Arg Pro Gly Thr Ser Gly Ser Gln Asn
            820                 825                 830

Gly Asp Asp Thr Gly Thr Trp Pro Asn Asn Gln Phe Asp Thr Glu Met
            835                 840                 845

Leu Gln Ala Met Ile Leu Ala Ser Ala Ser Glu Ala Ala Asp Gly Ser
    850                 855                 860

Ser Thr Leu Gly Gly Gly Ala Gly Thr Met Gly Leu Ser Ala Arg Tyr
865                 870                 875                 880

Gly Pro Gln Phe Thr Leu Gln His Val Pro Asp Tyr Arg Gln Asn Val
            885                 890                 895

Tyr Ile Pro Gly Ser Asn Ala His
            900

(2) INFORMATION FOR SEQ ID NO:98:

(i) SEQUENCE CHARACTERISTICS:
      (A) LENGTH: 556 amino acids
      (B) TYPE: amino acid
      (D) TOPOLOGY: linear (ii) MOLECULE TYPE: protein (xi) SEQUENCE DESCRIPTION: SEQ ID NO:98:

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
            20                  25                  30

Ser Leu Arg Tyr Thr Val Thr Gly Pro Gly Ala Asp Gln Pro Pro Thr
        35                  40                  45

Gly Ile Phe Ile Ile Asn Pro Ile Ser Gly Gln Leu Ser Val Thr Lys
    50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
            85                  90                  95

Asn Val Ile Asp Met Asn Asp Asn Arg Pro Glu Phe Leu His Gln Val
            100                 105                 110

Trp Asn Gly Ser Val Pro Glu Gly Ser Lys Pro Gly Thr Tyr Val Met
        115                 120                 125

Thr Val Thr Ala Ile Asp Ala Asp Asp Pro Asn Ala Leu Asn Gly Met
    130                 135                 140

Leu Arg Tyr Arg Ile Leu Ser Gln Ala Pro Ser Thr Pro Ser Pro Asn
145                 150                 155                 160

Met Phe Thr Ile Asn Asn Glu Thr Gly Asp Ile Ile Thr Val Ala Ala
            165                 170                 175

|     |     |     |     |     |     |     |     |     |     |     |     |     |     |     |
|---|---|---|---|---|---|---|---|---|---|---|---|---|---|---|
| Gly | Leu | Asp | Arg 180 | Glu | Lys | Val | Gln | Gln 185 | Tyr | Thr | Leu | Ile | Ile 190 | Gln | Ala |
| Thr | Asp | Met 195 | Glu | Gly | Asn | Pro | Thr 200 | Tyr | Gly | Leu | Ser | Asn 205 | Thr | Ala | Thr |
| Ala | Val 210 | Ile | Thr | Val | Thr | Asp 215 | Val | Asn | Asp | Asn | Pro 220 | Pro | Glu | Phe | Thr |
| Ala 225 | Met | Thr | Phe | Tyr | Gly 230 | Glu | Val | Pro | Glu | Asn 235 | Arg | Val | Asp | Ile | Ile 240 |
| Val | Ala | Asn | Leu | Thr 245 | Val | Thr | Asp | Lys | Asp 250 | Gln | Pro | His | Thr | Pro 255 | Ala |
| Trp | Asn | Ala | Val 260 | Thr | Arg | Ile | Ser | Gly 265 | Gly | Asp | Pro | Thr | Gly 270 | Arg | Phe |
| Ala | Ile | Gln 275 | Thr | Asp | Pro | Asn | Ser 280 | Asn | Asp | Gly | Leu | Val 285 | Thr | Val | Val |
| Lys | Pro 290 | Ile | Asp | Phe | Glu | Thr 295 | Asn | Arg | Met | Phe | Val 300 | Leu | Thr | Val | Ala |
| Ala 305 | Glu | Asn | Gln | Val | Pro 310 | Leu | Ala | Lys | Gly | Ile 315 | Gln | His | Pro | Pro | Gln 320 |
| Ser | Thr | Ala | Thr | Val 325 | Ser | Val | Thr | Val | Ile 330 | Asp | Val | Asn | Glu | Asn 335 | Pro |
| Tyr | Phe | Ala | Pro 340 | Asn | Pro | Lys | Ile | Ile 345 | Arg | Gln | Glu | Glu | Gly 350 | Leu | His |
| Ala | Gly | Thr 355 | Met | Leu | Thr | Thr | Phe 360 | Thr | Ala | Gly | Asp | Pro 365 | Asp | Arg | Tyr |
| Met | Gln 370 | Gln | Asn | Ile | Arg | Tyr 375 | Thr | Lys | Leu | Ser | Asp 380 | Pro | Ala | Asn | Trp |
| Leu 385 | Lys | Ile | Asp | Pro | Val 390 | Asn | Gly | Gln | Ile | Thr 395 | Thr | Ile | Ala | Val | Leu 400 |
| Asp | Arg | Glu | Ser | Pro 405 | Asn | Val | Lys | Asn | Asn 410 | Ile | Tyr | Asn | Ala | Thr 415 | Phe |
| Leu | Ala | Ser | Asp 420 | Asn | Gly | Ile | Pro | Pro 425 | Met | Ser | Gly | Thr | Gly 430 | Thr | Leu |
| Gln | Ile | Tyr 435 | Leu | Leu | Asp | Ile | Asn 440 | Asp | Asn | Ala | Pro | Gln 445 | Val | Leu | Pro |
| Gln | Glu 450 | Ala | Glu | Thr | Cys | Glu 455 | Thr | Pro | Asp | Pro | Asn 460 | Ser | Ile | Asn | Ile |
| Thr 465 | Thr | Ala | Leu | Asp | Tyr 470 | Asp | Ile | Asp | Pro | Asn 475 | Ala | Gly | Pro | Phe | Ala 480 |
| Tyr | Asp | Leu | Pro | Leu 485 | Ser | Pro | Val | Thr | Ile 490 | Lys | Arg | Asn | Trp | Thr 495 | Ile |
| Thr | Arg | Leu | Asn 500 | Gly | Asp | Phe | Ala | Gln 505 | Leu | Asn | Leu | Lys | Ile 510 | Lys | Phe |
| Leu | Glu | Ala 515 | Gly | Ile | Tyr | Glu | Val 520 | Pro | Ile | Ile | Ile | Thr 525 | Asp | Ser | Gly |
| Asn | Pro 530 | Pro | Lys | Ser | Asn | Lys 535 | Ser | Ile | Leu | Arg | Val 540 | Arg | Val | Cys | Gln |
| Cys 545 | Asp | Phe | Asn | Gly | Asp 550 | Cys | Thr | Asp | Val | Asp 555 | Arg |     |     |     |     |

(2) INFORMATION FOR SEQ ID NO:99:

(i) SEQUENCE CHARACTERISTICS:
    (A) LENGTH: 105 amino acids
    (B) TYPE: amino acid
    (C) STRANDEDNESS: single
    (D) TOPOLOGY: linear ( i i ) MOLECULE TYPE: protein ( x i ) SEQUENCE DESCRIPTION: SEQ ID NO:99:

| Glu | Asp | Thr | Val | Tyr | Ser | Phe | Asp | Ile | Pro | Glu | Asn | Ala | Gln | Arg | Gly |
| 1 | | | | 5 | | | | | 10 | | | | | 15 | |

| Tyr | Gln | Val | Gly | Gln | Ile | Val | Ala | Arg | Asp | Ala | Asp | Leu | Gly | Gln | Asn |
| | | | 20 | | | | | 25 | | | | | 30 | | |

| Ala | Gln | Leu | Ser | Tyr | Gly | Val | Val | Ser | Asp | Trp | Ala | Asn | Asp | Val | Phe |
| | | 35 | | | | | 40 | | | | | 45 | | | |

| Ser | Leu | Asn | Pro | Gln | Thr | Gly | Met | Leu | Thr | Leu | Thr | Ala | Arg | Leu | Asp |
| | 50 | | | | | 55 | | | | | 60 | | | | |

| Tyr | Glu | Glu | Val | Gln | His | Tyr | Ile | Leu | Ile | Val | Gln | Ala | Gln | Asp | Asn |
| 65 | | | | | 70 | | | | | 75 | | | | | 80 |

| Gly | Gln | Pro | Ser | Leu | Ser | Thr | Thr | Ile | Thr | Val | Tyr | Cys | Asn | Val | Leu |
| | | | | 85 | | | | | 90 | | | | | 95 | |

| Asp | Leu | Asn | Asp | Asn | Ala | Pro | Ile | Phe | | | | | | | |
| | | | 100 | | | | | 105 | | | | | | | |

( 2 ) INFORMATION FOR SEQ ID NO:100:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:100:

| Asp | Xaa | Asp | Xaa | Gly | Xaa | Asn |
| 1 | | | | 5 | | |

( 2 ) INFORMATION FOR SEQ ID NO:101:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:101:

| Ala | Xaa | Asp | Xaa | Gly | Xaa | Pro |
| 1 | | | | 5 | | |

( 2 ) INFORMATION FOR SEQ ID NO:102:

( i ) SEQUENCE CHARACTERISTICS:
( A ) LENGTH: 4650 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 495..4103

( x i ) SEQUENCE DESCRIPTION: SEQ ID NO:102:

| CCTCTATTCG | ACATTCTCTT | TGGATTGTTT | TGCTATAACT | TGAAATTTGG | GATGTCACAA | 60 |
| ACGAAACTGT | CATCTGTTTC | CGCCAAACTG | TGGTTCTGCT | AATCTCCCAG | GCTGGCAGCA | 120 |
| TTGGAGACTT | GCTGACTTCT | TTCATCCCCC | ACTCTTTTCA | CCTGAAATTC | CTTTCCTTGG | 180 |

```
TTTTGCTCTA AGTCCTATGC TTCAGTCAGG GGCCAACCAA ATCTCACTGC CTCCTTTTA      240

TCATGAAGCC TTTGATCACT GATAGTTCTT TTTATATCTT GAAAAATCAC CCTTCCCAGT    300

ACAGTTAATA TTTAGTATCT CTACTCATCT TGGCACTTAC TCACAGCTCC ATAATTCAGT    360

CGTTTTCGTA CCTCTTCATG GTGATGGGGA GCCCTTTGGA GGTGGTGACT GTGCTTTATA    420

CTCCTCATGA TGCTTCACAT GTGGCAGGCG TGGAGTGCCC GGAGGCGGCC CTCCTGATTC    480

TGGGGCCTCC CAGG ATG GAG CCC CTG AGG CAC AGC CCA GGC CCT GGG GGG      530
              Met Glu Pro Leu Arg His Ser Pro Gly Pro Gly Gly
                1           5                  10

CAA CGG CTA CTG CTG CCC TCC ATG CTG CTA GCA CTG CTG CTC CTG CTG      578
Gln Arg Leu Leu Leu Pro Ser Met Leu Leu Ala Leu Leu Leu Leu Leu
         15              20                  25

GCT CCA TCC CCA GGC CAC GCC ACT CGG GTA GTG TAC AAG GTG CCG GAG      626
Ala Pro Ser Pro Gly His Ala Thr Arg Val Val Tyr Lys Val Pro Glu
         30              35                  40

GAA CAG CCA CCC AAC ACC CTC ATT GGG AGC CTC GCA GCC GAC TAT GGT      674
Glu Gln Pro Pro Asn Thr Leu Ile Gly Ser Leu Ala Ala Asp Tyr Gly
 45              50                  55                      60

TTT CCA GAT GTG GGG CAC CTG TAC AAG CTA GAG GTG GGT GCC CCG TAC      722
Phe Pro Asp Val Gly His Leu Tyr Lys Leu Glu Val Gly Ala Pro Tyr
                 65              70                  75

CTT CGC GTG GAT GGC AAG ACA GGT GAC ATT TTC ACC ACC GAG ACC TCC      770
Leu Arg Val Asp Gly Lys Thr Gly Asp Ile Phe Thr Thr Glu Thr Ser
             80              85                  90

ATC GAC CGT GAG GGG CTC CGT GAA TGC CAG AAC CAG CTC CCT GGT GAT      818
Ile Asp Arg Glu Gly Leu Arg Glu Cys Gln Asn Gln Leu Pro Gly Asp
             95              100                 105

CCC TGC ATC CTG GAG TTT GAG GTA TCT ATC ACA GAC CTC GTG CAG AAT      866
Pro Cys Ile Leu Glu Phe Glu Val Ser Ile Thr Asp Leu Val Gln Asn
    110                 115                 120

GCG AGC CCC CGG CTG CTA GAG GGC CAG ATA GAA GTA CAA GAC ATC AAT      914
Ala Ser Pro Arg Leu Leu Glu Gly Gln Ile Glu Val Gln Asp Ile Asn
125             130                 135                     140

GAC AAC ACA CCC AAC TTC GCC TCA CCA GTC ATC ACT CTG GCC ATC CCT      962
Asp Asn Thr Pro Asn Phe Ala Ser Pro Val Ile Thr Leu Ala Ile Pro
                145                 150                 155

GAG AAC ACC AAC ATC GGC TCA CTC TTC CCC ATC CCG CTG GCT TCA GAC      1010
Glu Asn Thr Asn Ile Gly Ser Leu Phe Pro Ile Pro Leu Ala Ser Asp
                160                 165                 170

CGT GAT GCT GGT CCC AAC GGT GTG GCA TCC TAT GAG CTG CAG GTG GCA      1058
Arg Asp Ala Gly Pro Asn Gly Val Ala Ser Tyr Glu Leu Gln Val Ala
        175                 180                 185

GAG GAC CAG GAG GAG AAG CAA CCA CAG CTC ATT GTG ATG GGC AAC CTG      1106
Glu Asp Gln Glu Glu Lys Gln Pro Gln Leu Ile Val Met Gly Asn Leu
    190                 195                 200

GAC CGT GAG CGC TGG GAC TCC TAT GAC CTC ACC ATC AAG GTG CAG GAT      1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG      1202
Gly Gly Ser Pro Pro Arg Ala Thr Ser Ala Leu Leu Arg Val Thr Val
                225                 230                 235

CTT GAC ACC AAT GAC AAC GCC CCC AAG TTT GAG CGG CCC TCC TAT GAG      1250
Leu Asp Thr Asn Asp Asn Ala Pro Lys Phe Glu Arg Pro Ser Tyr Glu
                240                 245                 250

GCC GAA CTA TCT GAG AAT AGC CCC ATA GGC CAC TCG GTC ATC CAG GTG      1298
Ala Glu Leu Ser Glu Asn Ser Pro Ile Gly His Ser Val Ile Gln Val
        255                 260                 265

AAG GCC AAT GAC TCA GAC CAA GGT GCC AAT GCA GAA ATC GAA TAC ACA      1346
```

```
                Lys Ala Asn Asp Ser Asp Gln Gly Ala Asn Ala Glu Ile Glu Tyr Thr
                270                 275                 280

TTC CAC CAG GCG CCC GAA GTT GTG AGG CGT CTT CTT CGA CTG GAC AGG              1394
Phe His Gln Ala Pro Glu Val Val Arg Arg Leu Leu Arg Leu Asp Arg
285                 290                 295                 300

AAC ACT GGA CTT ATC ACT GTT CAG GGC CCG GTG GAC CGT GAG GAC CTA              1442
Asn Thr Gly Leu Ile Thr Val Gln Gly Pro Val Asp Arg Glu Asp Leu
                305                 310                 315

AGC ACC CTG CGC TTC TCA GTG CTT GCT AAG GAC CGA GGC ACC AAC CCC              1490
Ser Thr Leu Arg Phe Ser Val Leu Ala Lys Asp Arg Gly Thr Asn Pro
        320                 325                 330

AAG AGT GCC CGT GCC CAG GTG GTT GTG ACC GTG AAG GAC ATG AAT GAC              1538
Lys Ser Ala Arg Ala Gln Val Val Val Thr Val Lys Asp Met Asn Asp
            335                 340                 345

AAT GCC CCC ACC ATT GAG ATC CGG GGC ATA GGG CTA GTG ACT CAT CAA              1586
Asn Ala Pro Thr Ile Glu Ile Arg Gly Ile Gly Leu Val Thr His Gln
350                 355                 360

GAT GGG ATG GCT AAC ATC TCA GAG GAT GTG GCA GAG GAG ACA GCT GTG              1634
Asp Gly Met Ala Asn Ile Ser Glu Asp Val Ala Glu Glu Thr Ala Val
365                 370                 375                 380

GCC CTG GTG CAG GTG TCT GAC CGA GAT GAG GGA GAG AAT GCA GCT GTC              1682
Ala Leu Val Gln Val Ser Asp Arg Asp Glu Gly Glu Asn Ala Ala Val
                385                 390                 395

ACC TGT GTG GTG GCA GGT GAT GTG CCC TTC CAG CTG CGC CAG GCC AGT              1730
Thr Cys Val Val Ala Gly Asp Val Pro Phe Gln Leu Arg Gln Ala Ser
                400                 405                 410

GAG ACA GGC AGT GAC AGC AAG AAG AAG TAT TTC CTG CAG ACT ACC ACC              1778
Glu Thr Gly Ser Asp Ser Lys Lys Lys Tyr Phe Leu Gln Thr Thr Thr
        415                 420                 425

CCG CTA GAC TAC GAG AAG GTC AAA GAC TAC ACC ATT GAG ATT GTG GCT              1826
Pro Leu Asp Tyr Glu Lys Val Lys Asp Tyr Thr Ile Glu Ile Val Ala
430                 435                 440

GTG GAC TCT GGC AAC CCC CCA CTC TCC AGC ACT AAC TCC CTC AAG GTG              1874
Val Asp Ser Gly Asn Pro Pro Leu Ser Ser Thr Asn Ser Leu Lys Val
445                 450                 455                 460

CAG GTG GTG GAC GTC AAT GAC AAC GCA CCT GTC TTC ACT CAG AGT GTC              1922
Gln Val Val Asp Val Asn Asp Asn Ala Pro Val Phe Thr Gln Ser Val
                465                 470                 475

ACT GAG GTC GCC TTC CCG GAA AAC AAC AAG CCT GGT GAA GTG ATT GCT              1970
Thr Glu Val Ala Phe Pro Glu Asn Asn Lys Pro Gly Glu Val Ile Ala
                480                 485                 490

GAG ATC ACT GCC AGT GAT GCT GAC TCT GGC TCT AAT GCT GAG CTG GTT              2018
Glu Ile Thr Ala Ser Asp Ala Asp Ser Gly Ser Asn Ala Glu Leu Val
        495                 500                 505

TAC TCT CTG GAG CCT GAG CCG GCT GCT AAG GGC CTC TTC ACC ATC TCA              2066
Tyr Ser Leu Glu Pro Glu Pro Ala Ala Lys Gly Leu Phe Thr Ile Ser
510                 515                 520

CCC GAG ACT GGA GAG ATC CAG GTG AAG ACA TCT CTG GAT CGG GAA CAG              2114
Pro Glu Thr Gly Glu Ile Gln Val Lys Thr Ser Leu Asp Arg Glu Gln
525                 530                 535                 540

CGG GAG AGC TAT GAG TTG AAG GTG GTG GCA GCT GAC CGG GGC AGT CCT              2162
Arg Glu Ser Tyr Glu Leu Lys Val Val Ala Ala Asp Arg Gly Ser Pro
                545                 550                 555

AGC CTC CAG GGC ACA GCC ACT GTC CTT GTC AAT GTG CTG GAC TGC AAT              2210
Ser Leu Gln Gly Thr Ala Thr Val Leu Val Asn Val Leu Asp Cys Asn
                560                 565                 570

GAC AAT GAC CCC AAA TTT ATG CTG AGT GGC TAC AAC TTC TCA GTG ATG              2258
Asp Asn Asp Pro Lys Phe Met Leu Ser Gly Tyr Asn Phe Ser Val Met
        575                 580                 585

GAG AAC ATG CCA GCA CTG AGT CCA GTG GGC ATG GTG ACT GTC ATT GAT              2306
```

```
Glu Asn Met Pro Ala Leu Ser Pro Val Gly Met Val Thr Val Ile Asp
590             595                 600

GGA GAC AAG GGG GAG AAT GCC CAG GTG CAG CTC TCA GTG GAG CAG GAC    2354
Gly Asp Lys Gly Glu Asn Ala Gln Val Gln Leu Ser Val Glu Gln Asp
605             610                 615                 620

AAC GGT GAC TTT GTT ATC CAG AAT GGC ACA GGC ACC ATC CTA TCC AGC    2402
Asn Gly Asp Phe Val Ile Gln Asn Gly Thr Gly Thr Ile Leu Ser Ser
                625                 630                 635

CTG AGC TTT GAT CGA GAG CAA CAA AGC ACC TAC ACC TTC CAG CTG AAG    2450
Leu Ser Phe Asp Arg Glu Gln Gln Ser Thr Tyr Thr Phe Gln Leu Lys
                640                 645                 650

GCA GTG GAT GGT GGC GTC CCA CCT CGC TCA GCT TAC GTT GGT GTC ACC    2498
Ala Val Asp Gly Gly Val Pro Pro Arg Ser Ala Tyr Val Gly Val Thr
                655                 660                 665

ATC AAT GTG CTG GAC GAG AAT GAC AAC GCA CCC TAT ATC ACT GCC CCT    2546
Ile Asn Val Leu Asp Glu Asn Asp Asn Ala Pro Tyr Ile Thr Ala Pro
        670                 675                 680

TCT AAC ACC TCT CAC AAG CTG CTG ACC CCC CAG ACA CGT CTT GGT GAG    2594
Ser Asn Thr Ser His Lys Leu Leu Thr Pro Gln Thr Arg Leu Gly Glu
685             690                 695                 700

ACG GTC AGC CAG GTG GCA GCC GAG GAC TTT GAC TCT GGT GTC AAT GCC    2642
Thr Val Ser Gln Val Ala Ala Glu Asp Phe Asp Ser Gly Val Asn Ala
                705                 710                 715

GAG CTG ATC TAC AGC ATT GCA GGT GGC AAC CCT TAT GGA CTC TTC CAG    2690
Glu Leu Ile Tyr Ser Ile Ala Gly Gly Asn Pro Tyr Gly Leu Phe Gln
                720                 725                 730

ATT GGG TCA CAT TCA GGT GCC ATC ACC CTG GAG AAG GAG ATT GAG CGG    2738
Ile Gly Ser His Ser Gly Ala Ile Thr Leu Glu Lys Glu Ile Glu Arg
                735                 740                 745

CGC CAC CAT GGG CTA CAC CGC CTG GTG GTG AAG GTC AGT GAC CGC GGC    2786
Arg His His Gly Leu His Arg Leu Val Val Lys Val Ser Asp Arg Gly
        750                 755                 760

AAG CCC CCA CGC TAT GGC ACA GCC TTG GTC CAT CTT TAT GTC AAT GAG    2834
Lys Pro Pro Arg Tyr Gly Thr Ala Leu Val His Leu Tyr Val Asn Glu
765             770                 775                 780

ACT CTG GCC AAC CGC ACG CTG CTG GAG ACC CTC CTG GGC CAC AGC CTG    2882
Thr Leu Ala Asn Arg Thr Leu Leu Glu Thr Leu Leu Gly His Ser Leu
                785                 790                 795

GAC ACG CCG CTG GAT ATT GAC ATT GCT GGG GAT CCA GAA TAT GAG CGC    2930
Asp Thr Pro Leu Asp Ile Asp Ile Ala Gly Asp Pro Glu Tyr Glu Arg
                800                 805                 810

TCC AAG CAG CGT GGC AAC ATT CTC TTT GGT GTG GTG GCT GGT GTG GTG    2978
Ser Lys Gln Arg Gly Asn Ile Leu Phe Gly Val Val Ala Gly Val Val
                815                 820                 825

GCC GTG GCC TTG CTC ATC GCC CTG GCG GTT CTT GTG CGC TAC TGC AGA    3026
Ala Val Ala Leu Leu Ile Ala Leu Ala Val Leu Val Arg Tyr Cys Arg
830                 835                 840

CAG CGG GAG GCC AAA AGT GGT TAC CAG GCT GGT AAG AAG GAG ACC AAG    3074
Gln Arg Glu Ala Lys Ser Gly Tyr Gln Ala Gly Lys Lys Glu Thr Lys
845             850                 855                 860

GAC CTG TAT GCC CCC AAG CCC AGT GGC AAG GCC TCC AAG GGA AAC AAA    3122
Asp Leu Tyr Ala Pro Lys Pro Ser Gly Lys Ala Ser Lys Gly Asn Lys
                865                 870                 875

AGC AAA GGC AAG AAG AGC AAG TCC CCA AAG CCC GTG AAG CCA GTG GAG    3170
Ser Lys Gly Lys Lys Ser Lys Ser Pro Lys Pro Val Lys Pro Val Glu
                880                 885                 890

GAC GAG GAT GAG GCC GGG CTG CAG AAG TCC CTC AAG TTC AAC CTG ATG    3218
Asp Glu Asp Glu Ala Gly Leu Gln Lys Ser Leu Lys Phe Asn Leu Met
                895                 900                 905

AGC GAT GCC CCT GGG GAC AGT CCC CGC ATC CAC CTG CCC CTC AAC TAC    3266
```

-continued

| | | | | | | | | | | | | | | | | |
|---|---|---|---|---|---|---|---|---|---|---|---|---|---|---|---|---|
| Ser | Asp | Ala | Pro | Gly | Asp | Ser | Pro | Arg | Ile | His | Leu | Pro | Leu | Asn | Tyr | |
| 910 | | | | | | 915 | | | | | 920 | | | | | |
| CCA | CCA | GGC | AGC | CCT | GAC | CTG | GGC | CGC | CAC | TAT | CGC | TCT | AAC | TCC | CCA | 3314 |
| Pro | Pro | Gly | Ser | Pro | Asp | Leu | Gly | Arg | His | Tyr | Arg | Ser | Asn | Ser | Pro | |
| 925 | | | | | 930 | | | | | 935 | | | | | 940 | |
| CTG | CCT | TCC | ATC | CAG | CTG | CAG | CCC | CAG | TCA | CCC | TCA | GCC | TCC | AAG | AAG | 3362 |
| Leu | Pro | Ser | Ile | Gln | Leu | Gln | Pro | Gln | Ser | Pro | Ser | Ala | Ser | Lys | Lys | |
| | | | | 945 | | | | | 950 | | | | | 955 | | |
| CAC | CAG | GTG | GTA | CAG | GAC | CTG | CCA | CCT | GCA | AAC | ACA | TTC | GTG | GGC | ACC | 3410 |
| His | Gln | Val | Val | Gln | Asp | Leu | Pro | Pro | Ala | Asn | Thr | Phe | Val | Gly | Thr | |
| | | | 960 | | | | | 965 | | | | | 970 | | | |
| GGG | GAC | ACC | ACG | TCC | ACG | GGC | TCT | GAG | CAG | TAC | TCC | GAC | TAC | AGC | TAC | 3458 |
| Gly | Asp | Thr | Thr | Ser | Thr | Gly | Ser | Glu | Gln | Tyr | Ser | Asp | Tyr | Ser | Tyr | |
| | | 975 | | | | | 980 | | | | | 985 | | | | |
| CGC | ACC | AAC | CCC | CCC | AAA | TAC | CCC | AGC | AAG | CAG | TTA | CCT | CAC | CGC | CGC | 3506 |
| Arg | Thr | Asn | Pro | Pro | Lys | Tyr | Pro | Ser | Lys | Gln | Leu | Pro | His | Arg | Arg | |
| | 990 | | | | | 995 | | | | | 1000 | | | | | |
| GTC | ACC | TTC | TCG | GCC | ACC | AGC | CAG | GCC | CAG | GAG | CTG | CAG | GAC | CCA | TCC | 3554 |
| Val | Thr | Phe | Ser | Ala | Thr | Ser | Gln | Ala | Gln | Glu | Leu | Gln | Asp | Pro | Ser | |
| 1005 | | | | | 1010 | | | | | 1015 | | | | | 1020 | |
| CAG | CAC | AGT | TAC | TAT | GAC | AGT | GGC | CTG | GAG | GAG | TCT | GAG | ACG | CCG | TCC | 3602 |
| Gln | His | Ser | Tyr | Tyr | Asp | Ser | Gly | Leu | Glu | Glu | Ser | Glu | Thr | Pro | Ser | |
| | | | | 1025 | | | | | 1030 | | | | | 1035 | | |
| AGC | AAG | TCA | TCC | TCA | GGG | CCT | CGA | CTC | GGT | CCC | CTG | GCC | CTG | CCT | GAG | 3650 |
| Ser | Lys | Ser | Ser | Ser | Gly | Pro | Arg | Leu | Gly | Pro | Leu | Ala | Leu | Pro | Glu | |
| | | | 1040 | | | | | 1045 | | | | | 1050 | | | |
| GAT | CAC | TAT | GAG | CGC | ACC | ACC | CCT | GAT | GGC | AGC | ATA | GGA | GAG | ATG | GAG | 3698 |
| Asp | His | Tyr | Glu | Arg | Thr | Thr | Pro | Asp | Gly | Ser | Ile | Gly | Glu | Met | Glu | |
| | | 1055 | | | | | 1060 | | | | | 1065 | | | | |
| CAC | CCC | GAG | AAT | GAC | CTT | CGC | CCT | TTG | CCT | GAT | GTC | GCC | ATG | ACA | GGC | 3746 |
| His | Pro | Glu | Asn | Asp | Leu | Arg | Pro | Leu | Pro | Asp | Val | Ala | Met | Thr | Gly | |
| | 1070 | | | | | 1075 | | | | | 1080 | | | | | |
| ACA | TGT | ACC | CGG | GAG | TGC | AGT | GAG | TTT | GGC | CAC | TCT | GAC | ACA | TGC | TGG | 3794 |
| Thr | Cys | Thr | Arg | Glu | Cys | Ser | Glu | Phe | Gly | His | Ser | Asp | Thr | Cys | Trp | |
| 1085 | | | | | 1090 | | | | | 1095 | | | | | 1100 | |
| ATG | CCT | GGC | CAG | TCA | TCT | CCC | AGC | CGC | CGG | ACC | AAG | AGC | AGC | GCC | CTC | 3842 |
| Met | Pro | Gly | Gln | Ser | Ser | Pro | Ser | Arg | Arg | Thr | Lys | Ser | Ser | Ala | Leu | |
| | | | | 1105 | | | | | 1110 | | | | | 1115 | | |
| AAA | CTC | TCC | ACC | TTC | ATG | CCT | TAC | CAG | GAC | CGA | GGA | GGG | CAG | GAG | CCT | 3890 |
| Lys | Leu | Ser | Thr | Phe | Met | Pro | Tyr | Gln | Asp | Arg | Gly | Gly | Gln | Glu | Pro | |
| | | | 1120 | | | | | 1125 | | | | | 1130 | | | |
| GCG | GGC | GCC | GGC | AGC | CCC | AGC | CCC | CCG | GAA | GAC | CGG | AAC | ACC | AAA | ACG | 3938 |
| Ala | Gly | Ala | Gly | Ser | Pro | Ser | Pro | Pro | Glu | Asp | Arg | Asn | Thr | Lys | Thr | |
| | | | 1135 | | | | | 1140 | | | | | 1145 | | | |
| GCC | CCC | GTG | CGC | CTC | CTG | CCC | TCC | TAC | AGT | GCC | TTC | TCC | CAC | AGT | AGC | 3986 |
| Ala | Pro | Val | Arg | Leu | Leu | Pro | Ser | Tyr | Ser | Ala | Phe | Ser | His | Ser | Ser | |
| | | 1150 | | | | | 1155 | | | | | 1160 | | | | |
| CAT | GAT | TCC | TGC | AAG | GAC | TCG | GCC | ACC | TTG | GAG | GAA | ATC | CCC | CTG | ACC | 4034 |
| His | Asp | Ser | Cys | Lys | Asp | Ser | Ala | Thr | Leu | Glu | Glu | Ile | Pro | Leu | Thr | |
| 1165 | | | | | 1170 | | | | | 1175 | | | | | 1180 | |
| CAG | ACC | TCG | GAC | TTC | CCA | CCC | GCA | GCC | ACA | CCG | GCA | TCT | GCC | CAG | ACG | 4082 |
| Gln | Thr | Ser | Asp | Phe | Pro | Pro | Ala | Ala | Thr | Pro | Ala | Ser | Ala | Gln | Thr | |
| | | | | 1185 | | | | | 1190 | | | | | 1195 | | |
| GCC | AAG | CGC | GAG | ATC | TAC | CTG | TGAGCCCCT | ACTGGCCGGC | CCCCCTCCCC | | | | | | | 4133 |
| Ala | Lys | Arg | Glu | Ile | Tyr | Leu | | | | | | | | | | |
| | | | 1200 | | | | | | | | | | | | | |

CAGCGCCGGC CAGCTCCCAA ATGCCCATTC CAGGGCCTCA CTCTCCACCC CTTCAGCGTG 4193

GACTTCCTGC CAGGGCCCAA GTGGGGGTAT CACTGACCTC ATGACCACGC TGGCCCTTCT 4253

CCCATGCAGG GTCCAGGTCC TCTCCCCTCA TTTCCATCTC CAGCCCAGG GGCCCCTTCC 4313

```
CCTTTATGGG GCTTCCCCCA GCTGATGCCC AAGAGGGCTC CTCTGCAATG ACTGGGCTCC    4373

TTCCCTTGAC TTCCAGGGAG CACCCCCTCG ATTTGGGCAG ATGGTGGAGT CAAGGGTGGG    4433

CAGCGTACTT CTAACTCATT GTTTCCCTCA TGGCCGACCA GGGCGGGGAT AGCATGCCCA    4493

ATTTTAGCCC TGAAGCAGGG CTGAACTGGG GAGCCCCTTT CCCTGGGAGC TCCCAGAGGA    4553

AACTCTTGAC CACCAGTGGC TCCCTGAAGG GCTTTTGTTA CCAAAGGTGG GGTAGGGACG    4613

GGGGTGGGAG TGGAGCGGAG GCCTTGTTTT CCCGTGG                              4650
```

( 2 ) INFORMATION FOR SEQ ID NO:103:

( i ) SEQUENCE CHARACTERISTICS:
      ( A ) LENGTH: 1203 amino acids
      ( B ) TYPE: amino acid
      ( D ) TOPOLOGY: linear ( i i ) MOLECULE TYPE: protein ( x i ) SEQUENCE DESCRIPTION: SEQ ID NO:103:

```
Met Glu Pro Leu Arg His Ser Pro Gly Pro Gly Gly Gln Arg Leu Leu
 1               5                  10                  15

Leu Pro Ser Met Leu Leu Ala Leu Leu Leu Leu Ala Pro Ser Pro
             20                  25                  30

Gly His Ala Thr Arg Val Val Tyr Lys Val Pro Glu Gln Pro Pro
         35                  40                  45

Asn Thr Leu Ile Gly Ser Leu Ala Ala Asp Tyr Gly Phe Pro Asp Val
 50                  55                  60

Gly His Leu Tyr Lys Leu Glu Val Gly Ala Pro Tyr Leu Arg Val Asp
 65                  70                  75                  80

Gly Lys Thr Gly Asp Ile Phe Thr Thr Glu Thr Ser Ile Asp Arg Glu
             85                  90                  95

Gly Leu Arg Glu Cys Gln Asn Gln Leu Pro Gly Asp Pro Cys Ile Leu
            100                 105                 110

Glu Phe Glu Val Ser Ile Thr Asp Leu Val Gln Asn Ala Ser Pro Arg
            115                 120                 125

Leu Leu Glu Gly Gln Ile Glu Val Gln Asp Ile Asn Asp Asn Thr Pro
        130                 135                 140

Asn Phe Ala Ser Pro Val Ile Thr Leu Ala Ile Pro Glu Asn Thr Asn
145                 150                 155                 160

Ile Gly Ser Leu Phe Pro Ile Pro Leu Ala Ser Asp Arg Asp Ala Gly
                165                 170                 175

Pro Asn Gly Val Ala Ser Tyr Glu Leu Gln Val Ala Glu Asp Gln Glu
            180                 185                 190

Glu Lys Gln Pro Gln Leu Ile Val Met Gly Asn Leu Asp Arg Glu Arg
        195                 200                 205

Trp Asp Ser Tyr Asp Leu Thr Ile Lys Val Gln Asp Gly Gly Ser Pro
    210                 215                 220

Pro Arg Ala Thr Ser Ala Leu Leu Arg Val Thr Val Leu Asp Thr Asn
225                 230                 235                 240

Asp Asn Ala Pro Lys Phe Glu Arg Pro Ser Tyr Glu Ala Glu Leu Ser
                245                 250                 255

Glu Asn Ser Pro Ile Gly His Ser Val Ile Gln Val Lys Ala Asn Asp
            260                 265                 270

Ser Asp Gln Gly Ala Asn Ala Glu Ile Glu Tyr Thr Phe His Gln Ala
        275                 280                 285

Pro Glu Val Val Arg Arg Leu Leu Arg Leu Asp Arg Asn Thr Gly Leu
```

-continued

```
              290                      295                         300
Ile Thr Val Gln Gly Pro Val Asp Arg Glu Asp Leu Ser Thr Leu Arg
305                 310                 315                 320
Phe Ser Val Leu Ala Lys Asp Arg Gly Thr Asn Pro Lys Ser Ala Arg
                325                 330                 335
Ala Gln Val Val Val Thr Val Lys Asp Met Asn Asp Asn Ala Pro Thr
                340                 345                 350
Ile Glu Ile Arg Gly Ile Gly Leu Val Thr His Gln Asp Gly Met Ala
                355                 360                 365
Asn Ile Ser Glu Asp Val Ala Glu Thr Ala Val Ala Leu Val Gln
    370                 375                 380
Val Ser Asp Arg Asp Glu Gly Glu Asn Ala Ala Val Thr Cys Val Val
385                 390                 395                 400
Ala Gly Asp Val Pro Phe Gln Leu Arg Gln Ala Ser Glu Thr Gly Ser
                405                 410                 415
Asp Ser Lys Lys Lys Tyr Phe Leu Gln Thr Thr Pro Leu Asp Tyr
                420                 425                 430
Glu Lys Val Lys Asp Tyr Thr Ile Glu Ile Val Ala Val Asp Ser Gly
            435                 440                 445
Asn Pro Pro Leu Ser Ser Thr Asn Ser Leu Lys Val Gln Val Val Asp
    450                 455                 460
Val Asn Asp Asn Ala Pro Val Phe Thr Gln Ser Val Thr Glu Val Ala
465                 470                 475                 480
Phe Pro Glu Asn Asn Lys Pro Gly Glu Val Ile Ala Glu Ile Thr Ala
                485                 490                 495
Ser Asp Ala Asp Ser Gly Ser Asn Ala Glu Leu Val Tyr Ser Leu Glu
                500                 505                 510
Pro Glu Pro Ala Ala Lys Gly Leu Phe Thr Ile Ser Pro Glu Thr Gly
            515                 520                 525
Glu Ile Gln Val Lys Thr Ser Leu Asp Arg Glu Gln Arg Glu Ser Tyr
    530                 535                 540
Glu Leu Lys Val Val Ala Ala Asp Arg Gly Ser Pro Ser Leu Gln Gly
545                 550                 555                 560
Thr Ala Thr Val Leu Val Asn Val Leu Asp Cys Asn Asp Asn Asp Pro
                565                 570                 575
Lys Phe Met Leu Ser Gly Tyr Asn Phe Ser Val Met Glu Asn Met Pro
            580                 585                 590
Ala Leu Ser Pro Val Gly Met Val Thr Val Ile Asp Gly Asp Lys Gly
        595                 600                 605
Glu Asn Ala Gln Val Gln Leu Ser Val Glu Gln Asp Asn Gly Asp Phe
    610                 615                 620
Val Ile Gln Asn Gly Thr Gly Thr Ile Leu Ser Ser Leu Ser Phe Asp
625                 630                 635                 640
Arg Glu Gln Gln Ser Thr Tyr Thr Phe Gln Leu Lys Ala Val Asp Gly
                645                 650                 655
Gly Val Pro Pro Arg Ser Ala Tyr Val Gly Val Thr Ile Asn Val Leu
                660                 665                 670
Asp Glu Asn Asp Asn Ala Pro Tyr Ile Thr Ala Pro Ser Asn Thr Ser
            675                 680                 685
His Lys Leu Leu Thr Pro Gln Thr Arg Leu Gly Glu Thr Val Ser Gln
    690                 695                 700
Val Ala Ala Glu Asp Phe Asp Ser Gly Val Asn Ala Glu Leu Ile Tyr
705                 710                 715                 720
```

| | | | | | | | | | | | | | | |
|---|---|---|---|---|---|---|---|---|---|---|---|---|---|---|
| Ser | Ile | Ala | Gly | Gly | Asn | Pro | Tyr | Gly | Leu | Phe | Gln | Ile | Gly | Ser | His |
| | | | | 725 | | | | 730 | | | | | | 735 | |
| Ser | Gly | Ala | Ile | Thr | Leu | Glu | Lys | Glu | Ile | Glu | Arg | Arg | His | His | Gly |
| | | | 740 | | | | 745 | | | | | | 750 | | |
| Leu | His | Arg | Leu | Val | Val | Lys | Val | Ser | Asp | Arg | Gly | Lys | Pro | Pro | Arg |
| | | 755 | | | | 760 | | | | | 765 | | | | |
| Tyr | Gly | Thr | Ala | Leu | Val | His | Leu | Tyr | Val | Asn | Glu | Thr | Leu | Ala | Asn |
| | 770 | | | | | 775 | | | | | 780 | | | | |
| Arg | Thr | Leu | Leu | Glu | Thr | Leu | Leu | Gly | His | Ser | Leu | Asp | Thr | Pro | Leu |
| 785 | | | | | 790 | | | | | 795 | | | | | 800 |
| Asp | Ile | Asp | Ile | Ala | Gly | Asp | Pro | Glu | Tyr | Glu | Arg | Ser | Lys | Gln | Arg |
| | | | | 805 | | | | | 810 | | | | | 815 | |
| Gly | Asn | Ile | Leu | Phe | Gly | Val | Val | Ala | Gly | Val | Val | Ala | Val | Ala | Leu |
| | | | 820 | | | | | 825 | | | | | 830 | | |
| Leu | Ile | Ala | Leu | Ala | Val | Leu | Val | Arg | Tyr | Cys | Arg | Gln | Arg | Glu | Ala |
| | | 835 | | | | | 840 | | | | | 845 | | | |
| Lys | Ser | Gly | Tyr | Gln | Ala | Gly | Lys | Lys | Glu | Thr | Lys | Asp | Leu | Tyr | Ala |
| | 850 | | | | | 855 | | | | | 860 | | | | |
| Pro | Lys | Pro | Ser | Gly | Lys | Ala | Ser | Lys | Gly | Asn | Lys | Ser | Lys | Gly | Lys |
| 865 | | | | 870 | | | | | 875 | | | | | 880 | |
| Lys | Ser | Lys | Ser | Pro | Lys | Pro | Val | Lys | Pro | Val | Glu | Asp | Glu | Asp | Glu |
| | | | | 885 | | | | | 890 | | | | | 895 | |
| Ala | Gly | Leu | Gln | Lys | Ser | Leu | Lys | Phe | Asn | Leu | Met | Ser | Asp | Ala | Pro |
| | | | 900 | | | | | 905 | | | | | 910 | | |
| Gly | Asp | Ser | Pro | Arg | Ile | His | Leu | Pro | Leu | Asn | Tyr | Pro | Pro | Gly | Ser |
| | | 915 | | | | | 920 | | | | | 925 | | | |
| Pro | Asp | Leu | Gly | Arg | His | Tyr | Arg | Ser | Asn | Ser | Pro | Leu | Pro | Ser | Ile |
| | 930 | | | | | 935 | | | | | 940 | | | | |
| Gln | Leu | Gln | Pro | Gln | Ser | Pro | Ser | Ala | Ser | Lys | Lys | His | Gln | Val | Val |
| 945 | | | | | 950 | | | | | 955 | | | | | 960 |
| Gln | Asp | Leu | Pro | Pro | Ala | Asn | Thr | Phe | Val | Gly | Thr | Gly | Asp | Thr | Thr |
| | | | | 965 | | | | | 970 | | | | | 975 | |
| Ser | Thr | Gly | Ser | Glu | Gln | Tyr | Ser | Asp | Tyr | Ser | Tyr | Arg | Thr | Asn | Pro |
| | | | 980 | | | | | 985 | | | | | 990 | | |
| Pro | Lys | Tyr | Pro | Ser | Lys | Gln | Leu | Pro | His | Arg | Arg | Val | Thr | Phe | Ser |
| | | 995 | | | | | 1000 | | | | | 1005 | | | |
| Ala | Thr | Ser | Gln | Ala | Gln | Glu | Leu | Gln | Asp | Pro | Ser | Gln | His | Ser | Tyr |
| | 1010 | | | | | 1015 | | | | | 1020 | | | | |
| Tyr | Asp | Ser | Gly | Leu | Glu | Glu | Ser | Glu | Thr | Pro | Ser | Ser | Lys | Ser | Ser |
| 1025 | | | | | 1030 | | | | | 1035 | | | | | 1040 |
| Ser | Gly | Pro | Arg | Leu | Gly | Pro | Leu | Ala | Leu | Pro | Glu | Asp | His | Tyr | Glu |
| | | | | 1045 | | | | | 1050 | | | | | 1055 | |
| Arg | Thr | Thr | Pro | Asp | Gly | Ser | Ile | Gly | Glu | Met | Glu | His | Pro | Glu | Asn |
| | | | 1060 | | | | | 1065 | | | | | 1070 | | |
| Asp | Leu | Arg | Pro | Leu | Pro | Asp | Val | Ala | Met | Thr | Gly | Thr | Cys | Thr | Arg |
| | | 1075 | | | | | 1080 | | | | | 1085 | | | |
| Glu | Cys | Ser | Glu | Phe | Gly | His | Ser | Asp | Thr | Cys | Trp | Met | Pro | Gly | Gln |
| | | 1090 | | | | | 1095 | | | | | 1100 | | | |
| Ser | Ser | Pro | Ser | Arg | Arg | Thr | Lys | Ser | Ser | Ala | Leu | Lys | Leu | Ser | Thr |
| 1105 | | | | | 1110 | | | | | 1115 | | | | | 1120 |
| Phe | Met | Pro | Tyr | Gln | Asp | Arg | Gly | Gln | Glu | Pro | Ala | Gly | Ala | Gly |
| | | | | 1125 | | | | | 1130 | | | | | 1135 | |
| Ser | Pro | Ser | Pro | Pro | Glu | Asp | Arg | Asn | Thr | Lys | Thr | Ala | Pro | Val | Arg |
| | | | 1140 | | | | | 1145 | | | | | 1150 | | |

```
Leu Leu Pro Ser Tyr Ser Ala Phe Ser His Ser Ser His Asp Ser Cys
        1155            1160            1165

Lys Asp Ser Ala Thr Leu Glu Glu Ile Pro Leu Thr Gln Thr Ser Asp
1170            1175            1180

Phe Pro Pro Ala Ala Thr Pro Ala Ser Ala Gln Thr Ala Lys Arg Glu
1185            1190            1195            1200

Ile Tyr Leu
```

( 2 ) INFORMATION FOR SEQ ID NO:104:

( i ) SEQUENCE CHARACTERISTICS:
        ( A ) LENGTH: 2789 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2622

( x i ) SEQUENCE DESCRIPTION: SEQ ID NO:104:

```
CGAAAGCCAT GTCGGACTCG TCGCCCAGCG CCCAAGCGCT AACCCGCTGA AAGTTTCTCA      60

GCGAAATCTC AGGGACGATC TGGACCCCGC TGAGAGGAAC TGCTTTTGAG TGAG ATG       117
                                                             Met
                                                             1

GTC CCA GAG GCC TGG AGG AGC GGA CTG GTA AGC ACC GGG AGG GTA GTG      165
Val Pro Glu Ala Trp Arg Ser Gly Leu Val Ser Thr Gly Arg Val Val
        5                   10                  15

GGA GTT TTG CTT CTG CTT GGT GCC TTG AAC AAG GCT TCC ACG GTC ATT      213
Gly Val Leu Leu Leu Leu Gly Ala Leu Asn Lys Ala Ser Thr Val Ile
        20                  25                  30

CAC TAT GAG ATC CCG GAG GAA AGA GAG AAG GGT TTC GCT GTG GGC AAC      261
His Tyr Glu Ile Pro Glu Glu Arg Glu Lys Gly Phe Ala Val Gly Asn
    35                  40                  45

GTG GTC GCG AAC CTT GGT TTG GAT CTC GGT AGC CTC TCA GCC CGC AGG      309
Val Val Ala Asn Leu Gly Leu Asp Leu Gly Ser Leu Ser Ala Arg Arg
50                  55                  60                  65

TTC CCG GTG GTG TCT GGA GCT AGC CGA AGA TTC TTT GAG GTG AAC CGG      357
Phe Pro Val Val Ser Gly Ala Ser Arg Arg Phe Phe Glu Val Asn Arg
                70                  75                  80

GAG ACC GGA GAG ATG TTT GTG AAC GAC CGT CTG GAT CGA GAG GAG CTG      405
Glu Thr Gly Glu Met Phe Val Asn Asp Arg Leu Asp Arg Glu Glu Leu
            85                  90                  95

TGT GGG ACA CTG CCC TCT TGC ACT GTA ACT CTG GAG TTG GTA GTG GAG      453
Cys Gly Thr Leu Pro Ser Cys Thr Val Thr Leu Glu Leu Val Val Glu
        100                 105                 110

AAC CCG CTG GAG CTG TTC AGC GTG GAA GTG GTG ATC CAG GAC ATC AAC      501
Asn Pro Leu Glu Leu Phe Ser Val Glu Val Val Ile Gln Asp Ile Asn
    115                 120                 125

GAC AAC AAT CCT GCT TTC CCT ACC CAG GAA ATG AAA TTG GAG ATT AGC      549
Asp Asn Asn Pro Ala Phe Pro Thr Gln Glu Met Lys Leu Glu Ile Ser
130                 135                 140                 145

GAG GCC GTG GCT CCG GGG ACG CGC TTT CCG CTC GAG AGC GCG CAC GAT      597
Glu Ala Val Ala Pro Gly Thr Arg Phe Pro Leu Glu Ser Ala His Asp
                150                 155                 160

CCC GAT CTG GGA AGC AAC TCT TTA CAA ACC TAT GAG CTG AGC CGA AAT      645
Pro Asp Leu Gly Ser Asn Ser Leu Gln Thr Tyr Glu Leu Ser Arg Asn
            165                 170                 175

GAA TAC TTT GCG CTT CGC GTG CAG ACG CGG GAG GAC AGC ACC AAG TAC      693
```

-continued

```
                    Glu Tyr Phe Ala Leu Arg Val Gln Thr Arg Glu Asp Ser Thr Lys Tyr
                                180                 185                 190

GCG GAG CTG GTG TTG GAG CGC GCC CTG GAC CGA GAA CGG GAG CCT AGT                              741
Ala Glu Leu Val Leu Glu Arg Ala Leu Asp Arg Glu Arg Glu Pro Ser
    195                 200                 205

CTC CAG TTA GTG CTG ACG GCG TTG GAC GGA GGG ACC CCA GCT CTC TCC                              789
Leu Gln Leu Val Leu Thr Ala Leu Asp Gly Gly Thr Pro Ala Leu Ser
210                 215                 220                 225

GCC AGC CTG CCT ATT CAC ATC AAG GTG CTG GAC GCG AAT GAC AAT GCG                              837
Ala Ser Leu Pro Ile His Ile Lys Val Leu Asp Ala Asn Asp Asn Ala
            230                 235                 240

CCT GTC TTC AAC CAG TCC TTG TAC CGG GCG CGC GTT CCT GGA GGA TGC                              885
Pro Val Phe Asn Gln Ser Leu Tyr Arg Ala Arg Val Pro Gly Gly Cys
                245                 250                 255

ACC TCC GGC ACG CGC GTG GTA CAA GTC CTT GCA ACG GAT CTG GAT GAA                              933
Thr Ser Gly Thr Arg Val Val Gln Val Leu Ala Thr Asp Leu Asp Glu
        260                 265                 270

GGC CCC AAC GGT GAA ATT ATT TAC TCC TTC GGC AGC CAC AAC CGC GCC                              981
Gly Pro Asn Gly Glu Ile Ile Tyr Ser Phe Gly Ser His Asn Arg Ala
    275                 280                 285

GGC GTG CGG CAA CTA TTC GCC TTA GAC CTT GTA ACC GGG ATG CTG ACA                             1029
Gly Val Arg Gln Leu Phe Ala Leu Asp Leu Val Thr Gly Met Leu Thr
290                 295                 300                 305

ATC AAG GGT CGG CTG GAC TTC GAG GAC ACC AAA CTC CAT GAG ATT TAC                             1077
Ile Lys Gly Arg Leu Asp Phe Glu Asp Thr Lys Leu His Glu Ile Tyr
            310                 315                 320

ATC CAG GCC AAA GAC AAG GGC GCC AAT CCC GAA GGA GCA CAT TGC AAA                             1125
Ile Gln Ala Lys Asp Lys Gly Ala Asn Pro Glu Gly Ala His Cys Lys
                325                 330                 335

GTG TTG GTG GAG GTT GTG GAT GTG AAT GAC AAC GCC CCG GAG ATC ACA                             1173
Val Leu Val Glu Val Val Asp Val Asn Asp Asn Ala Pro Glu Ile Thr
        340                 345                 350

GTC ACC TCC GTG TAC AGC CCA GTA CCC GAG GAT GCC TCT GGG ACT GTC                             1221
Val Thr Ser Val Tyr Ser Pro Val Pro Glu Asp Ala Ser Gly Thr Val
    355                 360                 365

ATC GCT TTG CTC AGT GTG ACT GAC CTG GAT GCT GGC GAG AAC GGG CTG                             1269
Ile Ala Leu Leu Ser Val Thr Asp Leu Asp Ala Gly Glu Asn Gly Leu
370                 375                 380                 385

GTG ACC TGC GAA GTT CCA CCG GGT CTC CCT TTC AGC CTT ACT TCT TCC                             1317
Val Thr Cys Glu Val Pro Pro Gly Leu Pro Phe Ser Leu Thr Ser Ser
            390                 395                 400

CTC AAG AAT TAC TTC ACT TTG AAA ACC AGT GCA GAC CTG GAT CGG GAG                             1365
Leu Lys Asn Tyr Phe Thr Leu Lys Thr Ser Ala Asp Leu Asp Arg Glu
                405                 410                 415

ACT GTG CCA GAA TAC AAC CTC AGC ATC ACC GCC CGA GAC GCC GGA ACC                             1413
Thr Val Pro Glu Tyr Asn Leu Ser Ile Thr Ala Arg Asp Ala Gly Thr
        420                 425                 430

CCT TCC CTC TCA GCC CTT ACA ATA GTG CGT GTT CAA GTG TCC GAC ATC                             1461
Pro Ser Leu Ser Ala Leu Thr Ile Val Arg Val Gln Val Ser Asp Ile
    435                 440                 445

AAT GAC AAC CCT CCA CAA TCT TCT CAA TCT TCC TAC GAC GTT TAC ATT                             1509
Asn Asp Asn Pro Pro Gln Ser Ser Gln Ser Ser Tyr Asp Val Tyr Ile
450                 455                 460                 465

GAA GAA AAC AAC CTC CCC GGG GCT CCA ATA CTA AAC CTA AGT GTC TGG                             1557
Glu Glu Asn Asn Leu Pro Gly Ala Pro Ile Leu Asn Leu Ser Val Trp
            470                 475                 480

GAC CCC GAC GCC CCG CAG AAT GCT CGG CTT TCT TTC TTT CTC TTG GAG                             1605
Asp Pro Asp Ala Pro Gln Asn Ala Arg Leu Ser Phe Phe Leu Leu Glu
                485                 490                 495

CAA GGA GCT GAA ACC GGG CTA GTG GGT CGC TAT TTC ACA ATA AAT CGT                             1653
```

-continued

```
        Gln Gly Ala Glu Thr Gly Leu Val Gly Arg Tyr Phe Thr Ile Asn Arg
                500             505             510

GAC AAT GGC ATA GTG TCA TCC TTA GTG CCC CTA GAC TAT GAG GAT CGG          1701
Asp Asn Gly Ile Val Ser Ser Leu Val Pro Leu Asp Tyr Glu Asp Arg
515             520             525

CGG GAA TTT GAA TTA ACA GCT CAT ATC AGC GAT GGG GGC ACC CCG GTC          1749
Arg Glu Phe Glu Leu Thr Ala His Ile Ser Asp Gly Gly Thr Pro Val
530             535             540             545

CTA GCC ACC AAC ATC AGC GTG AAC ATA TTT GTC ACT GAT CGC AAT GAC          1797
Leu Ala Thr Asn Ile Ser Val Asn Ile Phe Val Thr Asp Arg Asn Asp
                550             555             560

AAT GCC CCC CAG GTC CTA TAT CCT CGG CCA GGT GGG AGC TCG GTG GAG          1845
Asn Ala Pro Gln Val Leu Tyr Pro Arg Pro Gly Gly Ser Ser Val Glu
            565             570             575

ATG CTG CCT CGA GGT ACC TCA GCT GGC CAC CTA GTG TCA CGG GTG GTA          1893
Met Leu Pro Arg Gly Thr Ser Ala Gly His Leu Val Ser Arg Val Val
        580             585             590

GGC TGG GAC GCG GAT GCA GGG CAC AAT GCC TGG CTC TCC TAC AGT CTC          1941
Gly Trp Asp Ala Asp Ala Gly His Asn Ala Trp Leu Ser Tyr Ser Leu
    595             600             605

TTT GGA TCC CCT AAC CAG AGC CTT TTT GCC ATA GGG CTG CAC ACT GGT          1989
Phe Gly Ser Pro Asn Gln Ser Leu Phe Ala Ile Gly Leu His Thr Gly
610             615             620             625

CAA ATC AGT ACT GCC CGT CCA GTC CAA GAC ACA GAT TCA CCC AGG CAG          2037
Gln Ile Ser Thr Ala Arg Pro Val Gln Asp Thr Asp Ser Pro Arg Gln
                630             635             640

ACT CTC ACT GTC TTG ATC AAA GAC AAT GGG GAG CCT TCG CTC TCC ACC          2085
Thr Leu Thr Val Leu Ile Lys Asp Asn Gly Glu Pro Ser Leu Ser Thr
            645             650             655

ACT GCT ACC CTC ACT GTG TCA GTA ACC GAG GAC TCT CCT GAA GCC CGA          2133
Thr Ala Thr Leu Thr Val Ser Val Thr Glu Asp Ser Pro Glu Ala Arg
        660             665             670

GCC GAG TTC CCC TCT GGC TCT GCC CCC CGG GAG CAG AAA AAA AAT CTC          2181
Ala Glu Phe Pro Ser Gly Ser Ala Pro Arg Glu Gln Lys Lys Asn Leu
    675             680             685

ACC TTT TAT CTA CTT CTT TCT CTA ATC CTG GTT TCT GTG GGC TTC GTG          2229
Thr Phe Tyr Leu Leu Leu Ser Leu Ile Leu Val Ser Val Gly Phe Val
690             695             700             705

GTC ACA GTG TTC GGA GTA ATC ATA TTC AAA GTT TAC AAG TGG AAG CAG          2277
Val Thr Val Phe Gly Val Ile Ile Phe Lys Val Tyr Lys Trp Lys Gln
                710             715             720

TCT AGA GAC CTA TAC CGA GCC CCG GTG AGC TCA CTG TAC CGA ACA CCA          2325
Ser Arg Asp Leu Tyr Arg Ala Pro Val Ser Ser Leu Tyr Arg Thr Pro
            725             730             735

GGG CCC TCC TTG CAC GCG GAC GCC GTG CGG GGA GGC CTG ATG TCG CCG          2373
Gly Pro Ser Leu His Ala Asp Ala Val Arg Gly Gly Leu Met Ser Pro
        740             745             750

CAC CTT TAC CAT CAG GTG TAT CTC ACC ACG GAC TCC CGC CGC AGC GAC          2421
His Leu Tyr His Gln Val Tyr Leu Thr Thr Asp Ser Arg Arg Ser Asp
    755             760             765

CCG CTG CTG AAG AAA CCT GGT GCA GCC AGT CCA CTG GCC AGC CGC CAG          2469
Pro Leu Leu Lys Lys Pro Gly Ala Ala Ser Pro Leu Ala Ser Arg Gln
770             775             780             785

AAC ACG CTG CGG AGC TGT GAT CCG GTG TTC TAT AGG CAG GTG TTG GGT          2517
Asn Thr Leu Arg Ser Cys Asp Pro Val Phe Tyr Arg Gln Val Leu Gly
                790             795             800

GCA GAG AGC GCC CCT CCC GGA CAG GTA AGG TTT AGC AAG TCA TGC TTG          2565
Ala Glu Ser Ala Pro Pro Gly Gln Val Arg Phe Ser Lys Ser Cys Leu
            805             810             815

ACC CTG TTA GTG CCT TTT TAT TCC TAC ATC ATA TTG AGA AGG CTG GAG          2613
```

|   |   |   |   |   |   |   |   |   |   |   |   |   |   |   |
|---|---|---|---|---|---|---|---|---|---|---|---|---|---|---|
| Thr | Leu | Leu<br>820 | Val | Pro | Phe | Tyr | Ser<br>825 | Tyr | Ile | Ile | Leu | Arg<br>830 | Arg | Leu Glu |

```
CTG TTT TTT TAGTGATGAA GATGTTTCC TGGTGATGCA TTCACACTTT                2662
Leu Phe Phe
    835

CAACTGGCTC TTCCTAGATC AAAGTTAGTG CCTTTGTGAG ATGGTGGCCT GCCAGAGTGT     2722

GGTTTGTGGT CCCATTTCAG GGGGAAGATA CTTGACTCAT CTGTGGACCT AATTCACATC     2782

CTCAGCG                                                               2789
```

(2) INFORMATION FOR SEQ ID NO:105:

(i) SEQUENCE CHARACTERISTICS:
        (A) LENGTH: 836 amino acids
        (B) TYPE: amino acid
        (D) TOPOLOGY: linear (ii) MOLECULE TYPE: protein (xi) SEQUENCE DESCRIPTION: SEQ ID NO:105:

| Met<br>1 | Val | Pro | Glu | Ala<br>5 | Trp | Arg | Ser | Gly | Leu<br>10 | Val | Ser | Thr | Gly | Arg<br>15 | Val |
|---|---|---|---|---|---|---|---|---|---|---|---|---|---|---|---|
| Val | Gly | Val | Leu<br>20 | Leu | Leu | Leu | Gly | Ala<br>25 | Leu | Asn | Lys | Ala | Ser<br>30 | Thr | Val |
| Ile | His | Tyr<br>35 | Glu | Ile | Pro | Glu | Glu<br>40 | Arg | Glu | Lys | Gly | Phe<br>45 | Ala | Val | Gly |
| Asn | Val<br>50 | Val | Ala | Asn | Leu | Gly<br>55 | Leu | Asp | Leu | Gly | Ser<br>60 | Leu | Ser | Ala | Arg |
| Arg<br>65 | Phe | Pro | Val | Val | Ser<br>70 | Gly | Ala | Ser | Arg | Arg<br>75 | Phe | Phe | Glu | Val | Asn<br>80 |
| Arg | Glu | Thr | Gly | Glu<br>85 | Met | Phe | Val | Asn | Asp<br>90 | Arg | Leu | Asp | Arg | Glu<br>95 | Glu |
| Leu | Cys | Gly | Thr<br>100 | Leu | Pro | Ser | Cys | Thr<br>105 | Val | Thr | Leu | Glu | Leu<br>110 | Val | Val |
| Glu | Asn | Pro<br>115 | Leu | Glu | Leu | Phe | Ser<br>120 | Val | Glu | Val | Val | Ile<br>125 | Gln | Asp | Ile |
| Asn | Asp<br>130 | Asn | Asn | Pro | Ala | Phe<br>135 | Pro | Thr | Gln | Glu | Met<br>140 | Lys | Leu | Glu | Ile |
| Ser<br>145 | Glu | Ala | Val | Ala | Pro<br>150 | Gly | Thr | Arg | Phe | Pro<br>155 | Leu | Glu | Ser | Ala | His<br>160 |
| Asp | Pro | Asp | Leu | Gly<br>165 | Ser | Asn | Ser | Leu | Gln<br>170 | Thr | Tyr | Glu | Leu | Ser<br>175 | Arg |
| Asn | Glu | Tyr | Phe<br>180 | Ala | Leu | Arg | Val | Gln<br>185 | Thr | Arg | Glu | Asp | Ser<br>190 | Thr | Lys |
| Tyr | Ala | Glu<br>195 | Leu | Val | Leu | Glu | Arg<br>200 | Ala | Leu | Asp | Arg | Glu<br>205 | Arg | Glu | Pro |
| Ser | Leu<br>210 | Gln | Leu | Val | Leu | Thr<br>215 | Ala | Leu | Asp | Gly | Gly<br>220 | Thr | Pro | Ala | Leu |
| Ser<br>225 | Ala | Ser | Leu | Pro | Ile<br>230 | His | Ile | Lys | Val | Leu<br>235 | Asp | Ala | Asn | Asp | Asn<br>240 |
| Ala | Pro | Val | Phe | Asn<br>245 | Gln | Ser | Leu | Tyr | Arg<br>250 | Ala | Arg | Val | Pro | Gly<br>255 | Gly |
| Cys | Thr | Ser | Gly<br>260 | Thr | Arg | Val | Val | Gln<br>265 | Val | Leu | Ala | Thr | Asp<br>270 | Leu | Asp |
| Glu | Gly | Pro<br>275 | Asn | Gly | Glu | Ile | Ile<br>280 | Tyr | Ser | Phe | Gly | Ser<br>285 | His | Asn | Arg |
| Ala | Gly | Val | Arg | Gln | Leu | Phe | Ala | Leu | Asp | Leu | Val | Thr | Gly | Met | Leu |

-continued

```
              290                    295                    300
Thr Ile Lys Gly Arg Leu Asp Phe Glu Asp Thr Lys Leu His Glu Ile
305                 310                 315                 320
Tyr Ile Gln Ala Lys Asp Lys Gly Ala Asn Pro Glu Gly Ala His Cys
                325                 330                 335
Lys Val Leu Val Glu Val Val Asp Val Asn Asp Asn Ala Pro Glu Ile
                340                 345                 350
Thr Val Thr Ser Val Tyr Ser Pro Val Pro Glu Asp Ala Ser Gly Thr
                355                 360                 365
Val Ile Ala Leu Leu Ser Val Thr Asp Leu Asp Ala Gly Glu Asn Gly
        370                 375                 380
Leu Val Thr Cys Glu Val Pro Pro Gly Leu Pro Phe Ser Leu Thr Ser
385                 390                 395                 400
Ser Leu Lys Asn Tyr Phe Thr Leu Lys Thr Ser Ala Asp Leu Asp Arg
                405                 410                 415
Glu Thr Val Pro Glu Tyr Asn Leu Ser Ile Thr Ala Arg Asp Ala Gly
                420                 425                 430
Thr Pro Ser Leu Ser Ala Leu Thr Ile Val Arg Val Gln Val Ser Asp
            435                 440                 445
Ile Asn Asp Asn Pro Pro Gln Ser Ser Gln Ser Ser Tyr Asp Val Tyr
    450                 455                 460
Ile Glu Glu Asn Asn Leu Pro Gly Ala Pro Ile Leu Asn Leu Ser Val
465                 470                 475                 480
Trp Asp Pro Asp Ala Pro Gln Asn Ala Arg Leu Ser Phe Phe Leu Leu
                485                 490                 495
Glu Gln Gly Ala Glu Thr Gly Leu Val Gly Arg Tyr Phe Thr Ile Asn
                500                 505                 510
Arg Asp Asn Gly Ile Val Ser Ser Leu Val Pro Leu Asp Tyr Glu Asp
            515                 520                 525
Arg Arg Glu Phe Glu Leu Thr Ala His Ile Ser Asp Gly Gly Thr Pro
        530                 535                 540
Val Leu Ala Thr Asn Ile Ser Val Asn Ile Phe Val Thr Asp Arg Asn
545                 550                 555                 560
Asp Asn Ala Pro Gln Val Leu Tyr Pro Arg Pro Gly Gly Ser Ser Val
                565                 570                 575
Glu Met Leu Pro Arg Gly Thr Ser Ala Gly His Leu Val Ser Arg Val
                580                 585                 590
Val Gly Trp Asp Ala Asp Ala Gly His Asn Ala Trp Leu Ser Tyr Ser
        595                 600                 605
Leu Phe Gly Ser Pro Asn Gln Ser Leu Phe Ala Ile Gly Leu His Thr
    610                 615                 620
Gly Gln Ile Ser Thr Ala Arg Pro Val Gln Asp Thr Asp Ser Pro Arg
625                 630                 635                 640
Gln Thr Leu Thr Val Leu Ile Lys Asp Asn Gly Glu Pro Ser Leu Ser
                645                 650                 655
Thr Thr Ala Thr Leu Thr Val Ser Val Thr Glu Asp Ser Pro Glu Ala
                660                 665                 670
Arg Ala Glu Phe Pro Ser Gly Ser Ala Pro Arg Glu Gln Lys Lys Asn
            675                 680                 685
Leu Thr Phe Tyr Leu Leu Leu Ser Leu Ile Leu Val Ser Val Gly Phe
    690                 695                 700
Val Val Thr Val Phe Gly Val Ile Ile Phe Lys Val Tyr Lys Trp Lys
705                 710                 715                 720
```

| | | | | | | | | | | | | | | |
|---|---|---|---|---|---|---|---|---|---|---|---|---|---|---|
|Gln|Ser|Arg|Asp|Leu|Tyr|Arg|Ala|Pro|Val|Ser|Ser|Leu|Tyr|Arg|Thr|
| | | | |725| | | |730| | | | |735| |
|Pro|Gly|Pro|Ser|Leu|His|Ala|Asp|Ala|Val|Arg|Gly|Gly|Leu|Met|Ser|
| | | |740| | | |745| | | | |750| | |
|Pro|His|Leu|Tyr|His|Gln|Val|Tyr|Leu|Thr|Thr|Asp|Ser|Arg|Arg|Ser|
| | |755| | | |760| | | |765| | | | |
|Asp|Pro|Leu|Leu|Lys|Lys|Pro|Gly|Ala|Ala|Ser|Pro|Leu|Ala|Ser|Arg|
| |770| | | |775| | | | |780| | | | |
|Gln|Asn|Thr|Leu|Arg|Ser|Cys|Asp|Pro|Val|Phe|Tyr|Arg|Gln|Val|Leu|
|785| | | |790| | | |795| | | | | |800|
|Gly|Ala|Glu|Ser|Ala|Pro|Pro|Gly|Gln|Val|Arg|Phe|Ser|Lys|Ser|Cys|
| | | |805| | | |810| | | | |815| | |
|Leu|Thr|Leu|Leu|Val|Pro|Phe|Tyr|Ser|Tyr|Ile|Ile|Leu|Arg|Arg|Leu|
| | |820| | | | |825| | | | |830| | |
|Glu|Leu|Phe|Phe| | | | | | | | | | | | |
| | |835| | | | | | | | | | | | | |

( 2 ) INFORMATION FOR SEQ ID NO:106:

( i ) SEQUENCE CHARACTERISTICS:
    ( A ) LENGTH: 2751 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 115..2160

( x i ) SEQUENCE DESCRIPTION: SEQ ID NO:106:

```
CGAAAGCCAT GTCGGACTCG TCGCCCAGCG CCCAAGCGCT AACCCGCTGA AAGTTTCTCA           60

GCGAAATCTC AGGGACGATC TGGACCCCGC TGAGAGGAAC TGCTTTTGAG TGAG ATG          117
                                                            Met
                                                             1

GTC CCA GAG GCC TGG AGG AGC GGA CTG GTA AGC ACC GGG AGG GTA GTG           165
Val Pro Glu Ala Trp Arg Ser Gly Leu Val Ser Thr Gly Arg Val Val
          5                   10                  15

GGA GTT TTG CTT CTG CTT GGT GCC TTG AAC AAG GCT TCC ACG TCA ATT           213
Gly Val Leu Leu Leu Leu Gly Ala Leu Asn Lys Ala Ser Thr Val Ile
     20                  25                  30

CAC TAT GAG ATC CCG GAG GAA AGA GAG AAG GGT TTC GCT GTG GGC AAC           261
His Tyr Glu Ile Pro Glu Glu Arg Glu Lys Gly Phe Ala Val Gly Asn
 35                  40                  45

GTG GTC GCG AAC CTT GGT TTG GAT CTC GGT AGC CTC TCA GCC CGC AGG           309
Val Val Ala Asn Leu Gly Leu Asp Leu Gly Ser Leu Ser Ala Arg Arg
 50                  55                  60                  65

TTC CCG GTG GTG TCT GGA GCT AGC CGA AGA TTC TTT GAG GTG AAC CGG           357
Phe Pro Val Val Ser Gly Ala Ser Arg Arg Phe Phe Glu Val Asn Arg
                 70                  75                  80

GAG ACC GGA GAG ATG TTT GTG AAC GAC CGT CTG GAT CGA GAG GAG CTG           405
Glu Thr Gly Glu Met Phe Val Asn Asp Arg Leu Asp Arg Glu Glu Leu
             85                  90                  95

TGT GGG ACA CTG CCC TCT TGC ACT GTA ACT CTG GAG TTG GTA GTG GAG           453
Cys Gly Thr Leu Pro Ser Cys Thr Val Thr Leu Glu Leu Val Val Glu
        100                 105                 110

AAC CCG CTG GAG CTG TTC AGC GTG GAA GTG GTG ATC CAG GAC ATC AAC           501
Asn Pro Leu Glu Leu Phe Ser Val Glu Val Val Ile Gln Asp Ile Asn
    115                 120                 125

GAC AAC AAT CCT GCT TTC CCT ACC CAG GAA ATG AAA TTG GAG ATT AGC           549
```

```
Asp Asn Asn Pro Ala Phe Pro Thr Gln Glu Met Lys Leu Glu Ile Ser
130             135             140             145

GAG GCC GTG GCT CCG GGG ACG CGC TTT CCG CTC GAG AGC GCG CAC GAT    597
Glu Ala Val Ala Pro Gly Thr Arg Phe Pro Leu Glu Ser Ala His Asp
            150             155             160

CCC GAT CTG GGA AGC AAC TCT TTA CAA ACC TAT GAG CTG AGC CGA AAT    645
Pro Asp Leu Gly Ser Asn Ser Leu Gln Thr Tyr Glu Leu Ser Arg Asn
            165             170             175

GAA TAC TTT GCG CTT CGC GTG CAG ACG CGG GAG GAC AGC ACC AAG TAC    693
Glu Tyr Phe Ala Leu Arg Val Gln Thr Arg Glu Asp Ser Thr Lys Tyr
        180             185             190

GCG GAG CTG GTG TTG GAG CGC GCC CTG GAC CGA GAA CGG GAG CCT AGT    741
Ala Glu Leu Val Leu Glu Arg Ala Leu Asp Arg Glu Arg Glu Pro Ser
195             200             205

CTC CAG TTA GTG CTG ACG GCG TTG GAC GGA GGG ACC CCA GCT CTC TCC    789
Leu Gln Leu Val Leu Thr Ala Leu Asp Gly Gly Thr Pro Ala Leu Ser
210             215             220             225

GCC AGC CTG CCT ATT CAC ATC AAG GTG CTG GAC GCG AAT GAC AAT GCG    837
Ala Ser Leu Pro Ile His Ile Lys Val Leu Asp Ala Asn Asp Asn Ala
            230             235             240

CCT GTC TTC AAC CAG TCC TTG TAC CGG GCG CGC GTT CCT GGA GGA TGC    885
Pro Val Phe Asn Gln Ser Leu Tyr Arg Ala Arg Val Pro Gly Gly Cys
        245             250             255

ACC TCC GGC ACG CGC GTG GTA CAA GTC CTT GCA ACG GAT CTG GAT GAA    933
Thr Ser Gly Thr Arg Val Val Gln Val Leu Ala Thr Asp Leu Asp Glu
        260             265             270

GGC CCC AAC GGT GAA ATT ATT TAC TCC TTC GGC AGC CAC AAC CGC GCC    981
Gly Pro Asn Gly Glu Ile Ile Tyr Ser Phe Gly Ser His Asn Arg Ala
275             280             285

GGC GTG CGG CAA CTA TTC GCC TTA GAC CTT GTA ACC GGG ATG CTG ACA    1029
Gly Val Arg Gln Leu Phe Ala Leu Asp Leu Val Thr Gly Met Leu Thr
290             295             300             305

ATC AAG GGT CGG CTG GAC TTC GAG GAC ACC AAA CTC CAT GAG ATT TAC    1077
Ile Lys Gly Arg Leu Asp Phe Glu Asp Thr Lys Leu His Glu Ile Tyr
            310             315             320

ATC CAG GCC AAA GAC AAG GGC GCC AAT CCC GAA GGA GCA CAT TGC AAA    1125
Ile Gln Ala Lys Asp Lys Gly Ala Asn Pro Glu Gly Ala His Cys Lys
            325             330             335

GTG TTG GTG GAG GTT GTG GAT GTG AAT GAC AAC GCC CCG GAG ATC ACA    1173
Val Leu Val Glu Val Val Asp Val Asn Asp Asn Ala Pro Glu Ile Thr
        340             345             350

GTC ACC TCC GTG TAC AGC CCA GTA CCC GAG GAT GCC TCT GGG ACT GTC    1221
Val Thr Ser Val Tyr Ser Pro Val Pro Glu Asp Ala Ser Gly Thr Val
        355             360             365

ATC GCT TTG CTC AGT GTG ACT GAC CTG GAT GCT GGC GAG AAC GGG CTG    1269
Ile Ala Leu Leu Ser Val Thr Asp Leu Asp Ala Gly Glu Asn Gly Leu
370             375             380             385

GTG ACC TGC GAA GTT CCA CCG GGT CTC CCT TTC AGC CTT ACT TCT TCC    1317
Val Thr Cys Glu Val Pro Pro Gly Leu Pro Phe Ser Leu Thr Ser Ser
            390             395             400

CTC AAG AAT TAC TTC ACT TTG AAA ACC AGT GCA GAC CTG GAT CGG GAG    1365
Leu Lys Asn Tyr Phe Thr Leu Lys Thr Ser Ala Asp Leu Asp Arg Glu
            405             410             415

ACT GTG CCA GAA TAC AAC CTC AGC ATC ACC GCC CGA GAC GCC GGA ACC    1413
Thr Val Pro Glu Tyr Asn Leu Ser Ile Thr Ala Arg Asp Ala Gly Thr
        420             425             430

CCT TCC CTC TCA GCC CTT ACA ATA GTG CGT GTT CAA GTG TCC GAC ATC    1461
Pro Ser Leu Ser Ala Leu Thr Ile Val Arg Val Gln Val Ser Asp Ile
435             440             445

AAT GAC AAC CCT CCA CAA TCT TCT CAA TCT TCC TAC GAC GTT TAC ATT    1509
```

```
Asn Asp Asn Pro Pro Gln Ser Ser Gln Ser Ser Tyr Asp Val Tyr Ile
450                 455                 460                 465

GAA GAA AAC AAC CTC CCC GGG GCT CCA ATA CTA AAC CTA AGT GTC TGG          1557
Glu Glu Asn Asn Leu Pro Gly Ala Pro Ile Leu Asn Leu Ser Val Trp
                470                 475                 480

GAC CCC GAC GCC CCG CAG AAT GCT CGG CTT TCT TTC TTT CTC TTG GAG          1605
Asp Pro Asp Ala Pro Gln Asn Ala Arg Leu Ser Phe Phe Leu Leu Glu
            485                 490                 495

CAA GGA GCT GAA ACC GGG CTA GTG GGT CGC TAT TTC ACA ATA AAT CGT          1653
Gln Gly Ala Glu Thr Gly Leu Val Gly Arg Tyr Phe Thr Ile Asn Arg
        500                 505                 510

GAC AAT GGC ATA GTG TCA TCC TTA GTG CCC CTA GAC TAT GAG GAT CGG          1701
Asp Asn Gly Ile Val Ser Ser Leu Val Pro Leu Asp Tyr Glu Asp Arg
    515                 520                 525

CGG GAA TTT GAA TTA ACA GCT CAT ATC AGC GAT GGG GGC ACC CCG GTC          1749
Arg Glu Phe Glu Leu Thr Ala His Ile Ser Asp Gly Gly Thr Pro Val
530                 535                 540                 545

CTA GCC ACC AAC ATC AGC GTG AAC ATA TTT GTC ACT GAT CGC AAT GAC          1797
Leu Ala Thr Asn Ile Ser Val Asn Ile Phe Val Thr Asp Arg Asn Asp
                550                 555                 560

AAT GCC CCC CAG GTC CTA TAT CCT CGG CCA GGT GGG AGC TCG GTG GAG          1845
Asn Ala Pro Gln Val Leu Tyr Pro Arg Pro Gly Gly Ser Ser Val Glu
            565                 570                 575

ATG CTG CCT CGA GGT ACC TCA GCT GGC CAC CTA GTG TCA CGG GTG GTA          1893
Met Leu Pro Arg Gly Thr Ser Ala Gly His Leu Val Ser Arg Val Val
        580                 585                 590

GGC TGG GAC GCG GAT GCA GGG CAC AAT GCC TGG CTC TCC TAC AGT CTC          1941
Gly Trp Asp Ala Asp Ala Gly His Asn Ala Trp Leu Ser Tyr Ser Leu
    595                 600                 605

TTT GGA TCC CCT AAC CAG AGC CTT TTT GCC ATA GGG CTG CAC ACT GGT          1989
Phe Gly Ser Pro Asn Gln Ser Leu Phe Ala Ile Gly Leu His Thr Gly
610                 615                 620                 625

CAA ATC AGT ACT GCC CGT CCA GTC CAA GAC ACA GAT TCA CCC AGG CAG          2037
Gln Ile Ser Thr Ala Arg Pro Val Gln Asp Thr Asp Ser Pro Arg Gln
                630                 635                 640

ACT CTC ACT GTC TTG ATC AAA GAC AAT GGG GAG CCT TCG CTC TCC ACC          2085
Thr Leu Thr Val Leu Ile Lys Asp Asn Gly Glu Pro Ser Leu Ser Thr
            645                 650                 655

ACT GCT ACC CTC ACT GTG TCA GTA ACC GAG GAC TCT CCT GAA GCC CGA          2133
Thr Ala Thr Leu Thr Val Ser Val Thr Glu Asp Ser Pro Glu Ala Arg
        660                 665                 670

GCC GAG TTC CCC TCT GGC TCT GCC AGT TAAACCTTCT TTAATTATGG                2180
Ala Glu Phe Pro Ser Gly Ser Ala Ser
    675                 680

ATTAGCCATT AACATTTTTG AAACGTGGAC CATTTAACCT CGGCCTACCC CCTCCAACTG        2240

TCCTGGTGAT GAGTTCATTA GCTAAGTTAA ATTAATTGAA CTTTGATCTA AACCAAAACA        2300

AATCAGGAAA ATAAAGCTGT AAAGGAACTT ATCAAGCATT CCAAAACCAA CTAGAAATTA        2360

CTTGAAGTTT CGAGTGAGCA TTGCCTGTGC CAGTATTCTT CATTATAGGA TTATAAACTC        2420

GTTTTTTTCC CAAAGCGCAT GTCTACGCCA GGCAGAGGAG TAATTATTCA GCCAATTTCA        2480

TGGATGTAAC GATGGATATA AATAATTGAT AGCACCTAGA GGCTTCCAGT TTGGGTGGAA        2540

GGCTAAAAGT AGAGGGGAAC TCACTCACTT GAGAAATGAT ATTTAAGTGA ATAAATAGTT        2600

CTCTTCTATG AAACTATTAC TATTTAGTTC TCTGGAAAAC TTAAGTGTAT TAATGATTAG        2660

AACATCAAAT CCTAAGTAAA GAAATGACAT TTTAAATATA AAAGCCAAA CTTTAAATAA         2720

ATCATAGAGA CCTCAGACAT AATATAGGAA A                                       2751
```

( 2 ) INFORMATION FOR SEQ ID NO:107:

( i ) SEQUENCE CHARACTERISTICS:
        ( A ) LENGTH: 682 amino acids
        ( B ) TYPE: amino acid
        ( D ) TOPOLOGY: linear ( i i ) MOLECULE TYPE: protein ( x i ) SEQUENCE DESCRIPTION: SEQ ID NO:107:

```
Met Val Pro Glu Ala Trp Arg Ser Gly Leu Val Ser Thr Gly Arg Val
 1               5                  10                  15

Val Gly Val Leu Leu Leu Leu Gly Ala Leu Asn Lys Ala Ser Thr Val
                20                  25                  30

Ile His Tyr Glu Ile Pro Glu Glu Arg Glu Lys Gly Phe Ala Val Gly
            35                  40                  45

Asn Val Val Ala Asn Leu Gly Leu Asp Leu Gly Ser Leu Ser Ala Arg
        50                  55                  60

Arg Phe Pro Val Val Ser Gly Ala Ser Arg Arg Phe Phe Glu Val Asn
 65                  70                  75                  80

Arg Glu Thr Gly Glu Met Phe Val Asn Asp Arg Leu Asp Arg Glu Glu
                85                  90                  95

Leu Cys Gly Thr Leu Pro Ser Cys Thr Val Thr Leu Glu Leu Val Val
                100                 105                 110

Glu Asn Pro Leu Glu Leu Phe Ser Val Glu Val Val Ile Gln Asp Ile
            115                 120                 125

Asn Asp Asn Asn Pro Ala Phe Pro Thr Gln Glu Met Lys Leu Glu Ile
        130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
            180                 185                 190

Tyr Ala Glu Leu Val Leu Glu Arg Ala Leu Asp Arg Glu Arg Glu Pro
        195                 200                 205

Ser Leu Gln Leu Val Leu Thr Ala Leu Asp Gly Gly Thr Pro Ala Leu
210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
            260                 265                 270

Glu Gly Pro Asn Gly Glu Ile Ile Tyr Ser Phe Gly Ser His Asn Arg
        275                 280                 285

Ala Gly Val Arg Gln Leu Phe Ala Leu Asp Leu Val Thr Gly Met Leu
290                 295                 300

Thr Ile Lys Gly Arg Leu Asp Phe Glu Asp Thr Lys Leu His Glu Ile
305                 310                 315                 320

Tyr Ile Gln Ala Lys Asp Lys Gly Ala Asn Pro Glu Gly Ala His Cys
                325                 330                 335

Lys Val Leu Val Glu Val Val Asp Val Asn Asp Asn Ala Pro Glu Ile
            340                 345                 350

Thr Val Thr Ser Val Tyr Ser Pro Val Pro Glu Asp Ala Ser Gly Thr
        355                 360                 365
```

| | | | | | | | | | | | | | | |
|---|---|---|---|---|---|---|---|---|---|---|---|---|---|---|
| Val | Ile | Ala | Leu | Leu | Ser | Val | Thr | Asp | Leu | Asp | Ala | Gly | Glu | Asn | Gly |
| | 370 | | | | | 375 | | | | 380 | | | | |
| Leu | Val | Thr | Cys | Glu | Val | Pro | Pro | Gly | Leu | Pro | Phe | Ser | Leu | Thr | Ser |
| 385 | | | | | 390 | | | | | 395 | | | | | 400 |
| Ser | Leu | Lys | Asn | Tyr | Phe | Thr | Leu | Lys | Thr | Ser | Ala | Asp | Leu | Asp | Arg |
| | | | | 405 | | | | | 410 | | | | | 415 | |
| Glu | Thr | Val | Pro | Glu | Tyr | Asn | Leu | Ser | Ile | Thr | Ala | Arg | Asp | Ala | Gly |
| | | | 420 | | | | | 425 | | | | | 430 | | |
| Thr | Pro | Ser | Leu | Ser | Ala | Leu | Thr | Ile | Val | Arg | Val | Gln | Val | Ser | Asp |
| | | 435 | | | | | 440 | | | | | 445 | | | |
| Ile | Asn | Asp | Asn | Pro | Pro | Gln | Ser | Ser | Gln | Ser | Ser | Tyr | Asp | Val | Tyr |
| | 450 | | | | | 455 | | | | | 460 | | | | |
| Ile | Glu | Glu | Asn | Asn | Leu | Pro | Gly | Ala | Pro | Ile | Leu | Asn | Leu | Ser | Val |
| 465 | | | | | 470 | | | | | 475 | | | | | 480 |
| Trp | Asp | Pro | Asp | Ala | Pro | Gln | Asn | Ala | Arg | Leu | Ser | Phe | Phe | Leu | Leu |
| | | | | 485 | | | | | 490 | | | | | 495 | |
| Glu | Gln | Gly | Ala | Glu | Thr | Gly | Leu | Val | Gly | Arg | Tyr | Phe | Thr | Ile | Asn |
| | | | 500 | | | | | 505 | | | | | 510 | | |
| Arg | Asp | Asn | Gly | Ile | Val | Ser | Ser | Leu | Val | Pro | Leu | Asp | Tyr | Glu | Asp |
| | | 515 | | | | | 520 | | | | | 525 | | | |
| Arg | Arg | Glu | Phe | Glu | Leu | Thr | Ala | His | Ile | Ser | Asp | Gly | Gly | Thr | Pro |
| | 530 | | | | | 535 | | | | | 540 | | | | |
| Val | Leu | Ala | Thr | Asn | Ile | Ser | Val | Asn | Ile | Phe | Val | Thr | Asp | Arg | Asn |
| 545 | | | | | 550 | | | | | 555 | | | | | 560 |
| Asp | Asn | Ala | Pro | Gln | Val | Leu | Tyr | Pro | Arg | Pro | Gly | Gly | Ser | Ser | Val |
| | | | | 565 | | | | | 570 | | | | | 575 | |
| Glu | Met | Leu | Pro | Arg | Gly | Thr | Ser | Ala | Gly | His | Leu | Val | Ser | Arg | Val |
| | | | 580 | | | | | 585 | | | | | 590 | | |
| Val | Gly | Trp | Asp | Ala | Asp | Ala | Gly | His | Asn | Ala | Trp | Leu | Ser | Tyr | Ser |
| | | 595 | | | | | 600 | | | | | 605 | | | |
| Leu | Phe | Gly | Ser | Pro | Asn | Gln | Ser | Leu | Phe | Ala | Ile | Gly | Leu | His | Thr |
| | 610 | | | | | 615 | | | | | 620 | | | | |
| Gly | Gln | Ile | Ser | Thr | Ala | Arg | Pro | Val | Gln | Asp | Thr | Asp | Ser | Pro | Arg |
| 625 | | | | | 630 | | | | | 635 | | | | | 640 |
| Gln | Thr | Leu | Thr | Val | Leu | Ile | Lys | Asp | Asn | Gly | Glu | Pro | Ser | Leu | Ser |
| | | | | 645 | | | | | 650 | | | | | 655 | |
| Thr | Thr | Ala | Thr | Leu | Thr | Val | Ser | Val | Thr | Glu | Asp | Ser | Pro | Glu | Ala |
| | | | 660 | | | | | 665 | | | | | 670 | | |
| Arg | Ala | Glu | Phe | Pro | Ser | Gly | Ser | Ala | Ser | | | | | | |
| | | 675 | | | | | 680 | | | | | | | | |

( 2 ) INFORMATION FOR SEQ ID NO:108:

( i ) SEQUENCE CHARACTERISTICS:
    ( A ) LENGTH: 2831 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:108:

```
GAATTCGGCA CGAGGCTGAA CTGAGGGTGA CGGACATAAA CGACTATTCT CCAGTGTTCA    60

GTGAAAGAGA AATGATACTG AGGATACCAG AAAACAGTGC TCGGGGAAAT ACATTCCCTT   120

TAAACAATGC TCTGGACTCA GACGTAGATA TCAACAATAT CCAGACCTAT AGGCTCAGCT   180

CAAACTCTCA TTTCCTGGTT GTAACCCGCA ACCGCAGTGA TGGCAGGAAG TACCCAGAGC   240
```

| | | | | | | |
|---|---|---|---|---|---|---|
| TGGTGCTGGA | GAAAGAACTG | GATCGAGAGG | AGGAACCTGA | GCTGAGGTTA | ACGCTGACAG | 300 |
| CTTTGGATGG | TGGCTCTCCT | CCCCGGTCTG | GGACGACACA | GGTCCTCATT | GAAGTAGTGG | 360 |
| ACACCAACGA | TAATGCACCC | GAGTTTCAGC | AGCCAACATA | CCAAGTGCAA | ACTCCCGAGA | 420 |
| ACAGTCCCAC | CGGCTCTCTG | GTACTCACAG | TCTCAGCCAA | TGACTTAGAC | AGTGGAGACT | 480 |
| ATGGGAAAGT | CTTGTACGCA | CTTTCGCAAC | CCTCAGAAGA | TATTAGCAAA | ACATTCGAGG | 540 |
| TAAACCCTGT | AACCGGGGAA | ATTCGCCTAC | GAAAGAGGT | GAATTTTGAA | ACTATTCCTT | 600 |
| CGTATGAAGT | GGTTATCAAG | GGACGGACG | GGGAGGTCT | CTCAGGAAAA | TGCACTCTGT | 660 |
| TACTGCAGGT | GGTGGACGTG | AATGACAATG | CCCCAGAAGT | GATGCTATCT | GCGCTAACCA | 720 |
| ACCCAGTCCC | AGAAAATTCC | CCCGATGAGG | TAGTGGCTGT | TTTCAGTGTT | AGAGATCCTG | 780 |
| ACTCTGGGAA | CAACGGAAAA | GTGATTGCAT | CCATCGAGGA | AGACCTGCCC | TTTCTTCTAA | 840 |
| AATCTTCAGG | AAAGAACTTT | TACACTTTAG | TAACCAAGGG | AGCACTTGAC | AGGGAAGAAA | 900 |
| GAGAGCAATT | GAACATCACC | ATCACAGTCA | CTGACCTGGG | CATACCCAGG | CTCACCACCC | 960 |
| AACACACCAT | AACAGTGCAG | GTGGCAGACA | TCAACGACAA | TGCCCCCTCC | TTCACCCAAA | 1020 |
| CCTCCTACAC | CATGTTTGTC | CGCGAGAACA | ACAGCCCCGC | CCTGCACATA | GGCACCATCA | 1080 |
| GCGCCACAGA | CTCAGACTCA | GGATCCAATG | CCCACATCAC | CTACTCGCTG | CTACCGCCCC | 1140 |
| AAGACCCACA | GCTGGCCCTC | GACTCGCTCA | TCTCCATCAA | TGTAGACAAC | GGGCAGCTGT | 1200 |
| TCGCGCTCAG | GGCGCTAGAC | TATGAGGCTC | TGCAGGGCTT | CGAGTTCCAT | GTGGGCGCCA | 1260 |
| CAGACCAAGG | CTCGCCCGCG | CTCAGCAGCC | AGGCTCTGGT | GCACGTGGTG | GTGTTGGACG | 1320 |
| ACAATGACAA | TGCGCCCTTC | GTGCTCTACC | CGCTGCAAAA | CGCCTCTGCA | CCCTTCACTG | 1380 |
| AGCTGCTGCC | CAGGGCGGCA | GAGCCTGGAT | ACCTGGTTAC | CAAGGTGGTA | GCTGTGGACC | 1440 |
| GCGACTCTGG | CCAGAATGCC | TGGCTGTCAT | TCCAGCTGCT | CAAGGCCACG | GAGCCCGGGC | 1500 |
| TGTTCAACGT | ATGGGCGCAC | AATGGCGAGG | TACGCACCTC | CAGGCTGCTG | AGCGAGCGCG | 1560 |
| ACGCACCCAA | GCACAAGCTG | CTGCTGTTGG | TCAAGGACAA | TGGAGATCCT | CCACGCTCTG | 1620 |
| CCAGTGTTAC | TCTGCACGTG | CTAGTGGTGG | ATGCCTTCTC | TCAGCCCTAC | CTGCCTCTGC | 1680 |
| CAGAGGTGGC | GCACGACCCT | GCACAAGAAG | AAGATGCGCT | AACACTCTAC | CTGGTCATAG | 1740 |
| CTTTGGCATC | TGTGTCTTCT | CTCTTCCTCT | TGTCTGTGCT | GCTGTTCGTG | GGGGTGAGGC | 1800 |
| TCTGCAGGAG | GGCCAGGGCA | GCCTCTCTGA | GTGCCTATTC | TGTGCCTGAA | GGCCACTTTC | 1860 |
| CTGGCCAGCT | GGTGGATGTC | AGAGGTATGG | GGACCCTGTC | CCAGAGCTAC | CAGTATGATG | 1920 |
| TATGTCTGAT | GGGGGATTCT | TCTGGGACCA | GCGAATTTAA | CTTCTTAAAG | CCAGTTCTGC | 1980 |
| CTAGCTCTCT | GCACCAGTGC | TCTGGGAAAG | AAATAGAGGA | AAATTCCACA | CTCCAGAATA | 2040 |
| GTTTTGGGTT | TCATCATTAA | TAGAAAACTA | CTTTACAGAT | ATTTAATTCC | AAATATCATC | 2100 |
| TTGTTGATTA | ACTAAAGTCT | GTTCACATGT | AGCTAGCTAG | CAACGATTTT | AATGTTCACT | 2160 |
| TTACCCATCT | TTTTTCAGGG | TCATGTCTAA | AGCTACAAGT | TTGNCTTTAC | TTATACTTGT | 2220 |
| CGCACAGAAT | NNNNNNNNNN | TGGTGTATAA | GTCACAGTCA | TGGGATACTG | GCACAAGATG | 2280 |
| GCAGCTTGAT | TGCTCAGTTA | TGGCTGCAAA | GGGGNGCTTG | AGTTTAGGGA | ATGTGTTAGA | 2340 |
| GCTGGAATAA | GTTTTCTGAG | AAATGTGTAA | GACAAATTTC | TTTTGCACAT | TCCTGTGTT | 2400 |
| CCTGTACCCC | TGTTTCCAGA | ACTACGAAAT | GTGTCATCAG | AAGGCATGCT | CACATTTTCC | 2460 |
| CCTTTGTTTG | CGTGACCCGG | GTGCCAGAAA | TTAAATAAAA | TTAGCATGGA | GTTCAATGCA | 2520 |
| GCATTAAAAC | AAAGTTACTT | CTACAAACCT | TTTATTCGAC | GGTTAAAATT | GTAACTTCCC | 2580 |
| CACCCATGAG | GCTGGCTGTA | AGAACCAGTA | TGAATGGGTG | TCTATCGCAA | CCTTATTTTC | 2640 |

-continued

| | | | | | |
|---|---|---|---|---|---|
| AAAAATCAAA | CAAAAGGAGA | AATGAGAGAC | CAAACAACAC | GCTACAGGAA | AGATTTCATA | 2700
| AGGATGTATG | TATGGACACA | AAAACTGGGA | TACAGACATT | TTAAATCTGT | TGGTACCACA | 2760
| TGGTGGCGCT | GCAGGCTAAA | GAAATGCAAG | GGAAATTAAA | AAGAGGCTGA | GCTAGAAGTC | 2820
| AAAAAAAAAA | A | | | | | 2831

( 2 ) INFORMATION FOR SEQ ID NO:109:

( i ) SEQUENCE CHARACTERISTICS:
        ( A ) LENGTH: 3353 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 763..3123

( x i ) SEQUENCE DESCRIPTION: SEQ ID NO:109:

| | | | | | |
|---|---|---|---|---|---|
| GTATTTTCC | ACAGTTTAAA | ATTTTCATAA | AATCATAACT | CTCTGACTTT | ATGTAGAAAG | 60
| GATACCACAC | TGGAATTAAC | GTGTAGCTTT | TTCTTGATGT | AATCCAACCA | ATGGGAGCAC | 120
| AATTCTGGTA | CATAGGCTGT | CTAGAATTTG | AAAGAATTA | AAGAATTCAT | TTTGTTTTGC | 180
| TGATAAATTT | TTAAGAAATC | ACGTGGCTTT | ATGTTATTAT | TATTACAAGA | TGACTGATCA | 240
| CTATTATGTC | TTCTTTCACT | TCTCAATTTC | CCTCAGAACA | CTACACCCAG | ACTACAGGCT | 300
| CTGGAGGGTG | GGGACCATGT | CTGGGTTGTT | TACTGATGTA | TTTCATAATT | TGGCACATAG | 360
| AGACCAATAA | TACTCCTTTA | AATGAAGAAA | TTAATAATTA | CCATTGCGTG | ATATTGTGAT | 420
| TACATCATTT | CCTCCCAATT | TCCAAACTCC | TAATAGAATA | GAGAATAGAT | CAATTGTAGC | 480
| AATTCGTTTC | GAAGCAAAGA | CAACGCATGG | TGGCGCTGCA | GGCTAAGGCT | TCAAAAAAG | 540
| GAAAGGAAA | AAGCCCATGA | AATGCTACTA | GCTACTTCAG | ACCTCTTTCA | GCCTAAGAGG | 600
| AAAGCCTGTT | AGCAGAGCAC | GGACCAGTGT | CTCCGGAGAA | TGCTATTCTC | CTACATTTCC | 660
| GAACAGGTTA | TCAACGCACA | GATCGATCAC | TGCCTCTGTC | CCATCGCTCC | CTGAAGTAGC | 720
| TCTGACTCCG | GTTCCTTGAA | AGGGGCGTGT | ACAGAAGTAA | AG ATG GAG | CCT GCA | 774

Met Glu Pro Ala
                                                                                                                  1

| | | | | | | | | | | | | | | | |
|---|---|---|---|---|---|---|---|---|---|---|---|---|---|---|---|
| GGG | GAG | CGC | TTT | CCC | GAA | CAA | AGG | CAA | GTC | CTG | ATT | CTC | CTT | CTT | TTA | 822
| Gly | Glu | Arg | Phe | Pro | Glu | Gln | Arg | Gln | Val | Leu | Ile | Leu | Leu | Leu | Leu | 
| 5 | | | | 10 | | | | | 15 | | | | | | 20 |
| CTG | GAA | GTG | ACT | CTG | GCA | GGC | TGG | GAA | CCC | CGT | CGC | TAT | TCT | GTG | ATG | 870
| Leu | Glu | Val | Thr | Leu | Ala | Gly | Trp | Glu | Pro | Arg | Arg | Tyr | Ser | Val | Met |
| | | | 25 | | | | | 30 | | | | | 35 | | |
| GAG | GAA | ACA | GAG | AGA | GGT | TCT | TTT | GTA | GCC | AAC | CTG | GCC | AAT | GAC | CTA | 918
| Glu | Glu | Thr | Glu | Arg | Gly | Ser | Phe | Val | Ala | Asn | Leu | Ala | Asn | Asp | Leu |
| | | | 40 | | | | 45 | | | | | 50 | | | |
| GGG | CTG | GGA | GTG | GGG | GAG | CTA | GCC | GAG | CGG | GGA | GCC | CGG | GTA | GTT | TCT | 966
| Gly | Leu | Gly | Val | Gly | Glu | Leu | Ala | Glu | Arg | Gly | Ala | Arg | Val | Val | Ser |
| | | 55 | | | | 60 | | | | 65 | | | | | |
| GAG | GAT | AAC | GAA | CAA | GGC | TTG | CAG | CTT | GAT | CTG | CAG | ACC | GGG | CAG | TTG | 1014
| Glu | Asp | Asn | Glu | Gln | Gly | Leu | Gln | Leu | Asp | Leu | Gln | Thr | Gly | Gln | Leu |
| | 70 | | | | 75 | | | | | 80 | | | | | |
| ATA | TTA | AAT | GAG | AAG | CTG | GAC | CGG | GAG | AAG | CTG | TGT | GGC | CCT | ACT | GAG | 1062
| Ile | Leu | Asn | Glu | Lys | Leu | Asp | Arg | Glu | Lys | Leu | Cys | Gly | Pro | Thr | Glu |
| 85 | | | | 90 | | | | | 95 | | | | | 100 | |
| CCC | TGT | ATA | ATG | CAT | TTC | CAA | GTG | TTA | CTG | AAA | AAA | CCT | TTG | GAA | GTA | 1110
| Pro | Cys | Ile | Met | His | Phe | Gln | Val | Leu | Leu | Lys | Lys | Pro | Leu | Glu | Val |

-continued

|     |     |     | 105 |     |     |     |     | 110 |     |     |     |     | 115 |     |     |      |
|-----|-----|-----|-----|-----|-----|-----|-----|-----|-----|-----|-----|-----|-----|-----|-----|------|
| TTT | CGA | GCT | GAA | CTA | CTA | GTG | ACA | GAC | ATA | AAC | GAT | CAT | TCT | CCT | GAG | 1158 |
| Phe | Arg | Ala | Glu | Leu | Leu | Val | Thr | Asp | Ile | Asn | Asp | His | Ser | Pro | Glu |      |
|     |     |     | 120 |     |     |     |     | 125 |     |     |     |     | 130 |     |     |      |
| TTT | CCT | GAA | AGA | GAA | ATG | ACC | CTG | AAA | ATC | CCA | GAA | ACT | AGC | TCC | CTT | 1206 |
| Phe | Pro | Glu | Arg | Glu | Met | Thr | Leu | Lys | Ile | Pro | Glu | Thr | Ser | Ser | Leu |      |
|     |     | 135 |     |     |     |     | 140 |     |     |     |     | 145 |     |     |     |      |
| GGG | ACT | GTG | TTT | CCT | CTG | AAA | AAA | GCT | CGG | GAC | TTG | GAC | GTG | GGC | AGC | 1254 |
| Gly | Thr | Val | Phe | Pro | Leu | Lys | Lys | Ala | Arg | Asp | Leu | Asp | Val | Gly | Ser |      |
|     | 150 |     |     |     |     | 155 |     |     |     |     | 160 |     |     |     |     |      |
| AAT | AAT | GTT | CAA | AAC | TAC | AAT | ATT | TCT | CCC | AAT | TCT | CAT | TTC | CAT | GTT | 1302 |
| Asn | Asn | Val | Gln | Asn | Tyr | Asn | Ile | Ser | Pro | Asn | Ser | His | Phe | His | Val |      |
| 165 |     |     |     |     | 170 |     |     |     |     | 175 |     |     |     |     | 180 |      |
| TCC | ACT | CGC | ACC | CGA | GGG | GAT | GGC | AGG | AAA | TAC | CCA | GAG | CTG | GTG | CTG | 1350 |
| Ser | Thr | Arg | Thr | Arg | Gly | Asp | Gly | Arg | Lys | Tyr | Pro | Glu | Leu | Val | Leu |      |
|     |     |     |     | 185 |     |     |     |     | 190 |     |     |     |     | 195 |     |      |
| GAC | ACA | GAA | CTG | GAT | CGC | GAG | GAG | CAG | GCC | GAG | CTC | AGA | TTA | ACC | TTG | 1398 |
| Asp | Thr | Glu | Leu | Asp | Arg | Glu | Glu | Gln | Ala | Glu | Leu | Arg | Leu | Thr | Leu |      |
|     |     |     | 200 |     |     |     |     | 205 |     |     |     |     | 210 |     |     |      |
| ACA | GCG | GTG | GAC | GGT | GGC | TCT | CCA | CCC | CGA | TCT | GGC | ACC | GTC | CAG | ATC | 1446 |
| Thr | Ala | Val | Asp | Gly | Gly | Ser | Pro | Pro | Arg | Ser | Gly | Thr | Val | Gln | Ile |      |
|     |     | 215 |     |     |     |     | 220 |     |     |     |     | 225 |     |     |     |      |
| CTC | ATC | TTG | GTC | TTG | GAC | GCC | AAT | GAC | AAT | GCC | CCG | GAG | TTT | GTG | CAG | 1494 |
| Leu | Ile | Leu | Val | Leu | Asp | Ala | Asn | Asp | Asn | Ala | Pro | Glu | Phe | Val | Gln |      |
|     | 230 |     |     |     |     | 235 |     |     |     |     | 240 |     |     |     |     |      |
| GCG | CTC | TAC | GAG | GTG | CAG | GTC | CCA | GAG | AAC | AGC | CCA | GTA | GGC | TCC | CTA | 1542 |
| Ala | Leu | Tyr | Glu | Val | Gln | Val | Pro | Glu | Asn | Ser | Pro | Val | Gly | Ser | Leu |      |
| 245 |     |     |     |     | 250 |     |     |     |     | 255 |     |     |     |     | 260 |      |
| GTT | GTC | AAG | GTC | TCT | GCT | AGG | GAT | TTA | GAC | ACT | GGG | ACA | AAT | GGA | GAG | 1590 |
| Val | Val | Lys | Val | Ser | Ala | Arg | Asp | Leu | Asp | Thr | Gly | Thr | Asn | Gly | Glu |      |
|     |     |     |     | 265 |     |     |     |     | 270 |     |     |     |     | 275 |     |      |
| ATA | TCA | TAC | TCC | CTT | TAT | TAC | AGC | TCT | CAG | GAG | ATA | GAC | AAA | CCT | TTT | 1638 |
| Ile | Ser | Tyr | Ser | Leu | Tyr | Tyr | Ser | Ser | Gln | Glu | Ile | Asp | Lys | Pro | Phe |      |
|     |     |     | 280 |     |     |     |     | 285 |     |     |     |     | 290 |     |     |      |
| GAG | CTA | AGC | AGC | CTT | TCA | GGA | GAA | ATT | CGA | CTA | ATT | AAA | AAA | CTA | GAT | 1686 |
| Glu | Leu | Ser | Ser | Leu | Ser | Gly | Glu | Ile | Arg | Leu | Ile | Lys | Lys | Leu | Asp |      |
|     |     | 295 |     |     |     |     | 300 |     |     |     |     | 305 |     |     |     |      |
| TTT | GAG | ACA | ATG | TCT | TCA | TAT | GAT | CTA | GAT | ATA | GAG | GCA | TCT | GAT | GGC | 1734 |
| Phe | Glu | Thr | Met | Ser | Ser | Tyr | Asp | Leu | Asp | Ile | Glu | Ala | Ser | Asp | Gly |      |
|     | 310 |     |     |     |     | 315 |     |     |     |     | 320 |     |     |     |     |      |
| GGG | GGA | CTT | TCT | GGA | AAA | TGC | TCT | GTC | TCT | GTT | AAG | GTG | CTG | GAT | GTT | 1782 |
| Gly | Gly | Leu | Ser | Gly | Lys | Cys | Ser | Val | Ser | Val | Lys | Val | Leu | Asp | Val |      |
| 325 |     |     |     |     | 330 |     |     |     |     | 335 |     |     |     |     | 340 |      |
| AAC | GAT | AAC | TTC | CCG | GAA | CTA | AGT | ATT | TCA | TCA | CTT | ACC | AGC | CCT | ATT | 1830 |
| Asn | Asp | Asn | Phe | Pro | Glu | Leu | Ser | Ile | Ser | Ser | Leu | Thr | Ser | Pro | Ile |      |
|     |     |     |     | 345 |     |     |     |     | 350 |     |     |     |     | 355 |     |      |
| CCC | GAG | AAT | TCT | CCA | GAG | ACA | GAA | GTG | GCC | CTG | TTT | AGG | ATT | AGA | GAC | 1878 |
| Pro | Glu | Asn | Ser | Pro | Glu | Thr | Glu | Val | Ala | Leu | Phe | Arg | Ile | Arg | Asp |      |
|     |     |     | 360 |     |     |     |     | 365 |     |     |     |     | 370 |     |     |      |
| CGA | GAC | TCT | GGA | GAA | AAT | GGA | AAA | ATG | ATT | TGC | TCA | ATT | CAG | GAT | GAT | 1926 |
| Arg | Asp | Ser | Gly | Glu | Asn | Gly | Lys | Met | Ile | Cys | Ser | Ile | Gln | Asp | Asp |      |
|     |     | 375 |     |     |     |     | 380 |     |     |     |     | 385 |     |     |     |      |
| GTT | CCT | TTT | AAG | CTA | AAA | CCT | TCT | GTT | GAG | AAT | TTC | TAC | AGG | CTG | GTA | 1974 |
| Val | Pro | Phe | Lys | Leu | Lys | Pro | Ser | Val | Glu | Asn | Phe | Tyr | Arg | Leu | Val |      |
|     | 390 |     |     |     |     | 395 |     |     |     |     | 400 |     |     |     |     |      |
| ACA | GAA | GGG | GCG | CTG | GAC | AGA | GAG | ACC | AGA | GCC | GAG | TAC | AAC | ATC | ACC | 2022 |
| Thr | Glu | Gly | Ala | Leu | Asp | Arg | Glu | Thr | Arg | Ala | Glu | Tyr | Asn | Ile | Thr |      |
| 405 |     |     |     |     | 410 |     |     |     |     | 415 |     |     |     |     | 420 |      |
| ATC | ACC | ATC | ACA | GAC | TTG | GGG | ACT | CCA | AGG | CTG | AAA | ACC | GAG | CAG | AGC | 2070 |
| Ile | Thr | Ile | Thr | Asp | Leu | Gly | Thr | Pro | Arg | Leu | Lys | Thr | Glu | Gln | Ser |      |

-continued

|  |  |  | 425 |  |  |  | 430 |  |  |  | 435 |  |  |  |  |
|---|---|---|---|---|---|---|---|---|---|---|---|---|---|---|---|
| ATA | ACC | GTG | CTG | GTG | TCG | GAC | GTC | AAT | GAC | AAC | GCC | CCC | GCC | TTC | ACC | 2118 |
| Ile | Thr | Val | Leu | Val | Ser | Asp | Val | Asn | Asp | Asn | Ala | Pro | Ala | Phe | Thr |  |
|  |  |  | 440 |  |  |  | 445 |  |  |  | 450 |  |  |  |  |
| CAA | ACC | TCC | TAC | ACC | CTG | TTC | GTC | CGC | GAG | AAC | AAC | AGC | CCC | GCC | CTG | 2166 |
| Gln | Thr | Ser | Tyr | Thr | Leu | Phe | Val | Arg | Glu | Asn | Asn | Ser | Pro | Ala | Leu |  |
|  |  | 455 |  |  |  |  | 460 |  |  |  | 465 |  |  |  |  |
| CAC | ATC | GGC | AGT | GTC | AGC | GCC | ACA | GAC | AGA | GAC | TCG | GGC | ACC | AAC | GCC | 2214 |
| His | Ile | Gly | Ser | Val | Ser | Ala | Thr | Asp | Arg | Asp | Ser | Gly | Thr | Asn | Ala |  |
|  | 470 |  |  |  | 475 |  |  |  |  | 480 |  |  |  |  |  |
| CAG | GTC | ACC | TAC | TCG | CTG | CTG | CCG | CCC | CAG | GAC | CCG | CAC | CTG | CCC | CTA | 2262 |
| Gln | Val | Thr | Tyr | Ser | Leu | Leu | Pro | Pro | Gln | Asp | Pro | His | Leu | Pro | Leu |  |
| 485 |  |  |  |  | 490 |  |  |  | 495 |  |  |  |  |  | 500 |  |
| ACC | TCC | CTG | GTC | TCC | ATT | AAC | ACG | GAC | AAC | GGC | CAC | CTG | TTC | GCT | CTC | 2310 |
| Thr | Ser | Leu | Val | Ser | Ile | Asn | Thr | Asp | Asn | Gly | His | Leu | Phe | Ala | Leu |  |
|  |  |  |  | 505 |  |  |  |  | 510 |  |  |  |  | 515 |  |  |
| CAG | TCG | CTG | GAC | TAC | GAG | GCC | CTG | CAG | GCT | TTC | GAG | TTC | CGC | GTG | GGC | 2358 |
| Gln | Ser | Leu | Asp | Tyr | Glu | Ala | Leu | Gln | Ala | Phe | Glu | Phe | Arg | Val | Gly |  |
|  |  |  | 520 |  |  |  |  | 525 |  |  |  |  | 530 |  |  |  |
| GCC | ACA | GAC | CGC | GGC | TTC | CCG | GCG | CTG | AGC | AGC | GAG | GCG | CTG | GTG | CGA | 2406 |
| Ala | Thr | Asp | Arg | Gly | Phe | Pro | Ala | Leu | Ser | Ser | Glu | Ala | Leu | Val | Arg |  |
|  | 535 |  |  |  |  | 540 |  |  |  |  | 545 |  |  |  |  |  |
| GTG | CTG | GTG | CTG | GAC | GCC | AAC | GAC | AAC | TCG | CCC | TTC | GTG | CTG | TAC | CCG | 2454 |
| Val | Leu | Val | Leu | Asp | Ala | Asn | Asp | Asn | Ser | Pro | Phe | Val | Leu | Tyr | Pro |  |
| 550 |  |  |  |  | 555 |  |  |  |  | 560 |  |  |  |  |  |  |
| CTG | CAG | AAC | GGC | TCC | GCG | CCC | TGC | ACC | GAG | CTG | GTG | CCC | CGG | GCG | GCC | 2502 |
| Leu | Gln | Asn | Gly | Ser | Ala | Pro | Cys | Thr | Glu | Leu | Val | Pro | Arg | Ala | Ala |  |
| 565 |  |  |  | 570 |  |  |  |  | 575 |  |  |  |  | 580 |  |  |
| GAG | CCG | GGC | TAC | CTG | GTG | ACC | AAG | GTG | GTG | GCG | GTG | GAC | GGC | GAC | TCG | 2550 |
| Glu | Pro | Gly | Tyr | Leu | Val | Thr | Lys | Val | Val | Ala | Val | Asp | Gly | Asp | Ser |  |
|  |  |  |  | 585 |  |  |  |  | 590 |  |  |  |  | 595 |  |  |
| GGC | CAG | AAC | GCC | TGG | CTG | TCG | TAC | CAG | CTG | CTC | AAG | GCC | ACG | GAG | CCC | 2598 |
| Gly | Gln | Asn | Ala | Trp | Leu | Ser | Tyr | Gln | Leu | Leu | Lys | Ala | Thr | Glu | Pro |  |
|  |  |  | 600 |  |  |  |  | 605 |  |  |  |  | 610 |  |  |  |
| GGG | CTG | TTC | GGC | GTG | TGG | GCG | CAC | AAT | GGC | GAG | GTG | CGC | ACC | GCC | AGG | 2646 |
| Gly | Leu | Phe | Gly | Val | Trp | Ala | His | Asn | Gly | Glu | Val | Arg | Thr | Ala | Arg |  |
|  |  | 615 |  |  |  |  | 620 |  |  |  |  | 625 |  |  |  |  |
| CTG | CTG | AGC | GAG | CGC | GAC | GTG | GCC | AAG | CAC | AGG | CTA | GTG | GTG | CTG | GTC | 2694 |
| Leu | Leu | Ser | Glu | Arg | Asp | Val | Ala | Lys | His | Arg | Leu | Val | Val | Leu | Val |  |
|  | 630 |  |  |  |  | 635 |  |  |  |  | 640 |  |  |  |  |  |
| AAG | GAC | AAT | GGC | GAG | CCT | CCG | CGC | TCG | GCC | ACA | GCC | ACG | CTG | CAA | GTG | 2742 |
| Lys | Asp | Asn | Gly | Glu | Pro | Pro | Arg | Ser | Ala | Thr | Ala | Thr | Leu | Gln | Val |  |
| 645 |  |  |  |  | 650 |  |  |  | 655 |  |  |  |  |  | 660 |  |
| CTC | CTG | GTG | GAC | GGC | TTC | TCT | CAG | CCC | TAC | CTG | CCG | CTC | CCA | GAG | GCG | 2790 |
| Leu | Leu | Val | Asp | Gly | Phe | Ser | Gln | Pro | Tyr | Leu | Pro | Leu | Pro | Glu | Ala |  |
|  |  |  |  | 665 |  |  |  |  | 670 |  |  |  |  | 675 |  |  |
| GCC | CCG | GCC | CAA | GCC | CAG | GCC | GAC | TCG | CTT | ACC | GTC | TAC | CTG | GTG | GTG | 2838 |
| Ala | Pro | Ala | Gln | Ala | Gln | Ala | Asp | Ser | Leu | Thr | Val | Tyr | Leu | Val | Val |  |
|  |  |  | 680 |  |  |  |  | 685 |  |  |  |  | 690 |  |  |  |
| GCA | TTG | GCC | TCG | GTG | TCT | TCG | CTC | TTC | CTC | TTC | TCG | GTG | TTC | CTG | TTC | 2886 |
| Ala | Leu | Ala | Ser | Val | Ser | Ser | Leu | Phe | Leu | Phe | Ser | Val | Phe | Leu | Phe |  |
|  |  | 695 |  |  |  |  | 700 |  |  |  |  | 705 |  |  |  |  |
| GTG | GCA | GTG | CGG | CTG | TGC | AGG | AGG | AGC | AGG | GCG | GCC | TCA | GTG | GGT | CGC | 2934 |
| Val | Ala | Val | Arg | Leu | Cys | Arg | Arg | Ser | Arg | Ala | Ala | Ser | Val | Gly | Arg |  |
|  | 710 |  |  |  |  | 715 |  |  |  |  | 720 |  |  |  |  |  |
| TGC | TCG | GTG | CCC | GAG | GGC | CCC | TTT | CCA | GGG | CAT | CTG | GTG | GAC | GTG | AGC | 2982 |
| Cys | Ser | Val | Pro | Glu | Gly | Pro | Phe | Pro | Gly | His | Leu | Val | Asp | Val | Ser |  |
| 725 |  |  |  |  | 730 |  |  |  | 735 |  |  |  |  |  | 740 |  |
| GGC | ACC | GGG | ACC | CTT | TCC | CAG | AGC | TAC | CAG | TAC | GAG | GTG | TGT | CTG | ACG | 3030 |
| Gly | Thr | Gly | Thr | Leu | Ser | Gln | Ser | Tyr | Gln | Tyr | Glu | Val | Cys | Leu | Thr |  |

```
                                 745                      750                       755
GGA  GGC  TCT  GAA  AGT  AAT  GAT  TTC  AAG  TTC  TTG  AAG  CCT  ATA  TTC  CCA              3078
Gly  Gly  Ser  Glu  Ser  Asn  Asp  Phe  Lys  Phe  Leu  Lys  Pro  Ile  Phe  Pro
               760                      765                      770

AAT  ATT  GTA  AGC  CAG  GAC  TCT  AGG  AGG  AAA  TCA  GAA  TTT  CTA  GAA                   3123
Asn  Ile  Val  Ser  Gln  Asp  Ser  Arg  Arg  Lys  Ser  Glu  Phe  Leu  Glu
          775                      780                      785

TAATGTAGGT  ATCTGTAGCT  TTCCGACCGT  CTGTTAATTT  TGTCTTCCTC  ACTTTTCACC                       3183

TTAGTTTTTT  TTAACCCTTT  AGTAATCTTG  AATTCTACTT  TTTTTAAAT   TTCTACTGTT                       3243

GTCTTTAGTA  ATGTTACTCA  TTTCCTTTGT  CTGATTGTTA  GTTTCAAAT   TATTGTATTA                       3303

TTATAAATAT  TTTATATCAG  GAAAGTTCAT  ATTTCTGAAT  AAATTAATAG                                   3353
```

( 2 ) INFORMATION FOR SEQ ID NO:110:

( i ) SEQUENCE CHARACTERISTICS:
        ( A ) LENGTH: 787 amino acids
        ( B ) TYPE: amino acid
        ( D ) TOPOLOGY: linear ( i i ) MOLECULE TYPE: protein ( x i ) SEQUENCE DESCRIPTION: SEQ ID NO:110:

```
Met  Glu  Pro  Ala  Gly  Glu  Arg  Phe  Pro  Glu  Gln  Arg  Gln  Val  Leu  Ile
 1                  5                        10                      15

Leu  Leu  Leu  Leu  Leu  Glu  Val  Thr  Leu  Ala  Gly  Trp  Glu  Pro  Arg  Arg
               20                       25                      30

Tyr  Ser  Val  Met  Glu  Glu  Thr  Glu  Arg  Gly  Ser  Phe  Val  Ala  Asn  Leu
               35                       40                      45

Ala  Asn  Asp  Leu  Gly  Leu  Gly  Val  Gly  Glu  Leu  Ala  Glu  Arg  Gly  Ala
     50                       55                      60

Arg  Val  Val  Ser  Glu  Asp  Asn  Glu  Gln  Gly  Leu  Gln  Leu  Asp  Leu  Gln
 65                      70                      75                       80

Thr  Gly  Gln  Leu  Ile  Leu  Asn  Glu  Lys  Leu  Asp  Arg  Glu  Lys  Leu  Cys
               85                       90                      95

Gly  Pro  Thr  Glu  Pro  Cys  Ile  Met  His  Phe  Gln  Val  Leu  Leu  Lys  Lys
              100                      105                     110

Pro  Leu  Glu  Val  Phe  Arg  Ala  Glu  Leu  Leu  Val  Thr  Asp  Ile  Asn  Asp
              115                      120                     125

His  Ser  Pro  Glu  Phe  Pro  Glu  Arg  Glu  Met  Thr  Leu  Lys  Ile  Pro  Glu
     130                     135                     140

Thr  Ser  Ser  Leu  Gly  Thr  Val  Phe  Pro  Leu  Lys  Lys  Ala  Arg  Asp  Leu
145                      150                     155                      160

Asp  Val  Gly  Ser  Asn  Asn  Val  Gln  Asn  Tyr  Asn  Ile  Ser  Pro  Asn  Ser
                    165                     170                     175

His  Phe  His  Val  Ser  Thr  Arg  Thr  Arg  Gly  Asp  Gly  Arg  Lys  Tyr  Pro
               180                      185                     190

Glu  Leu  Val  Leu  Asp  Thr  Glu  Leu  Asp  Arg  Glu  Glu  Gln  Ala  Glu  Leu
               195                      200                     205

Arg  Leu  Thr  Leu  Thr  Ala  Val  Asp  Gly  Gly  Ser  Pro  Pro  Arg  Ser  Gly
     210                      215                     220

Thr  Val  Gln  Ile  Leu  Ile  Leu  Val  Leu  Asp  Ala  Asn  Asp  Asn  Ala  Pro
225                      230                      235                      240

Glu  Phe  Val  Gln  Ala  Leu  Tyr  Glu  Val  Gln  Val  Pro  Glu  Asn  Ser  Pro
                    245                      250                     255

Val  Gly  Ser  Leu  Val  Val  Lys  Val  Ser  Ala  Arg  Asp  Leu  Asp  Thr  Gly
                    260                      265                     270
```

```
Thr  Asn  Gly  Glu  Ile  Ser  Tyr  Ser  Leu  Tyr  Tyr  Ser  Ser  Gln  Glu  Ile
          275                      280                     285

Asp  Lys  Pro  Phe  Glu  Leu  Ser  Ser  Leu  Ser  Gly  Glu  Ile  Arg  Leu  Ile
     290                      295                     300

Lys  Lys  Leu  Asp  Phe  Glu  Thr  Met  Ser  Ser  Tyr  Asp  Leu  Asp  Ile  Glu
305                      310                     315                          320

Ala  Ser  Asp  Gly  Gly  Gly  Leu  Ser  Gly  Lys  Cys  Ser  Val  Ser  Val  Lys
               325                     330                          335

Val  Leu  Asp  Val  Asn  Asp  Asn  Phe  Pro  Glu  Leu  Ser  Ile  Ser  Ser  Leu
               340                     345                     350

Thr  Ser  Pro  Ile  Pro  Glu  Asn  Ser  Pro  Glu  Thr  Glu  Val  Ala  Leu  Phe
          355                      360                     365

Arg  Ile  Arg  Asp  Arg  Asp  Ser  Gly  Glu  Asn  Gly  Lys  Met  Ile  Cys  Ser
     370                      375                     380

Ile  Gln  Asp  Asp  Val  Pro  Phe  Lys  Leu  Lys  Pro  Ser  Val  Glu  Asn  Phe
385                      390                     395                          400

Tyr  Arg  Leu  Val  Thr  Glu  Gly  Ala  Leu  Asp  Arg  Glu  Thr  Arg  Ala  Glu
               405                     410                          415

Tyr  Asn  Ile  Thr  Ile  Thr  Ile  Thr  Asp  Leu  Gly  Thr  Pro  Arg  Leu  Lys
               420                     425                     430

Thr  Glu  Gln  Ser  Ile  Thr  Val  Leu  Val  Ser  Asp  Val  Asn  Asp  Asn  Ala
          435                      440                     445

Pro  Ala  Phe  Thr  Gln  Thr  Ser  Tyr  Thr  Leu  Phe  Val  Arg  Glu  Asn  Asn
     450                      455                     460

Ser  Pro  Ala  Leu  His  Ile  Gly  Ser  Val  Ser  Ala  Thr  Asp  Arg  Asp  Ser
465                      470                     475                          480

Gly  Thr  Asn  Ala  Gln  Val  Thr  Tyr  Ser  Leu  Leu  Pro  Pro  Gln  Asp  Pro
               485                     490                          495

His  Leu  Pro  Leu  Thr  Ser  Leu  Val  Ser  Ile  Asn  Thr  Asp  Asn  Gly  His
               500                     505                     510

Leu  Phe  Ala  Leu  Gln  Ser  Leu  Asp  Tyr  Glu  Ala  Leu  Gln  Ala  Phe  Glu
          515                      520                     525

Phe  Arg  Val  Gly  Ala  Thr  Asp  Arg  Gly  Phe  Pro  Ala  Leu  Ser  Ser  Glu
     530                      535                     540

Ala  Leu  Val  Arg  Val  Leu  Val  Leu  Asp  Ala  Asn  Asp  Asn  Ser  Pro  Phe
545                      550                     555                          560

Val  Leu  Tyr  Pro  Leu  Gln  Asn  Gly  Ser  Ala  Pro  Cys  Thr  Glu  Leu  Val
               565                     570                          575

Pro  Arg  Ala  Ala  Glu  Pro  Gly  Tyr  Leu  Val  Thr  Lys  Val  Val  Ala  Val
               580                     585                     590

Asp  Gly  Asp  Ser  Gly  Gln  Asn  Ala  Trp  Leu  Ser  Tyr  Gln  Leu  Leu  Lys
          595                      600                     605

Ala  Thr  Glu  Pro  Gly  Leu  Phe  Gly  Val  Trp  Ala  His  Asn  Gly  Glu  Val
     610                      615                     620

Arg  Thr  Ala  Arg  Leu  Leu  Ser  Glu  Arg  Asp  Val  Ala  Lys  His  Arg  Leu
625                      630                     635                          640

Val  Val  Leu  Val  Lys  Asp  Asn  Gly  Glu  Pro  Pro  Arg  Ser  Ala  Thr  Ala
               645                     650                          655

Thr  Leu  Gln  Val  Leu  Leu  Val  Asp  Gly  Phe  Ser  Gln  Pro  Tyr  Leu  Pro
               660                     665                     670

Leu  Pro  Glu  Ala  Ala  Pro  Ala  Gln  Ala  Gln  Ala  Asp  Ser  Leu  Thr  Val
          675                      680                     685

Tyr  Leu  Val  Val  Ala  Leu  Ala  Ser  Val  Ser  Ser  Leu  Phe  Leu  Phe  Ser
```

|  |  |  |  |  | 690 |  |  |  |  | 695 |  |  |  |  | 700 |  |  |  |
|---|---|---|---|---|---|---|---|---|---|---|---|---|---|---|---|---|---|---|
| Val | Phe | Leu | Phe | Val | Ala | Val | Arg | Leu | Cys | Arg | Arg | Ser | Arg | Ala | Ala |
| 705 |  |  |  |  | 710 |  |  |  |  | 715 |  |  |  |  | 720 |
| Ser | Val | Gly | Arg | Cys | Ser | Val | Pro | Glu | Gly | Pro | Phe | Pro | Gly | His | Leu |
|  |  |  |  | 725 |  |  |  |  | 730 |  |  |  |  | 735 |  |
| Val | Asp | Val | Ser | Gly | Thr | Gly | Thr | Leu | Ser | Gln | Ser | Tyr | Gln | Tyr | Glu |
|  |  |  | 740 |  |  |  |  | 745 |  |  |  |  | 750 |  |  |
| Val | Cys | Leu | Thr | Gly | Gly | Ser | Glu | Ser | Asn | Asp | Phe | Lys | Phe | Leu | Lys |
|  |  | 755 |  |  |  |  | 760 |  |  |  |  | 765 |  |  |  |
| Pro | Ile | Phe | Pro | Asn | Ile | Val | Ser | Gln | Asp | Ser | Arg | Arg | Lys | Ser | Glu |
|  |  | 770 |  |  |  | 775 |  |  |  |  | 780 |  |  |  |  |
| Phe | Leu | Glu |
| 785 |  |  |

( 2 ) INFORMATION FOR SEQ ID NO:111:

( i ) SEQUENCE CHARACTERISTICS:
        ( A ) LENGTH: 3033 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 138..2528

( x i ) SEQUENCE DESCRIPTION: SEQ ID NO:111:

```
GTGATTGGAC GTGTTTTTGT GACTATTTGG GAAGAAGACA CCTTCCTAAT CAGATTTACT      60

CCAATATCTT CCCGGACCCT CATGAGTGGA TTGCAATTGA CTTGAAGAAG CAGCACCCTC     120
```

|  |  |  |  |  |  | AGGACTGAAT | CTGAACA | ATG<br>Met<br>1 | GAG<br>Glu | ACA<br>Thr | GCA<br>Ala | CTA<br>Leu<br>5 | GCA<br>Ala | AAA<br>Lys | ATA<br>Ile | CCA<br>Pro | CAG<br>Gln | CAA<br>Gln<br>10 | 170 |
|---|---|---|---|---|---|---|---|---|---|---|---|---|---|---|---|---|---|---|---|
| AGG<br>Arg | CAA<br>Gln | GTC<br>Val | TTT<br>Phe<br>15 | TTT<br>Phe | CTT<br>Leu | ACT<br>Thr | ATA<br>Ile | TTG<br>Leu<br>20 | TCG<br>Ser | TTA<br>Leu | TTG<br>Leu | TGG<br>Trp | AAG<br>Lys<br>25 | TCT<br>Ser | AGC<br>Ser |  |  |  | 218 |
| TCT<br>Ser | GAG<br>Glu | GCC<br>Ala<br>30 | ATT<br>Ile | AGA<br>Arg | TAT<br>Tyr | TCC<br>Ser | ATG<br>Met<br>35 | CCA<br>Pro | GAA<br>Glu | GAA<br>Glu | ACA<br>Thr | GAG<br>Glu<br>40 | AGT<br>Ser | GGC<br>Gly | TAT<br>Tyr |  |  |  | 266 |
| ATG<br>Met | GTG<br>Val<br>45 | GCT<br>Ala | AAC<br>Asn | CTG<br>Leu | GCG<br>Ala | AAA<br>Lys<br>50 | GAT<br>Asp | CTG<br>Leu | GGG<br>Gly | ATC<br>Ile | AGG<br>Arg<br>55 | GTT<br>Val | GGA<br>Gly | GAA<br>Glu | CTG<br>Leu |  |  |  | 314 |
| TCC<br>Ser<br>60 | TCT<br>Ser | AGA<br>Arg | GGA<br>Gly | GCT<br>Ala | CAA<br>Gln<br>65 | ATC<br>Ile | CAT<br>His | TAC<br>Tyr | AAA<br>Lys | GGA<br>Gly<br>70 | AAC<br>Asn | AAA<br>Lys | GAA<br>Glu | CTT<br>Leu | TTG<br>Leu<br>75 |  |  |  | 362 |
| CAG<br>Gln | CTG<br>Leu | GAT<br>Asp | GCA<br>Ala | GAG<br>Glu<br>80 | ACT<br>Thr | GGG<br>Gly | AAT<br>Asn | TTG<br>Leu | TTC<br>Phe<br>85 | TTA<br>Leu | AAG<br>Lys | GAA<br>Glu | AAA<br>Lys | CTA<br>Leu<br>90 | GAC<br>Asp |  |  |  | 410 |
| AGA<br>Arg | GAA<br>Glu | CTG<br>Leu<br>95 | CTG<br>Leu | TGT<br>Cys | GGA<br>Gly | GAG<br>Glu | ACA<br>Thr<br>100 | GAA<br>Glu | CCC<br>Pro | TGT<br>Cys | GTG<br>Val | CTG<br>Leu<br>105 | AAC<br>Asn | TTC<br>Phe | CAG<br>Gln |  |  |  | 458 |
| ATC<br>Ile | ATA<br>Ile<br>110 | CTG<br>Leu | GAA<br>Glu | AAC<br>Asn | CCT<br>Pro | ATG<br>Met<br>115 | CAG<br>Gln | TTC<br>Phe | TTC<br>Phe | CAA<br>Gln | ACT<br>Thr<br>120 | GAA<br>Glu | CTG<br>Leu | CAG<br>Gln | CTC<br>Leu |  |  |  | 506 |
| ACA<br>Thr | GAT<br>Asp<br>125 | ATA<br>Ile | AAC<br>Asn | GAC<br>Asp | CAT<br>His | TCT<br>Ser<br>130 | CCA<br>Pro | GAG<br>Glu | TTC<br>Phe | CCC<br>Pro | AAC<br>Asn<br>135 | AAG<br>Lys | AAA<br>Lys | ATG<br>Met | CTT<br>Leu |  |  |  | 554 |
| CTA<br>Leu<br>140 | ACA<br>Thr | ATT<br>Ile | CCT<br>Pro | GAG<br>Glu | AGT<br>Ser<br>145 | GCC<br>Ala | CAT<br>His | CCA<br>Pro | GGG<br>Gly | ACT<br>Thr<br>150 | GTG<br>Val | TTT<br>Phe | CCT<br>Pro | CTG<br>Leu | AAG<br>Lys<br>155 |  |  |  | 602 |

| | | | | | | | | | | | | | | | | |
|---|---|---|---|---|---|---|---|---|---|---|---|---|---|---|---|---|
| GCA | GCT | CGG | GAC | TCT | GAC | ATA | GGG | AGC | AAC | GCT | GTT | CAG | AAC | TAC | ACA | 650 |
| Ala | Ala | Arg | Asp | Ser | Asp | Ile | Gly | Ser | Asn | Ala | Val | Gln | Asn | Tyr | Thr | |
| | | | | 160 | | | | | 165 | | | | | 170 | | |
| GTC | AAT | CCC | AAC | CTC | CAT | TTC | CAC | GTC | GTT | ACT | CAC | AGT | CGC | ACA | GAT | 698 |
| Val | Asn | Pro | Asn | Leu | His | Phe | His | Val | Val | Thr | His | Ser | Arg | Thr | Asp | |
| | | | 175 | | | | | 180 | | | | | 185 | | | |
| GGC | AGG | AAA | TAC | CCA | GAG | CTG | GTG | CTG | GAC | AGA | GCC | CTG | GAT | AGG | GAG | 746 |
| Gly | Arg | Lys | Tyr | Pro | Glu | Leu | Val | Leu | Asp | Arg | Ala | Leu | Asp | Arg | Glu | |
| | | 190 | | | | | 195 | | | | | 200 | | | | |
| GAG | CAG | CCT | GAG | CTC | ACT | TTA | ATC | CTC | ACT | GCT | CTG | GAT | GGT | GGA | GCT | 794 |
| Glu | Gln | Pro | Glu | Leu | Thr | Leu | Ile | Leu | Thr | Ala | Leu | Asp | Gly | Gly | Ala | |
| | | 205 | | | | | 210 | | | | | 215 | | | | |
| CCT | TCC | AGG | TCA | GGA | ACC | ACC | ACA | GTT | CAC | ATA | GAA | GTT | GTG | GAC | ATC | 842 |
| Pro | Ser | Arg | Ser | Gly | Thr | Thr | Thr | Val | His | Ile | Glu | Val | Val | Asp | Ile | |
| 220 | | | | | 225 | | | | | 230 | | | | | 235 | |
| AAT | GAT | AAC | TCC | CCC | CAG | TTT | GTA | CAG | TCA | CTC | TAT | AAG | GTG | CAA | GTT | 890 |
| Asn | Asp | Asn | Ser | Pro | Gln | Phe | Val | Gln | Ser | Leu | Tyr | Lys | Val | Gln | Val | |
| | | | | 240 | | | | | 245 | | | | | 250 | | |
| CCT | GAG | AAT | AAT | CCC | CTC | AAT | GCC | TTT | GTT | GTC | ACG | GTC | TCT | GCC | ACG | 938 |
| Pro | Glu | Asn | Asn | Pro | Leu | Asn | Ala | Phe | Val | Val | Thr | Val | Ser | Ala | Thr | |
| | | | 255 | | | | | 260 | | | | | 265 | | | |
| GAT | TTA | GAT | GCT | GGG | GTA | TAT | GGC | AAT | GTG | ACC | TAT | TCT | CTG | TTT | CAA | 986 |
| Asp | Leu | Asp | Ala | Gly | Val | Tyr | Gly | Asn | Val | Thr | Tyr | Ser | Leu | Phe | Gln | |
| | | 270 | | | | | 275 | | | | | 280 | | | | |
| GGG | TAT | GGG | GTA | TTT | CAA | CCA | TTT | GTA | ATA | GAC | GAA | ATC | ACT | GGA | GAA | 1034 |
| Gly | Tyr | Gly | Val | Phe | Gln | Pro | Phe | Val | Ile | Asp | Glu | Ile | Thr | Gly | Glu | |
| | 285 | | | | | 290 | | | | | 295 | | | | | |
| ATC | CAT | CTG | AGC | AAA | GAG | CTG | GAT | TTT | GAG | GAA | ATT | AGC | AAT | CAT | AAC | 1082 |
| Ile | His | Leu | Ser | Lys | Glu | Leu | Asp | Phe | Glu | Glu | Ile | Ser | Asn | His | Asn | |
| 300 | | | | | 305 | | | | | 310 | | | | | 315 | |
| ATA | GAA | ATC | GCA | GCC | ACA | GAT | GGA | GGA | GGC | CTT | TCA | GGA | AAA | TGC | ACT | 1130 |
| Ile | Glu | Ile | Ala | Ala | Thr | Asp | Gly | Gly | Gly | Leu | Ser | Gly | Lys | Cys | Thr | |
| | | | | 320 | | | | | 325 | | | | | 330 | | |
| GTG | GCT | GTA | CAG | GTG | TTG | GAT | GTG | AAT | GAC | AAC | GCC | CCA | GAG | TTG | ACA | 1178 |
| Val | Ala | Val | Gln | Val | Leu | Asp | Val | Asn | Asp | Asn | Ala | Pro | Glu | Leu | Thr | |
| | | | 335 | | | | | 340 | | | | | 345 | | | |
| ATT | AGG | AAG | CTC | ACA | GTC | CTG | GTC | CCA | GAA | AAT | TCC | GCA | GAG | ACT | GTA | 1226 |
| Ile | Arg | Lys | Leu | Thr | Val | Leu | Val | Pro | Glu | Asn | Ser | Ala | Glu | Thr | Val | |
| | | 350 | | | | | 355 | | | | | 360 | | | | |
| GTT | GCT | GTT | TTT | AGT | GTT | TCT | GAT | TCT | GAT | TCG | GGG | GAC | AAT | GGA | AGG | 1274 |
| Val | Ala | Val | Phe | Ser | Val | Ser | Asp | Ser | Asp | Ser | Gly | Asp | Asn | Gly | Arg | |
| | 365 | | | | | 370 | | | | | 375 | | | | | |
| ATG | GTG | TGT | TCT | ATT | CCG | AAC | AAT | ATC | CCA | TTT | CTC | CTG | AAA | CCC | ACA | 1322 |
| Met | Val | Cys | Ser | Ile | Pro | Asn | Asn | Ile | Pro | Phe | Leu | Leu | Lys | Pro | Thr | |
| 380 | | | | | 385 | | | | | 390 | | | | | 395 | |
| TTT | GAG | AAT | TAT | TAC | ACG | TTA | GTG | ACT | GAG | GGG | CCA | CTT | GAT | AGA | GAG | 1370 |
| Phe | Glu | Asn | Tyr | Tyr | Thr | Leu | Val | Thr | Glu | Gly | Pro | Leu | Asp | Arg | Glu | |
| | | | | 400 | | | | | 405 | | | | | 410 | | |
| AAC | AGA | GCT | GAG | TAC | AAC | ATC | ACC | ATC | ACG | GTC | TCA | GAT | CTG | GGC | ACA | 1418 |
| Asn | Arg | Ala | Glu | Tyr | Asn | Ile | Thr | Ile | Thr | Val | Ser | Asp | Leu | Gly | Thr | |
| | | | 415 | | | | | 420 | | | | | 425 | | | |
| CCC | AGG | CTC | ACA | ACC | CAG | CAC | ACC | ATA | ACA | GTG | CAA | GTG | TCC | GAC | ATC | 1466 |
| Pro | Arg | Leu | Thr | Thr | Gln | His | Thr | Ile | Thr | Val | Gln | Val | Ser | Asp | Ile | |
| | | 430 | | | | | 435 | | | | | 440 | | | | |
| AAC | GAC | AAC | GCC | CCT | GCC | TTC | ACC | CAA | ACC | TCC | TAC | ACC | ATG | TTT | GTC | 1514 |
| Asn | Asp | Asn | Ala | Pro | Ala | Phe | Thr | Gln | Thr | Ser | Tyr | Thr | Met | Phe | Val | |
| | | 445 | | | | | 450 | | | | | 455 | | | | |
| CAC | GAG | AAC | AAC | AGC | CCC | GCC | CTG | CAC | ATA | GGC | ACC | ATC | AGT | GCC | ACA | 1562 |
| His | Glu | Asn | Asn | Ser | Pro | Ala | Leu | His | Ile | Gly | Thr | Ile | Ser | Ala | Thr | |
| 460 | | | | | 465 | | | | | 470 | | | | | 475 | |

```
GAC TCA GAC TCA GGC TCC AAT GCC CAC ATC ACC TAC TCG CTG CTG CCG          1610
Asp Ser Asp Ser Gly Ser Asn Ala His Ile Thr Tyr Ser Leu Leu Pro
            480             485                     490

CCT GAT GAC CCG CAG CTG GCC CTC GAC TCA CTC ATC TCC ATC AAT GTT          1658
Pro Asp Asp Pro Gln Leu Ala Leu Asp Ser Leu Ile Ser Ile Asn Val
            495             500             505

GAC AAT GGG CAG CTG TTC GCG CTC AGA GCT CTA GAC TAT GAG GCA CTG          1706
Asp Asn Gly Gln Leu Phe Ala Leu Arg Ala Leu Asp Tyr Glu Ala Leu
            510             515             520

CAG TCC TTC GAG TTC TAC GTG GGC GCT ACA GAT GGA GGC TCA CCC GCG          1754
Gln Ser Phe Glu Phe Tyr Val Gly Ala Thr Asp Gly Gly Ser Pro Ala
        525             530             535

CTC AGC AGC CAG ACT CTG GTG CGG ATG GTG GTG CTG GAT GAC AAT GAC          1802
Leu Ser Ser Gln Thr Leu Val Arg Met Val Val Leu Asp Asp Asn Asp
540             545             550             555

AAT GCC CCC TTC GTG CTC TAC CCA CTG CAG AAT GCC TCA GCA CCC TGT          1850
Asn Ala Pro Phe Val Leu Tyr Pro Leu Gln Asn Ala Ser Ala Pro Cys
                560             565             570

ACT GAG CTA CTG CCT AGG GCA GCA GAG CCC GGC TAC CTG ATC ACC AAA          1898
Thr Glu Leu Leu Pro Arg Ala Ala Glu Pro Gly Tyr Leu Ile Thr Lys
            575             580             585

GTG GTG GCT GTG GAT CGC GAC TCT GGA CAG AAT GCT TGG CTG TCG TTC          1946
Val Val Ala Val Asp Arg Asp Ser Gly Gln Asn Ala Trp Leu Ser Phe
            590             595             600

CAG CTA CTT AAA GCT ACA GAG CCA GGG CTG TTC AGT GTA TGG GCA CAC          1994
Gln Leu Leu Lys Ala Thr Glu Pro Gly Leu Phe Ser Val Trp Ala His
        605             610             615

AAT GGT GAA GTG CGC ACC ACT AGG CTG CTG AGT GAG CGA GAT GCT CAG          2042
Asn Gly Glu Val Arg Thr Thr Arg Leu Leu Ser Glu Arg Asp Ala Gln
620             625             630             635

AAG CAC AAG CTA CTG CTG CTG GTC AAG GAC AAT GGC GAT CCT CTG CGC          2090
Lys His Lys Leu Leu Leu Leu Val Lys Asp Asn Gly Asp Pro Leu Arg
            640             645             650

TCT GCC AAT GTC ACT CTT CAC GTG CTA GTG GTG GAT GGC TTC TCG CAG          2138
Ser Ala Asn Val Thr Leu His Val Leu Val Val Asp Gly Phe Ser Gln
            655             660             665

CCT TAC CTA CCA TTG GCT GAG GTG GCA CAG GAT TCC ATG CAA GAT AAT          2186
Pro Tyr Leu Pro Leu Ala Glu Val Ala Gln Asp Ser Met Gln Asp Asn
            670             675             680

TAC GAC GTT CTC ACA CTG TAC CTA GTC ATT GCC TTG GCA TCT GTA TCT          2234
Tyr Asp Val Leu Thr Leu Tyr Leu Val Ile Ala Leu Ala Ser Val Ser
            685             690             695

TCT CTC TTC CTC TTG TCT GTA GTG CTG TTT GTG GGG GTG AGG CTG TGC          2282
Ser Leu Phe Leu Leu Ser Val Val Leu Phe Val Gly Val Arg Leu Cys
700             705             710             715

AGG AGG GCC AGG GAG GCC TCC TTG GGT GAC TAC TCT GTG CCT GAG GGA          2330
Arg Arg Ala Arg Glu Ala Ser Leu Gly Asp Tyr Ser Val Pro Glu Gly
            720             725             730

CAC TTT CCT AGC CAC TTG GTG GAT GTC AGC GGT GCC GGG ACC CTG TCC          2378
His Phe Pro Ser His Leu Val Asp Val Ser Gly Ala Gly Thr Leu Ser
            735             740             745

CAG AGT TAT CAA TAT GAG GTG TGT CTT AAT GGA GGT ACT AGA ACA AAT          2426
Gln Ser Tyr Gln Tyr Glu Val Cys Leu Asn Gly Gly Thr Arg Thr Asn
        750             755             760

GAG TTT AAC TTT CTT AAA CCA TTG TTT CCT ATC CTT CCG ACC CAG GCT          2474
Glu Phe Asn Phe Leu Lys Pro Leu Phe Pro Ile Leu Pro Thr Gln Ala
765             770             775

GCT GCT GCT GAA GAA AGA GAA AAC GCT GTT GTG CAC AAT AGC GTT GGA          2522
Ala Ala Ala Glu Glu Arg Glu Asn Ala Val Val His Asn Ser Val Gly
780             785             790             795
```

```
TTC TAT TAGAGCACTG ATTTTGAAGT GGTGGTTACC TCATTTTCC TTAACTATCC        2578
Phe Tyr

CTGATGTAGA ATGGTGTAGT GCCGTGAATC AACTCCTGAG ATATATGTTC ATTTTATCCT    2638

TTGTTTTGAA TCAAACTATT CAGATGTGAT CCTACTCTAG AGAATTGGT TCTACTCCAT     2698

TGTGTTTGTT TAGATTTCTA CGCCATACCA GTGCATGCTG GGTTGTTTTT TTTTTACAA     2758

TTATTATAAC TTTGCTTTGG AGGGGAACTC ATATTCGCTG TAACGAATTG GAACCACTTT    2818

CATTGTTAGA GATGCCTTGC TTTGTTGTGT TATTTCAGAC AGGGTCTTAA ATTGTAGCCC    2878

TGGGTGACCT GAAATGACTA TGTACAGACT GACTTTGAAT TTGTGGCAGT CCATCTGCCT    2938

CTGTTGTCCT ATGTTGGGAT TGTGAGCATG CATGAGTAGG CTCAGCTGTG GTGAGCGACC    2998

TTAATAAAAA TCAAATACTA AAAAAAAAAA AAAAA                               3033
```

( 2 ) INFORMATION FOR SEQ ID NO:112:

( i ) SEQUENCE CHARACTERISTICS:
        ( A ) LENGTH: 797 amino acids
        ( B ) TYPE: amino acid
        ( D ) TOPOLOGY: linear ( i i ) MOLECULE TYPE: protein ( x i ) SEQUENCE DESCRIPTION: SEQ ID NO:112:

```
Met Glu Thr Ala Leu Ala Lys Ile Pro Gln Gln Arg Gln Val Phe Phe
 1               5                  10                  15

Leu Thr Ile Leu Ser Leu Leu Trp Lys Ser Ser Ser Glu Ala Ile Arg
                20                  25                  30

Tyr Ser Met Pro Glu Glu Thr Glu Ser Gly Tyr Met Val Ala Asn Leu
            35                  40                  45

Ala Lys Asp Leu Gly Ile Arg Val Gly Glu Leu Ser Ser Arg Gly Ala
        50                  55                  60

Gln Ile His Tyr Lys Gly Asn Lys Glu Leu Leu Gln Leu Asp Ala Glu
65                  70                  75                  80

Thr Gly Asn Leu Phe Leu Lys Glu Lys Leu Asp Arg Glu Leu Leu Cys
                85                  90                  95

Gly Glu Thr Glu Pro Cys Val Leu Asn Phe Gln Ile Ile Leu Glu Asn
                100                 105                 110

Pro Met Gln Phe Phe Gln Thr Glu Leu Gln Leu Thr Asp Ile Asn Asp
            115                 120                 125

His Ser Pro Glu Phe Pro Asn Lys Lys Met Leu Leu Thr Ile Pro Glu
        130                 135                 140

Ser Ala His Pro Gly Thr Val Phe Pro Leu Lys Ala Ala Arg Asp Ser
145                 150                 155                 160

Asp Ile Gly Ser Asn Ala Val Gln Asn Tyr Thr Val Asn Pro Asn Leu
                165                 170                 175

His Phe His Val Val Thr His Ser Arg Thr Asp Gly Arg Lys Tyr Pro
            180                 185                 190

Glu Leu Val Leu Asp Arg Ala Leu Asp Arg Glu Glu Gln Pro Glu Leu
        195                 200                 205

Thr Leu Ile Leu Thr Ala Leu Asp Gly Gly Ala Pro Ser Arg Ser Gly
    210                 215                 220

Thr Thr Thr Val His Ile Glu Val Val Asp Ile Asn Asp Asn Ser Pro
225                 230                 235                 240

Gln Phe Val Gln Ser Leu Tyr Lys Val Gln Val Pro Glu Asn Asn Pro
                245                 250                 255
```

```
Leu Asn Ala Phe Val Val Thr Val Ser Ala Thr Asp Leu Asp Ala Gly
            260                 265                 270
Val Tyr Gly Asn Val Thr Tyr Ser Leu Phe Gln Gly Tyr Gly Val Phe
        275                 280                 285
Gln Pro Phe Val Ile Asp Glu Ile Thr Gly Glu Ile His Leu Ser Lys
    290                 295                 300
Glu Leu Asp Phe Glu Glu Ile Ser Asn His Asn Ile Glu Ile Ala Ala
305                 310                 315                 320
Thr Asp Gly Gly Gly Leu Ser Gly Lys Cys Thr Val Ala Val Gln Val
                325                 330                 335
Leu Asp Val Asn Asp Asn Ala Pro Glu Leu Thr Ile Arg Lys Leu Thr
            340                 345                 350
Val Leu Val Pro Glu Asn Ser Ala Glu Thr Val Val Ala Val Phe Ser
        355                 360                 365
Val Ser Asp Ser Asp Ser Gly Asp Asn Gly Arg Met Val Cys Ser Ile
    370                 375                 380
Pro Asn Asn Ile Pro Phe Leu Leu Lys Pro Thr Phe Glu Asn Tyr Tyr
385                 390                 395                 400
Thr Leu Val Thr Glu Gly Pro Leu Asp Arg Glu Asn Arg Ala Glu Tyr
                405                 410                 415
Asn Ile Thr Ile Thr Val Ser Asp Leu Gly Thr Pro Arg Leu Thr Thr
            420                 425                 430
Gln His Thr Ile Thr Val Gln Val Ser Asp Ile Asn Asp Asn Ala Pro
        435                 440                 445
Ala Phe Thr Gln Thr Ser Tyr Thr Met Phe Val His Glu Asn Asn Ser
    450                 455                 460
Pro Ala Leu His Ile Gly Thr Ile Ser Ala Thr Asp Ser Asp Ser Gly
465                 470                 475                 480
Ser Asn Ala His Ile Thr Tyr Ser Leu Leu Pro Pro Asp Asp Pro Gln
                485                 490                 495
Leu Ala Leu Asp Ser Leu Ile Ser Ile Asn Val Asp Asn Gly Gln Leu
            500                 505                 510
Phe Ala Leu Arg Ala Leu Asp Tyr Glu Ala Leu Gln Ser Phe Glu Phe
        515                 520                 525
Tyr Val Gly Ala Thr Asp Gly Gly Ser Pro Ala Leu Ser Ser Gln Thr
    530                 535                 540
Leu Val Arg Met Val Val Leu Asp Asp Asn Asp Asn Ala Pro Phe Val
545                 550                 555                 560
Leu Tyr Pro Leu Gln Asn Ala Ser Ala Pro Cys Thr Glu Leu Leu Pro
                565                 570                 575
Arg Ala Ala Glu Pro Gly Tyr Leu Ile Thr Lys Val Val Ala Val Asp
            580                 585                 590
Arg Asp Ser Gly Gln Asn Ala Trp Leu Ser Phe Gln Leu Leu Lys Ala
        595                 600                 605
Thr Glu Pro Gly Leu Phe Ser Val Trp Ala His Asn Gly Glu Val Arg
    610                 615                 620
Thr Thr Arg Leu Leu Ser Glu Arg Asp Ala Gln Lys His Lys Leu Leu
625                 630                 635                 640
Leu Leu Val Lys Asp Asn Gly Asp Pro Leu Arg Ser Ala Asn Val Thr
                645                 650                 655
Leu His Val Leu Val Val Asp Gly Phe Ser Gln Pro Tyr Leu Pro Leu
            660                 665                 670
Ala Glu Val Ala Gln Asp Ser Met Gln Asp Asn Tyr Asp Val Leu Thr
        675                 680                 685
```

| Leu | Tyr | Leu | Val | Ile | Ala | Leu | Ala | Ser | Val | Ser | Ser | Leu | Phe | Leu | Leu |
|---|---|---|---|---|---|---|---|---|---|---|---|---|---|---|---|
| | 690 | | | | | 695 | | | | | 700 | | | | |
| Ser | Val | Val | Leu | Phe | Val | Gly | Val | Arg | Leu | Cys | Arg | Arg | Ala | Arg | Glu |
| 705 | | | | | 710 | | | | | 715 | | | | | 720 |
| Ala | Ser | Leu | Gly | Asp | Tyr | Ser | Val | Pro | Glu | Gly | His | Phe | Pro | Ser | His |
| | | | | 725 | | | | | 730 | | | | | 735 | |
| Leu | Val | Asp | Val | Ser | Gly | Ala | Gly | Thr | Leu | Ser | Gln | Ser | Tyr | Gln | Tyr |
| | | | 740 | | | | | 745 | | | | | 750 | | |
| Glu | Val | Cys | Leu | Asn | Gly | Gly | Thr | Arg | Thr | Asn | Glu | Phe | Asn | Phe | Leu |
| | | 755 | | | | | 760 | | | | | 765 | | | |
| Lys | Pro | Leu | Phe | Pro | Ile | Leu | Pro | Thr | Gln | Ala | Ala | Ala | Ala | Glu | Glu |
| | 770 | | | | | 775 | | | | | 780 | | | | |
| Arg | Glu | Asn | Ala | Val | Val | His | Asn | Ser | Val | Gly | Phe | Tyr | | | |
| 785 | | | | | 790 | | | | | 795 | | | | | |

( 2 ) INFORMATION FOR SEQ ID NO:113:

( i ) SEQUENCE CHARACTERISTICS:
        ( A ) LENGTH: 2347 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:113:

```
AAAACACGGG GGAAATGACA GTAGCAAAGA ATCTGGACTA TGAAGAATGC TCATTGTATG      60
AAATGGAAAT ACAGGCTGAA GATGTGGGGG CGCTTCTGGG GAGGAGCAAA GTGGTAATTA     120
TGGTAGAAGA TGTAAATGAC AATCGGCCAG AAGTGACCAT TACATCCTTG TTTAACCCGG     180
TATTGGAAAA TTCTCTTCCC GGGACAGTAA TTGCCTTCTT GAATGTGCAT GACCGAGACT     240
CTGGAAAGAA CGGCCAAGTT GTCTGTTACA CGCATGATAA CTTACCTTTT AAATTAGAAA     300
AGTCAATAGA TAATTATTAT AGATTGGTGA CATGGAAATA TTTGGACCGA GAAAAAGTCT     360
CCATCTACAA TATCACAGTG ATAGCCTCAG ATCTAGGAGC CCACTCTGTC ACTGAAACTT     420
ACATTGCCCT GATTGTGGCA GACACTAATG ACAACCCTCC TCGTTTTCCT CACACCTCCT     480
ACACAGCCTA TATTCCAGAG AACAACCTGA GGGCGCCTC CATCTTCTCA CTGACTGCAC     540
ATGATCCTGA CAGTCAGGAA AATGCACAGG TCACTTACTC TGTGTCTGAG ACACCATAC     600
AGGGAGTGCC TTTGTCCTCT TATATCTCCA TCAACTCAGA TACTGGTGTC CTGTATGCAC     660
TGCACTCTTT TGACTTCGAG AAGATACAAG ACTTGCAGCT ACTGGTTGTT GCCACTGACA     720
GTGGAAGCCC ACCTCTCAGC AGCAATGTGT CATTGAGCTT GTTTGTGTTG ACCAGAACG     780
ACAACGCACC TGAGATTCTA TATCCTAGCT TCCCCACAGA TGGCTCCACT GGTGTGGAAC     840
TAGCACCCCG CTCTGCAGAG CCTGGATACC TAGTGACCAA AGTGGTGGCA GTGGACAAAG     900
ACTCAGGACA GAATGCTTGG CTGTCCTACC GTCTGCTGAA GGCCAGCGAA CCTGGGCTCT     960
TCTCTGTAGG ACTTCACACG GGTGAGGTGC GTACAGCGAG GGCCCTGCTG ACAGAGATG    1020
CTCTCAAACA GAATCTGGTG ATGGCCGTGC AGGACCATGG CCAACCCCT CTCTCGGCCA    1080
CTGTAACTCT CACTGTGGCA GTGGCTAACA GCATCCCTGA GGTGTTGGCT GACTTGAGCA    1140
GCATTAGGAC CCCTGGGGTA CCAGAGGATT CTGATATCAC GCTCCACCTG GTGGTGGCAG    1200
TGGCTGTGGT CTCCTGTGTC TTCCTTGTCT TTGTCATTGT CCTCCTAGCT CTCAGGCTTC    1260
AGCGCTGGCA GAAGTCTCGC CAGCTCCAGG GCTCCAAAGG TGGATTGGCT CCTGCACCTC    1320
CATCACATTT TGTGGGCATC GACGGGGTAC AGGCTTTTCT ACAAACCTAT TCTCATGAAG    1380
```

-continued

```
TCTCGCTCAC TTCAGGCTCC CAGACAAGCC ACATTATCTT TCCTCAGCCC AACTATGCAG    1440
ACATGCTCAT TAACCAAGAA GGCTGTGAGA AAAATGATTC CTTATTAACA TCCATAGATT    1500
TTCATGAGAG TAACCGTGAA GATGCTTGCG CCCCGCAAGC CCCGCCCAAC ACTGACTGGC    1560
GTTTCTCTCA AGCCCAGAGA CCCGGCACGA GCGGATCCCA AAATGGGGAT GAAACCGGCA    1620
CCTGGCCCAA CAACCAGTTC GATACAGAGA TGCTGCAAGC CATGATCTTG GCCTCTGCCA    1680
GTGAAGCCGC TGATGGGAGC TCCACTCTGG GAGGGGGCAC TGGCACTATG GGTTTGAGCG    1740
CTCGATATGG ACCCCAGTTT ACCCTGCAGC ACGTGCCTGA CTACCGCCAG AACGTGTACA    1800
TCCCTGGCAG CAATGCCACA CTGACCAACG CAGCTGGCAA ACGAGATGGC AAGGCTCCGG    1860
CAGGCGGCAA TGGCAACAAC AACAAGTCGG GCAAGAAAGA GAAGAAGTAA TATGGAGGCC    1920
AGGCCTTGAG CCACAGGGCA GCCTCCCTCC CCAGCCAGTC CAGCTTGTCC TTACTTGTAC    1980
CCAGGCCTCA GAATTTCAGG GCTCACCCCA GGATTCTGGT AGGAGCCACA GCCAGGCCAT    2040
GCTCCCCGTT GGGAAACAGA AACAAGTGCC CAAGCCAACA CCCCCTCTTT GTACCCTAGG    2100
GGGGTTGAAT ATGCAAAGAG AGTTCTGCTG GGACCCCCTA TCCAATCAGT GATTGTACCC    2160
ACATAGGTAG CAGGGTTAGT GTGGATACAC ACACACACAC ACACACACAC ACACACACAA    2220
CCCTTGTCCT CCGCAGTGCC TGCCACTTTC TGGGACTTTC TCATCCCCCT ACGCCCTTCC    2280
TTTATCCTCT CCCACCCAGA CACAGCTGCT GGAGAATAAA TTTGGGGATG CTGATGCTAA    2340
AAAAAAA                                                              2347
```

( 2 ) INFORMATION FOR SEQ ID NO:114:

( i ) SEQUENCE CHARACTERISTICS:
( A ) LENGTH: 2972 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 2..1849

( x i ) SEQUENCE DESCRIPTION: SEQ ID NO:114:

```
A GAG GCT GCT CAC CAC CTG GTC CTC ACG GCC TCG GAT GGC GGC AAG        46
  Glu Ala Ala His His Leu Val Leu Thr Ala Ser Asp Gly Gly Lys
  1               5                  10                  15

CCG CCT CGC TCT AGC ACA GTG CGC ATC CAC GTG ACA GTG TTG GAT ACA      94
Pro Pro Arg Ser Ser Thr Val Arg Ile His Val Thr Val Leu Asp Thr
             20                  25                  30

AAT GAC AAT GCC CCG GTT TTT CCT CAC CCG ATT TAC CGA GTG AAA GTC     142
Asn Asp Asn Ala Pro Val Phe Pro His Pro Ile Tyr Arg Val Lys Val
         35                  40                  45

CTT GAG AAC ATG CCC CCA GGC ACG CGG CTG CTT ACT GTA ACA GCC AGC     190
Leu Glu Asn Met Pro Pro Gly Thr Arg Leu Leu Thr Val Thr Ala Ser
     50                  55                  60

GAC CCG GAT GAG GGA ATC AAC GGA AAA GTG GCA TAC AAA TTC CGG AAA     238
Asp Pro Asp Glu Gly Ile Asn Gly Lys Val Ala Tyr Lys Phe Arg Lys
 65                  70                  75

ATT AAT GAA AAA CAA ACT CCG TTA TTC CAG CTT AAT GAA AAT ACT GGG     286
Ile Asn Glu Lys Gln Thr Pro Leu Phe Gln Leu Asn Glu Asn Thr Gly
 80                  85                  90                  95

GAA ATA TCA ATA GCA AAA AGT CTA GAT TAT GAA GAA TGT TCA TTT TAT     334
Glu Ile Ser Ile Ala Lys Ser Leu Asp Tyr Glu Glu Cys Ser Phe Tyr
            100                 105                 110
```

-continued

```
GAA ATG GAA ATA CAA GCC GAA GAT GTG GGG GCA CTT CTG GGG AGG ACC     382
Glu Met Glu Ile Gln Ala Glu Asp Val Gly Ala Leu Leu Gly Arg Thr
        115             120                 125

AAA TTG CTC ATT TCT GTG GAA GAT GTA AAT GAC AAT AGA CCA GAA GTG     430
Lys Leu Leu Ile Ser Val Glu Asp Val Asn Asp Asn Arg Pro Glu Val
        130             135                 140

ATC ATT ACG TCT TTG TTT AGC CCA GTG TTA GAA AAT TCT CTT CCC GGG     478
Ile Ile Thr Ser Leu Phe Ser Pro Val Leu Glu Asn Ser Leu Pro Gly
        145             150                 155

ACA GTA ATT GCC TTC TTG AGT GTG CAT GAC CAA GAC TCT GGA AAG AAT     526
Thr Val Ile Ala Phe Leu Ser Val His Asp Gln Asp Ser Gly Lys Asn
160             165                 170                 175

GGT CAA GTT GTC TGT TAC ACA CGT GAT AAT TTA CCT TTT AAA TTA GAA     574
Gly Gln Val Val Cys Tyr Thr Arg Asp Asn Leu Pro Phe Lys Leu Glu
                180                 185                 190

AAG TCA ATA GGT AAT TAT TAT AGA TTA GTG ACA AGG AAA TAT TTG GAC     622
Lys Ser Ile Gly Asn Tyr Tyr Arg Leu Val Thr Arg Lys Tyr Leu Asp
                195                 200                 205

CGA GAA AAT GTC TCT ATC TAC AAT ATC ACA GTG ATG GCC TCA GAT CTA     670
Arg Glu Asn Val Ser Ile Tyr Asn Ile Thr Val Met Ala Ser Asp Leu
        210                 215                 220

GGA ACA CCA CCT CTG TCC ACT GAA ACT CAA ATC GCT CTG CAC GTG GCA     718
Gly Thr Pro Pro Leu Ser Thr Glu Thr Gln Ile Ala Leu His Val Ala
        225                 230                 235

GAC ATT AAC GAC AAC CCT CCT ACT TTC CCT CAT GCC TCC TAC TCA GCG     766
Asp Ile Asn Asp Asn Pro Pro Thr Phe Pro His Ala Ser Tyr Ser Ala
240                 245                 250                 255

TAT ATC CTA GAG AAC AAC CTG AGA GGA GCC TCC ATC TTT TCC TTG ACT     814
Tyr Ile Leu Glu Asn Asn Leu Arg Gly Ala Ser Ile Phe Ser Leu Thr
                260                 265                 270

GCA CAC GAC CCC GAC AGC CAG GAG AAT GCC CAG GTC ACT TAC TCT GTG     862
Ala His Asp Pro Asp Ser Gln Glu Asn Ala Gln Val Thr Tyr Ser Val
                275                 280                 285

ACC GAG GAC ACG CTG CAG GGG GCG CCC CTG TCC TCG TAT ATC TCC ATC     910
Thr Glu Asp Thr Leu Gln Gly Ala Pro Leu Ser Ser Tyr Ile Ser Ile
        290                 295                 300

AAC TCT GAC ACC GGT GTC CTG TAT GCG CTG CAA TCT TTC GAC TAT GAG     958
Asn Ser Asp Thr Gly Val Leu Tyr Ala Leu Gln Ser Phe Asp Tyr Glu
        305                 310                 315

CAG ATC CGA GAC CTG CAG CTA CTG GTA ACA GCC AGC GAC AGC GGG GAC    1006
Gln Ile Arg Asp Leu Gln Leu Leu Val Thr Ala Ser Asp Ser Gly Asp
320                 325                 330                 335

CCG CCC CTC AGC AGC AAC ATG TCA CTG AGC CTG TTC GTG CTG GAC CAG    1054
Pro Pro Leu Ser Ser Asn Met Ser Leu Ser Leu Phe Val Leu Asp Gln
                340                 345                 350

AAT GAC AAC GCG CCC GAG ATC CTG TAC CCC GCC CTC CCC ACA GAC GGT    1102
Asn Asp Asn Ala Pro Glu Ile Leu Tyr Pro Ala Leu Pro Thr Asp Gly
                355                 360                 365

TCC ACT GGC GTG GAG CTG GCG CCC CGC TCC GCA GAG CGT GGC TAC CTG    1150
Ser Thr Gly Val Glu Leu Ala Pro Arg Ser Ala Glu Arg Gly Tyr Leu
        370                 375                 380

GTG ACC AAG GTG GTG GCG GTG GAC AGA GAC TCG GGC CAG AAC GCC TGG    1198
Val Thr Lys Val Val Ala Val Asp Arg Asp Ser Gly Gln Asn Ala Trp
385                 390                 395

CTG TCC TAC CGC CTG CTC AAG GCC AGC GAG CCG GGA CTC TTC TCG GTG    1246
Leu Ser Tyr Arg Leu Leu Lys Ala Ser Glu Pro Gly Leu Phe Ser Val
400                 405                 410                 415

GGT CTG CAC ACG GGC GAG GTG CGC ACG GCG CGA GCC CTG CTG GAC AGA    1294
Gly Leu His Thr Gly Glu Val Arg Thr Ala Arg Ala Leu Leu Asp Arg
                420                 425                 430
```

-continued

| GAC Asp | GCG Ala | CTC Leu | AAG Lys 435 | CAG Gln | AGC Ser | CTC Leu | GTG Val 440 | GTG Val | GCC Ala | GTC Val | CAG Gln | GAC Asp | CAT His 445 | GGC Gly | CAG Gln | 1342 |
| CCC Pro | CCT Pro | CTC Leu 450 | TCC Ser | GCC Ala | ACT Thr | GTC Val | ACG Thr 455 | CTC Leu | ACC Thr | GTA Val | GCC Ala | GTG Val 460 | GCT Ala | GAC Asp | AGC Ser | 1390 |
| ATC Ile | CCC Pro 465 | GAA Glu | GTC Val | CTG Leu | ACC Thr | GAG Glu 470 | TTG Leu | GGC Gly | AGT Ser | CTG Leu | AAG Lys 475 | CCT Pro | TCG Ser | GTC Val | GAC Asp | 1438 |
| CCG Pro 480 | AAC Asn | GAT Asp | TCG Ser | AGC Ser | CTT Leu 485 | ACA Thr | CTC Leu | TAT Tyr | CTC Leu | GTG Val 490 | GTG Val | GCA Ala | GTG Val | GCT Ala | GCC Ala 495 | 1486 |
| ATC Ile | TCC Ser | TGT Cys | GTC Val 500 | TTC Phe | CTC Leu | GCC Ala | TTT Phe | GTC Val 505 | GCT Ala | GTG Val | CTT Leu | CTG Leu | GGG Gly 510 | CTC Leu | AGG Arg | 1534 |
| CTG Leu | AGG Arg | CGC Arg | TGG Trp 515 | CAC His | AAG Lys | TCA Ser | CGC Arg | CTG Leu 520 | CTC Leu | CAG Gln | GAT Asp | TCC Ser | GGT Gly 525 | GGC Gly | AGA Arg | 1582 |
| TTG Leu | GTA Val | GGC Gly 530 | GTG Val | CCT Pro | GCC Ala | TCA Ser | CAT His 535 | TTT Phe | GTG Val | GGT Gly | GTT Val | GAG Glu 540 | GAG Glu | GTA Val | CAG Gln | 1630 |
| GCT Ala | TTC Phe 545 | CTG Leu | CAG Gln | ACC Thr | TAT Tyr | TCC Ser 550 | CAG Gln | GAA Glu | GTC Val | TCC Ser | CTC Leu 555 | ACC Thr | GCC Ala | GAC Asp | TCG Ser | 1678 |
| CGG Arg 560 | AAG Lys | AGT Ser | CAC His | CTG Leu 565 | ATC Ile | TTT Phe | CCC Pro | CAG Gln | CCC Pro 570 | AAC Asn | TAC Tyr | GCA Ala | GAC Asp | ATG Met | CTC Leu 575 | 1726 |
| ATC Ile | AGT Ser | CAG Gln | GAG Glu 580 | GGC Gly | TGT Cys | GAG Glu | AAA Lys | AAT Asn 585 | GAT Asp | TCT Ser | TTG Leu | TTA Leu | ACA Thr 590 | TCC Ser | GTA Val | 1774 |
| GAT Asp | TTT Phe | CAT His 595 | GAA Glu | TAT Tyr | AAG Lys | AAT Asn | GAA Glu 600 | GCT Ala | GAT Asp | CAT His | GGT Gly | CAG Gln 605 | GTG Val | AGT Ser | TTA Leu | 1822 |
| GTT Val | CTT Leu | TGC Cys 610 | TTG Leu | CTT Leu | TTA Leu | ATT Ile | TCC Ser 615 | AGA Arg | TGAATTTTAT | | | TTGGCATAAA | | | | 1869 |

| TTATGTTTTG | AAAAACATTG | TGAAGATAGT | TGAAAATAAT | TTTTAAGGTG | TATCACAGAG | 1929 |
| TTTTGGGTTT | ATTTTGGTGG | TGTTACCAAA | AAATTGAACT | CTAATAGTCA | TAGGTTATTG | 1989 |
| TTTCATTTGC | TTTTAAACGA | CTTGGAAAAG | ATTGTTCCAC | CATTTTAAAC | CTTCCAGTAT | 2049 |
| TTTATTCCTA | TTATCACTCA | TTCACTTAAG | AAGTAGCTAC | CCGTCCATAC | TGGTAATTTT | 2109 |
| GCTATTGTTT | GTTTGTGTGT | GTGTGTGTGT | GTGTGTGTGT | GTGTGTGTAT | CCCAAACTAG | 2169 |
| AACTTCAGAA | AATTATCAAG | AAGTCTAAAG | CCTTGTTATT | AGCTTAGCAA | AAGTAAAATA | 2229 |
| TATCTCAGAA | TTTTAGGGT | TATGTTTAGC | ATTTGAACCT | GTAACTAGGC | TCTTGTATAT | 2289 |
| TTCTTCACTT | TAAACCTCTT | TTCTGAGCCC | TGTTTCTGTA | CCAGTGCCCT | TCAAAACTTT | 2349 |
| AATACTTCTT | ACCATCCTTC | AAAACATGAA | CAAACTTTAA | AGATGGATCT | TGGTGGGAGA | 2409 |
| TGAGACTGGT | TACTAAATAT | TAAGTATGTG | AGTCAGTGGT | CACCTGGGCT | CCATCCCCAT | 2469 |
| GGAGACATGA | AATCTAAAGC | CTAGAATGTC | CATTGCTCCC | CCAAACAAAA | AACAAAAGCA | 2529 |
| AAAACATTAG | ATCTGAATTA | AAATGTAATT | TTAAACTGTT | GAAAGTGACT | TTTGTAAAAT | 2589 |
| ATGTAAGAAC | ATATTTCAAT | ACAATTCCAA | TTAGCTGTTT | CGGTTGTGCA | TTGATGTGAA | 2649 |
| GTGGTGAGAA | TGTTGATATT | AAGAACCAAT | GTTTCAGGTA | CACAAGTTCT | AAATAAGCTG | 2709 |
| ATCAATTCAA | TTAAAGTTAT | TCAGTCTTGG | CTGGACACAG | TGCCTCATGT | CTGAAATCCC | 2769 |
| AGCACTTTGG | GAGGCTGGGG | CAGGAGGACC | GCTTGAGCCC | CGGGGGTTTG | AAACTGCAGT | 2829 |

```
GAGCTATGAT CATGCCACTG CACTCCAGCC TAGGTGGCAG AACTAGACCC TGTCTCTAAA    2889

AAAACTATTA TTAGGCCGCG TGCGGTGGCT CACGCCTGTA ATCCCAGCAC TTTGGGAGAC    2949

TGAGGTGGGT GGATCACCTG AGC                                            2972
```

( 2 ) INFORMATION FOR SEQ ID NO:115:

( i ) SEQUENCE CHARACTERISTICS:
        ( A ) LENGTH: 616 amino acids
        ( B ) TYPE: amino acid
        ( D ) TOPOLOGY: linear ( i i ) MOLECULE TYPE: protein ( x i ) SEQUENCE DESCRIPTION: SEQ ID NO:115:

```
Glu Ala Ala His His Leu Val Leu Thr Ala Ser Asp Gly Gly Lys Pro
 1               5                  10                  15

Pro Arg Ser Ser Thr Val Arg Ile His Val Thr Val Leu Asp Thr Asn
             20                  25                  30

Asp Asn Ala Pro Val Phe Pro His Pro Ile Tyr Arg Val Lys Val Leu
         35                  40                  45

Glu Asn Met Pro Pro Gly Thr Arg Leu Leu Thr Val Thr Ala Ser Asp
     50                  55                  60

Pro Asp Glu Gly Ile Asn Gly Lys Val Ala Tyr Lys Phe Arg Lys Ile
 65                  70                  75                  80

Asn Glu Lys Gln Thr Pro Leu Phe Gln Leu Asn Glu Asn Thr Gly Glu
                 85                  90                  95

Ile Ser Ile Ala Lys Ser Leu Asp Tyr Glu Glu Cys Ser Phe Tyr Glu
            100                 105                 110

Met Glu Ile Gln Ala Glu Asp Val Gly Ala Leu Leu Gly Arg Thr Lys
        115                 120                 125

Leu Leu Ile Ser Val Glu Asp Val Asn Asp Asn Arg Pro Glu Val Ile
    130                 135                 140

Ile Thr Ser Leu Phe Ser Pro Val Leu Glu Asn Ser Leu Pro Gly Thr
145                 150                 155                 160

Val Ile Ala Phe Leu Ser Val His Asp Gln Asp Ser Gly Lys Asn Gly
                165                 170                 175

Gln Val Val Cys Tyr Thr Arg Asp Asn Leu Pro Phe Lys Leu Glu Lys
            180                 185                 190

Ser Ile Gly Asn Tyr Tyr Arg Leu Val Thr Arg Lys Tyr Leu Asp Arg
        195                 200                 205

Glu Asn Val Ser Ile Tyr Asn Ile Thr Val Met Ala Ser Asp Leu Gly
    210                 215                 220

Thr Pro Pro Leu Ser Thr Glu Thr Gln Ile Ala Leu His Val Ala Asp
225                 230                 235                 240

Ile Asn Asp Asn Pro Pro Thr Phe Pro His Ala Ser Tyr Ser Ala Tyr
                245                 250                 255

Ile Leu Glu Asn Asn Leu Arg Gly Ala Ser Ile Phe Ser Leu Thr Ala
            260                 265                 270

His Asp Pro Asp Ser Gln Glu Asn Ala Gln Val Thr Tyr Ser Val Thr
        275                 280                 285

Glu Asp Thr Leu Gln Gly Ala Pro Leu Ser Ser Tyr Ile Ser Ile Asn
    290                 295                 300

Ser Asp Thr Gly Val Leu Tyr Ala Leu Gln Ser Phe Asp Tyr Glu Gln
305                 310                 315                 320

Ile Arg Asp Leu Gln Leu Leu Val Thr Ala Ser Asp Ser Gly Asp Pro
                325                 330                 335
```

```
Pro   Leu   Ser   Ser   Asn   Met   Ser   Leu   Ser   Leu   Phe   Val   Leu   Asp   Gln   Asn
                  340                           345                           350

Asp   Asn   Ala   Pro   Glu   Ile   Leu   Tyr   Pro   Ala   Leu   Pro   Thr   Asp   Gly   Ser
            355                           360                           365

Thr   Gly   Val   Glu   Leu   Ala   Pro   Arg   Ser   Ala   Glu   Arg   Gly   Tyr   Leu   Val
      370                           375                     380

Thr   Lys   Val   Val   Ala   Val   Asp   Arg   Asp   Ser   Gly   Gln   Asn   Ala   Trp   Leu
385                           390                     395                                 400

Ser   Tyr   Arg   Leu   Leu   Lys   Ala   Ser   Glu   Pro   Gly   Leu   Phe   Ser   Val   Gly
                        405                           410                           415

Leu   His   Thr   Gly   Glu   Val   Arg   Thr   Ala   Arg   Ala   Leu   Leu   Asp   Arg   Asp
                  420                           425                           430

Ala   Leu   Lys   Gln   Ser   Leu   Val   Val   Ala   Val   Gln   Asp   His   Gly   Gln   Pro
            435                           440                           445

Pro   Leu   Ser   Ala   Thr   Val   Thr   Leu   Thr   Val   Ala   Val   Ala   Asp   Ser   Ile
      450                           455                           460

Pro   Glu   Val   Leu   Thr   Glu   Leu   Gly   Ser   Leu   Lys   Pro   Ser   Val   Asp   Pro
465                           470                           475                           480

Asn   Asp   Ser   Ser   Leu   Thr   Leu   Tyr   Leu   Val   Val   Ala   Val   Ala   Ala   Ile
                        485                           490                           495

Ser   Cys   Val   Phe   Leu   Ala   Phe   Val   Ala   Val   Leu   Leu   Gly   Leu   Arg   Leu
                  500                           505                           510

Arg   Arg   Trp   His   Lys   Ser   Arg   Leu   Leu   Gln   Asp   Ser   Gly   Gly   Arg   Leu
            515                           520                           525

Val   Gly   Val   Pro   Ala   Ser   His   Phe   Val   Gly   Val   Glu   Glu   Val   Gln   Ala
      530                           535                           540

Phe   Leu   Gln   Thr   Tyr   Ser   Gln   Glu   Val   Ser   Leu   Thr   Ala   Asp   Ser   Arg
545                           550                           555                           560

Lys   Ser   His   Leu   Ile   Phe   Pro   Gln   Pro   Asn   Tyr   Ala   Asp   Met   Leu   Ile
                        565                           570                           575

Ser   Gln   Glu   Gly   Cys   Glu   Lys   Asn   Asp   Ser   Leu   Leu   Thr   Ser   Val   Asp
                  580                           585                           590

Phe   His   Glu   Tyr   Lys   Asn   Glu   Ala   Asp   His   Gly   Gln   Val   Ser   Leu   Val
            595                           600                           605

Leu   Cys   Leu   Leu   Leu   Ile   Ser   Arg
      610                     615
```